United States Patent [19]

Kucera et al.

[11] Patent Number: 4,926,356

[45] Date of Patent: May 15, 1990

[54] TEST APPARATUS FOR MEASURING HEAT RELEASE OF CERTAIN MATERIALS

[75] Inventors: Lawrence P. Kucera, Seattle; Michael P. Thompson, Tacoma, both of Wash.

[73] Assignee: The Boeing Company, Seattle, Wash.

[21] Appl. No.: 162,042

[22] Filed: Feb. 29, 1988

[51] Int. Cl.⁵ ..................... G01K 17/06; G06F 15/20
[52] U.S. Cl. .................................. 364/557; 364/556; 374/32; 374/31
[58] Field of Search ..................... 374/31, 32, 36, 37, 374/8, ; 364/189, 478, 479, 550, 556, 557; 378/8; 73/190 R

[56] References Cited

U.S. PATENT DOCUMENTS

| 3,544,218 | 6/1967 | Cassidy | 378/8 |
| 3,706,877 | 12/1972 | Clifford, Jr. et al. | 235/151.35 |
| 3,724,251 | 4/1973 | Kydd et al. | 73/190 |
| 4,059,007 | 11/1977 | Miller et al. | 73/190 R |
| 4,163,388 | 8/1979 | November | 73/190 |
| 4,315,430 | 2/1982 | Szonntagh | 73/190 |
| 4,329,873 | 5/1982 | Maeda | 73/190 |
| 4,337,654 | 7/1982 | Austin et al. | 73/190 |
| 4,351,614 | 9/1982 | Garnier | 374/37 |
| 4,380,400 | 4/1983 | Searle | 374/37 |
| 4,382,698 | 5/1983 | Szonntagh | 374/37 |
| 4,386,858 | 6/1983 | Kude et al. | 374/37 |
| 4,399,502 | 8/1983 | MacDonald et al. | 364/189 |
| 4,495,584 | 1/1985 | Yoshida | 364/479 |
| 4,511,262 | 4/1985 | Arcara | 374/37 |
| 4,539,645 | 9/1985 | Krottinger et al. | 364/478 |
| 4,637,735 | 1/1987 | deRis et al. | 374/8 |
| 4,690,569 | 9/1987 | Veitch | 374/11 |
| 4,720,196 | 1/1988 | Mondeil et al. | 374/37 |
| 4,801,429 | 1/1989 | Torfs et al. | 374/12 |

OTHER PUBLICATIONS

"Smoke Density Integrator" by R. M. Storey 8 Jul. 1960 in British Journal of Applied Physics (Nov. 1960).

Primary Examiner—Parshotam S. Lall
Assistant Examiner—V. Trans
Attorney, Agent, or Firm—Bruce A. Kaser

[57] ABSTRACT

An automatic test apparatus calculates the amount of heat released by a material. The apparatus includes a calorimeter having a heating or burn chamber in which a sample of test material is burned by subjecting it to preselected heat flux rates. A computer automatically controls the apparatus by governing sample insertion into the chamber, and monitors the amount of heat and smoke the sample releases. Heat and smoke release data is automatically generated and provided to the user after every test.

2 Claims, 2 Drawing Sheets

TEST APPARATUS FOR MEASURING HEAT RELEASE OF CERTAIN MATERIALS

TECHNICAL FIELD

This invention relates to calorimeter devices which measure heat. More particularly, it relates to automated control systems for such devices.

This specification includes a microfiche appendix totalling three sheets of microfiche having approximately 133 frames. Such appendix is available to the public for inspection pursuant to 37 C.F.R. §1.96(b)(1).

BACKGROUND ART

The commercial aircraft industry is continually looking for ways to improve aircraft fire safety. Aircraft fires can, of course, arise from a number of situations including crashes, in-flight fires caused by either passengers and/or aircraft system malfunctions, cargo compartment fires, or situations where a fire is initiated and propagated in an untended aircraft.

Improving aircraft fire safety involves the development of better and more fire-resistant construction materials. With regard to those materials which are currently used to construct interior cabin surfaces, e.g. primarily flammable materials in the passenger cabin, it has been determined fire safety is directly related to the amount of heat they release when they burn, and when they release it. For this reason, the Federal Aviation Administration (FAA) has imposed specific heat-release requirements for such materials, although it should also be appreciated the industry has for many years conducted its own tests independently of FAA regulations in order to improve fire safety.

Dr. Edwin Smith, a Professor of Chemical Engineering at Ohio State University, invented a calorimeter which measures heat release and smoke generation rates from burning materials. This calorimeter has come to be known in the field as the "OSU calorimeter" and has been specifically designated for use by the FAA in heat release testing of cabin surface material. Unfortunately, using it to run large numbers of tests using numerous material samples has long been known to be a tedious and time-consuming process, primarily because it involves manual control of calorimeter operation and manual coordination of data acquisition with calorimeter operation. The present invention eliminates these drawbacks by providing a calorimeter of the OSU type whose functions are automatically controlled by a computer in accordance with specific user-selected inputs, and which automatically reduces data immediately upon test completion.

DISCLOSURE OF THE INVENTION

An apparatus constructed in accordance with this invention includes a calorimeter whose functions is to measure the heat release rate and smoke generation rate of burning materials. The calorimeter includes an inner chamber where burning takes place. This chamber has a doorway which is automatically opened or closed for the purpose of permittinng chamber access for placing a test specimen or sample inside. The sample is so placed by an actuator ram which is also automatically controlled.

Air continually flows through the chamber at a certain calibrated rate. In actual practice, the flow rate for any given test will be dictated by the FAA. Electrical radiant heating elements inside the chamber provide sufficient heat to promote burning of the sample. Ignition of the sample is induced by flamelets which also help ignite gases produced by the sample as it burns.

The temperature of the air and any combustion products exiting the chamber is continuously monitored by suitable sensors such as thermocouples. The increase in exit gas temperature is known to be directly proportional to the heat released by the test sample, and therefore, exit gas temperature data can be directly converted into heat release data. Integrating such data over a given period of time gives the total amount of heat released by the sample.

The calorimeter also includes a light source and photocell positioned across from each other in a manner so that the exit gas passes between them. Any smoke in the gas decreases the amount of light transmitted to the photocell. The decrease in percent of light transmission is known to be logarithmically related to the increase in smoke generation thus making it possible to obtain total smoke generation data.

The apparatus includes a programmable computer operatively connected to the various above-described hardware elements of the calorimeter. The computer has conventionally-known input/output devices which, respectively, permit the user to input and receive computer information. The computer's programming causes it to display certain user-selectable options which are to be employed during any given test for controlling calorimeter hardware. Such options include, for example, selection of the times at which the chamber's doorway is to be automatically opened and closed, and operation of the ram to move the sample into the chamber. Also the user selects the total time the sample remains in the chamber during burning, the rate of airflow through the chamber, and the radiant heat supplied to the sample during burning.

The computer maintains both this information and certain additional calibration information which it uses in the calculation of heat release and smoke generation rates. Then, the computer operates the calorimeter in accordance with the user-selected options and continually measures the resultant exit gas temperature and decrease in photocell light reception, which is used to calculate heat release and smoke generation data. The computer also makes this data immediately available to the user.

An advantage of the present invention is that it provides a menu-driven integrated data acquisition/control/reduction system which automatically controls the chamber doorway and sample ram, senses temperature changes and photocell readings, and calculates heat and smoke release results. It is also an advantage that test results are reported immediately to the user after each test is completed.

The apparatus can be used with a minimum amount of user effort and training. Also, any changes in desired testing conditions or procedures which formerly required time-consuming revisions can be implemented immediately. These advantages, and others, will become apparent to the reader upon considering the following description in conjunction with the drawings.

BRIEF DESCRIPTION OF THE DRAWINGS

In the drawings, like reference numerals refer to like parts throughout the various views, and.

Figure 1:
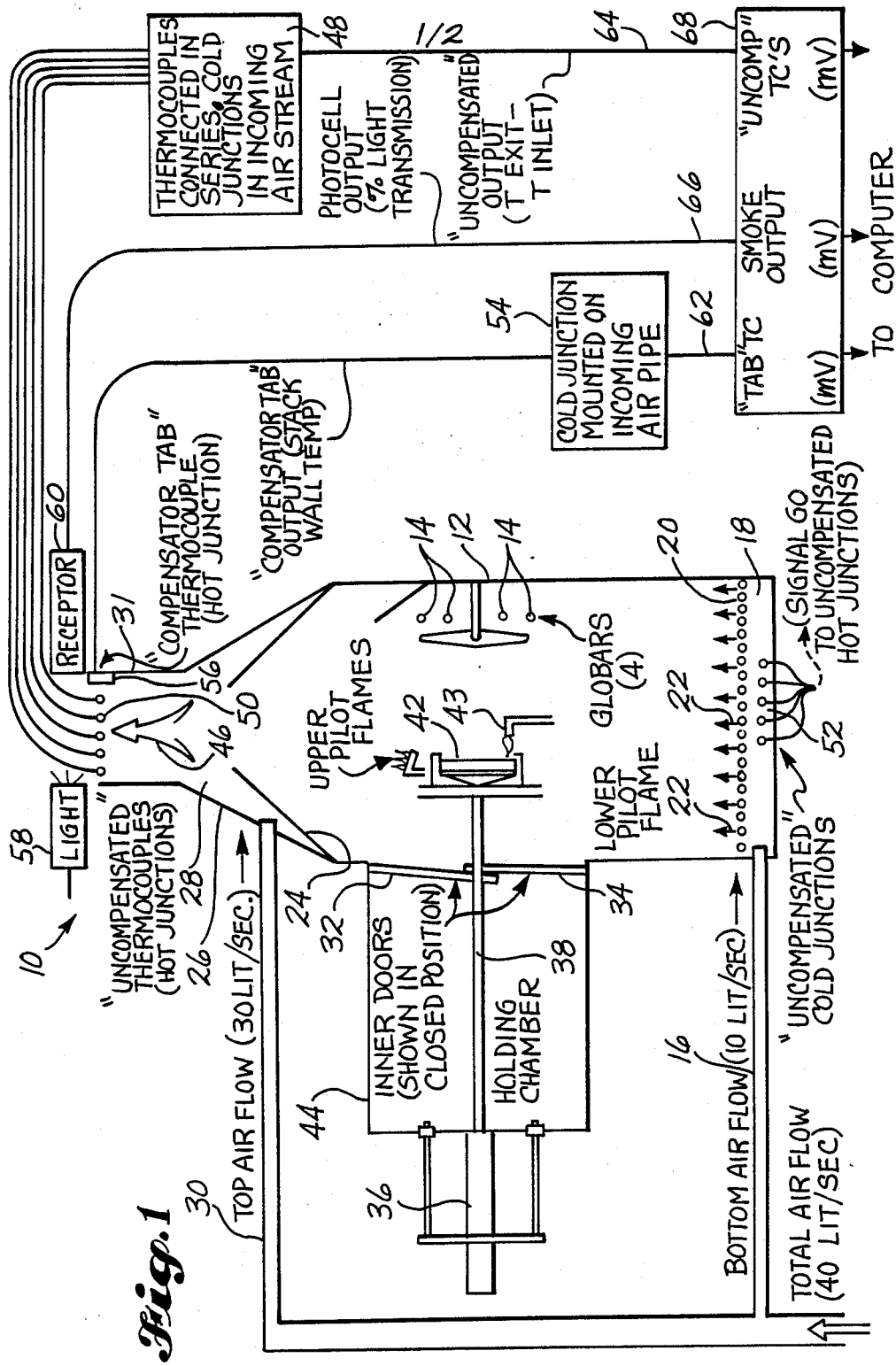
FIG. 1 is a schematic view of a calorimeter constructed in accordance with the invention, and shows the various hardware elements of the calorimeter.

BEST MODE FOR CARRYING OUT THE INVENTION (1) General Description of the System Referring to the drawings, and first to FIG. 1, therein is shown at 10 a schematic of a calorimeter constructed in accordance with the invention. It includes a burn chamber 12 in which is received a plurality of radiant heating elements in the form of silicon carbide glow bars 14. Preferably, there are four of these positioned in a vertical plane and parallel with respect to each other.

An airflow is delivered into the bottom of the chamber as shown at 16. The rate of such airflow is user-selectible although it should be understood that in order to encourage uniformity in industry testing, the FAA may require a certain predetermined flow rate. For example, the preferred bottom airflow rate may be 10 liters per second. The bottom air is delivered into a chamber space 18 which is below a perforated pan 20. The pan 20 creates a uniform airflow upwardly through the chamber as indicated by arrows 22.

The top of the burn chamber has inner and outer walls 24, 26. An airflow is delivered into the space 28 between them, as is shown at 30. In preferred form, the flow rate of this top airflow should be 30 liters per second, meaning the total airflow delivered to the calorimeter 10 and exiting from the burn chamber's stack 31 should be approximately 40 liters per second. The sole purpose of the top airflow 30 is to cool the burn chamber's outer walls thus preventing them from getting too hot.

Access into the chamber 12 is provided by doors 32, 34. These doors are shown in a closed position, but may be opened by swinging them outwardly. Conventionally-known actuators, controlled by relays, are used to swing the doors. An actuator ram 36 has a rod 38 that is extendible and retractable into the burn chamber 12 for insertion/removal of a test sample 42. At the end of the rod 38 is a holder 40 shaped to fixedly hold the sample 42. Since the amount of heat any particular sample releases is also a function of the sample's mass, uniform sample sizing has been established by the FAA. Typically, for example, sample size will be 6 inches by 6 inches and up to one and one-half inches thick, although it should be appreciated the invention has the capability of handling many sizes different from this.

The sample 42 is placed in holder 40 when rod 38 is retracted into a holding chamber 44 that is positioned outside and over doors 32, 34. The doors 32, 34 are then opened and the rod 38 is extended, thrusting the sample 42 into the chamber airflow. There, it is subject to heat by glow bars 14 and is ignited by pilot flame 43. The doors 32, 34 close immediately after the sample 42 is placed in the chamber 12. The doors have slots which permit them to close over the extended rod 38.

The temperature of the airflow 46 or gas exiting the burn chamber through stack 31 is continuously monitored by a plurality of thermocouples 48, preferably five in number that are connected in series. Their hot junctions are placed across the stack's opening as shown at 50 and their cold junctions are placed in bottom chamber 18, below pan 20 as shown at 52. The circuit created by thermocouples 48 provides an uncompensated output which roughly measures exit gas temperature. A compensator tab thermocouple 54 is also used to compensate their output. This latter thermocouple has a hot junction connected at 56 directly to the wall of the chamber's stack 31, and its cold junction is suitably connected somewhere in the conduit 16 which delivers incoming air to bottom chamber 18. As would be familiar to a person skilled in the art, both the uncompensated and compensated thermocouples 48, 54 provide output signals in milli-volts.

The purpose of the circuit created by the compensator tab thermocouple 54 is that the uncompensated thermocouples 48 have a relatively slow response time, meaning they respond slowly to any rapid changes in exit gas temperature during a particular test. Their response time can be improved by using the "compensated" signal from thermocouple 54, by subtracting its output from the output of thermocouples 48. Hence, the compensated output is determined as follows:

$$T_{comp} = T_{uncomp} - T_{tab}$$

In practice, use of the compensated signal results in a slightly higher peak release rate calculation than use of the uncompensated signal, at least for those materials which rise quickly to a peak heat release rate and then immediately drop off. However, the total heat release results integrated over a certain period of time are virtually identical using either method.

Mounted to the top of the chamber's stack 31 is a light source 58 and photocell receptor 60. Smoke produced by the burning sample 42 passes between them and reduces the percentage of light received by the photocell 60. The photocell's output is also in milli-volts.

Figure 2:
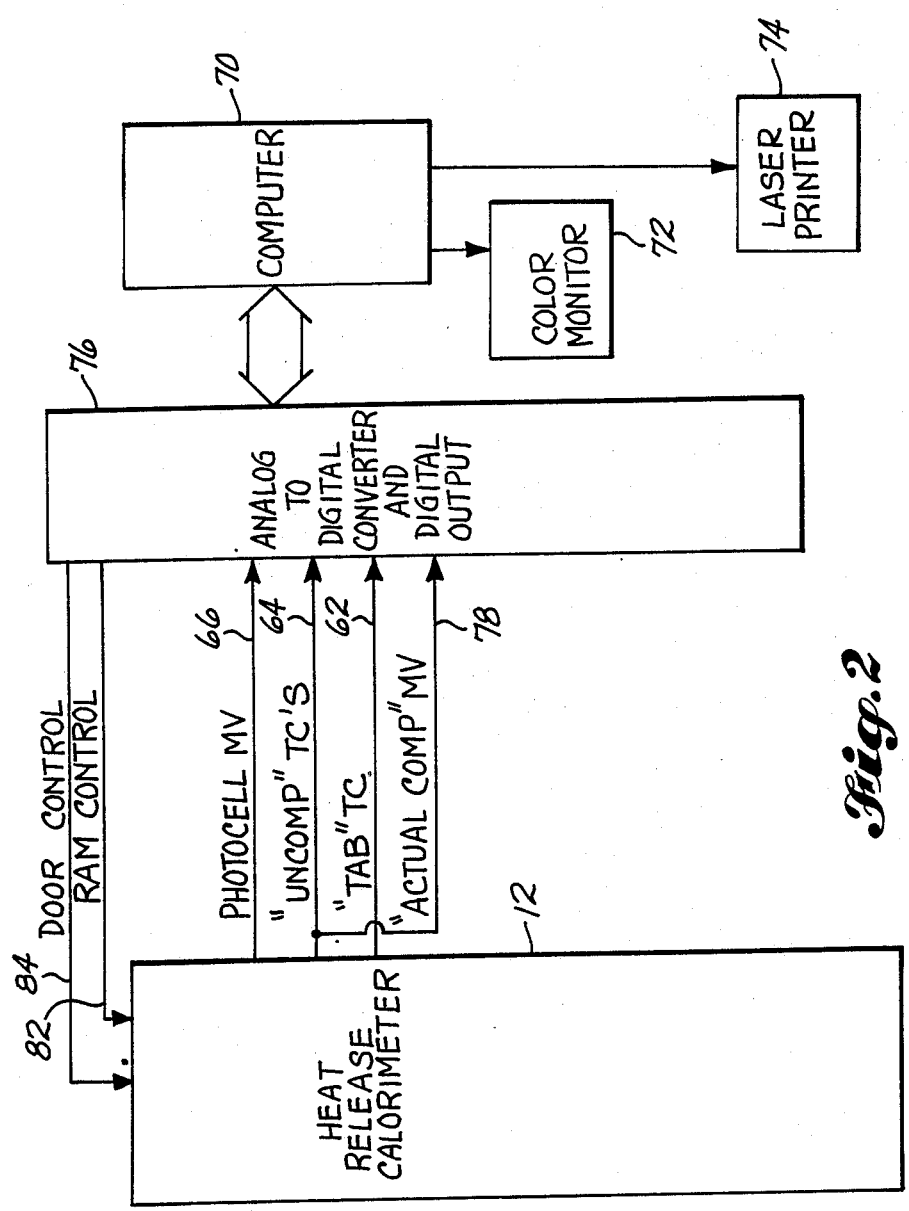
FIG. 2 is a schematic view of the invention and shows how a computer is operably connected to the hardware elements of the calorimeter shown in FIG. 1.

The outputs of thermocouples 54, 48 and photocell 60 are shown, respectively, at 62, 64 and 66 in FIG. 1. These outputs are transmitted to a computer as indicated at 68. Referring to FIG. 2, therein is shown a preferred computer 70 operatively connected to the calorimeter 12. By way of illustrative example, a computer suitable for use with this invention is the Compaq (trademark) Deskpro 286 which would be familiar to a person skilled in the art. A conventional color monitor 72 and laser printer 74 are used in connection with the computer 72 as a means for displaying output information. As a person skilled in the art would realize, the Compaq (trademark) computer 70 has a conventional keyboard which provides the user with a means for inputting data.

A conventional analog-to-digital converter 76 interfaces the computer 70 with the calorimeter's previously-described hardware elements. As described above, thermocouple and photocell signals are in the form of milli-volts which are received directly by the interface 76 and converted into digital form. If desired, the output of the uncompensated thermocouples 48 may be compensated by a summing junction in accordance with the above equation, and output in milli-volts as shown at 78 to the interface 76. The computer also operates the relays governing door and ram control digitally as shown at 82, 84, respectively, in accordance with instructions specified by the user.

To summarize the invention's hardware elements or parameters as described above, the computer must have a separate input channel for the uncompensated thermocouple and tab thermocouple circuits 64, 62, the actual compensated thermocouple circuit 78 and the photocell circuit 66. The computer must also have separate digital output channels 82 and 84 for controlling opening and closing movement of the door, and ram extension and retraction.

(2) System Programming Requirements

As stated above, an important feature of the invention is that it is menu-driven and minimizes the amount of training and time required to operate it. All necesssary test variations are incorporated into a menu of options displayed to the user who is prompted by the computer 70 to provide the test parameters he or she desires. This makes it possible for a user totally unfamiliar with the invention to conduct a test after only a few minutes familiarization with the system. The programming requirements for the system can be separated into separate sections including menu-driven options; calibration; automated door operation and test sample insertion; data retention; and data acquisition and reduction. Although all programming requirements would be readily understood by a person skilled in the art upon consideration of the appended computer program, some of the key programming requirements are summarized below.

MENU-DRIVEN OPTIONS

The software causes the computer to prompt the user to select a number of options displayed on the color monitor 72. These options are instantly selected and implemented during a particular test run. The options include:

b. Heat flux selection;
c. Calibration constant selection;
d. Compensated or uncompensated thermocouples;
e. Blank run or no blank run;
f. Number of specimens per set;
g. Number of thermocouples in uncompensated thermopile;
h. Airflow rate;
i. Specimen surface area;
j. Change of channels read by computer; and
k. Monitoring channels of the analog-to-digital converter.

Most of the above options are self-explanatory to a person skilled in the art. Briefly, time sequencing includes specifying the entire time during which a test sample is to remain in holding chamber 44, sequencing the times of door opening and closing movement along with ram extension and retraction, specifying the total time the sample is to remain in the burn chamber, and specifying the times at which data is to be reported to the user. Heat flux selection provides the amount of heat generated by the adjustable glow bars 14. The calibration constant selection relates to known heat transfer calibration constants which are develoed by burning known flow rates of methane in the calorimeter burn chamber 12, and then recording the resultant compensated and uncompensated thermocouple or thermopile outputs. Compensated or uncompensated thermocouple selection permits the user to select solely the output of uncompensated thermocouples 48 if he or she desires.

Specifying a blank run means that a test run is to be made exactly the same way as an actual test run with the exception that a sample material is not placed in holder 40. The purpose of a blank run is that it is known that when a test specimen is initially injected into burn chamber 12, there is an immediate rush of cold air from holding chamber 44 into the chamber. This consequently reduces the temperature of the exit gas, albeit briefly. Furthermore, a good deal of heat is lost in heating up the specimen holder itself. If these heat losses are not taken into account, the test will show a "negative heat release" at the start of every test. Data generated from a blank run is subtracted from actual test run data to cancel out these losses.

The user is permitted to conduct a series of tests using a number of specimens. Therefore, the user has the option of specifying any number of specimens or samples up to twenty, although this number can be easily varied if desired. Since, as described above, five thermocouples are preferably connected in series across calorimeter stack 31, the user is provided with the option of determining the number of thermocouples in this thermopile which are to be used.

Airflow rate requires the user to insert air pressure and temperature data so that the computer can automatically provide a calculated airflow rate. The options specified in paragraphs i-j are self-explanatory.

SOFTWARE CALIBRATION

The software facilites calibration of heat flux, smoke and airflow. All input/output channels can be monitored simultaneously permitting easy computer computation of any necessary calibration constants. With regard to smoke, the software prompts the user to insert glass filters for photocell calibration tests prior to burning any test samples. The software automatically takes milli-volt data from the use of such filters and makes a best curve fit to provide a calibration curve for converting photocell milli-volt data, taken during an actual test, into smoke release rate data.

AUTOMATED DOOR OPERATION AND SAMPLE INSERTION

In accordance with the above-described menu-driven options, the software triggers door and ram relays at selected times to open doors 32, 34 and insert the test sample. The software also triggers the relays to withdraw the test sample at the end of the test.

DATA RETENTION

All original milli-volt data provided to the computer is retained, so that any prior test run can be reprinted at the user's option. Any reprint can be made into a different format than the original test report by changing those options listed under menu-driven options above.

Included as an appendix hereto is a copy of a suitable computer program which embodies all of the above-discussed features. This program is written in IBM PC Pascal, Version 2.0, which would be familiar to a person skilled in the art. It is readily compatible for use in the above-identified Compaq computer. Having this program along with the above-described calorimeter and computer hardware, would enable a person skilled in the art to easily practice the invention.

Thus, a preferred embodiment of the invention has been presented above. It is to be understood that certain changes could be made to the invention without departing from the spirit and scope thereof. Any patent protection which is due as a result of this disclosure is not to be limited by the preceding description, but rather is to be limited only by the patent claim or claims which follow, wherein such claims are to be interpreted in accordance with the doctrines of patent law.

APPENDIX TO SPECIFICATION
Part I of II

```
1  {$include:'IO\SCREEN.INT'}
2  {$include:'IO\KEYBRD.INT'}
3  {$include:'TAKEDATA.INT'}
4  {$include:'PRAMIFAC.INT'}
5  {$include:'PHOTOCAL.INT'}
6  {$include:'DATAIFAC.INT'}
7  PROGRAM OSU( OUTPUT);
8
9     USES SCREEN,
10         KEYBRD,
11         TAKEDATA,
12         PRAMIFAC,
13         DATAIFAC;
14
15    CONST
16        ERRROW = 25;
17        CMDROW = 24;
18
19    VAR
20        CH: CHAR;
21
22    BEGIN
23    INITSCRN;
24    WRITEPC( 25, 1, '(C)Copyright The Boeing Company 1987');
25    CHK_SUBRUNSIZ;
26
27    RUN_SCRN;
28
29    CLRLINE( CMDROW, 1);
30    END.
```

```
1  INTERFACE(0);
2
3  UNIT AIRFLOW( AIRCAL);
4
5  PROCEDURE AIRCAL;
6
7  BEGIN
8  END;
```

```
1  {$include:'AIRFLOW.INT'}
2  {$include:'IO\SCREEN.INT'}
3  {$include:'IO\KEYBRD.INT'}
4  {$include:'IO\PROMPT.INT'}
5
6  IMPLEMENTATION OF AIRFLOW;
7
8  USES SCREEN,
9      KEYBRD,
10     PROMPT;
11
12 FUNCTION PRSRQQ( CONSTS BASE, EXPON: REAL4): REAL4; EXTERN;
13
14 PROCEDURE AIRCAL;
15
16    CONST
17        HEADING = 'Air Flow Calibration';
18        CR = CHR( 13);
19        GT0 = FVALBND( 0.0, GT, 0.0);
20        GE0 = FVALBND( 0.0, GE, 0.0);
21        GTM460 = FVALBND( -460.0, GT, 0.0);
```

```
22
23
24     VAR
25        ROW: INTEGER;
26        PAMB,         { P ambient }
27        TAMB,         { T ambient }
28        PS,           { P static  }
29        PV,           { P dynamic }
30        PABS: REAL;   { P absolute }
31        RHOO, TO, INHG_PSI, PO, INWAT_PSI: REAL;
32        FLOWRATE: REAL;
33        AGAIN: BOOLEAN;
34        CH: CHAR;
35        PSBND: FVALBND;
36
37     BEGIN
38     WRITEPC( 1, 30, HEADING);
39     CLR2_25;
40
41  {  The following constants are parameters for the equations }
42
43     RHOO       := 0.08084;         { lb/ft2.  Standard Density of Air }
44     TO         := 492.0;           { °R.      32°F }
45     INHG_PSI   := 14.7/29.92;      { Convert inches Hg to PSI. }
46     PO         := 29.92*INHG_PSI;  { psi.     ? }
47     INWAT_PSI  := INHG_PSI/13.54;  { Convert inches water to PSI }
48
49     AGAIN := TRUE;
50     ROW := 5;
51     WHILE AGAIN AND THEN
52           PROMPTR( ROW, 1, 'Barometric Pressure (" Hg) ? ', PAMB, GTO)
53     DO BEGIN
54        PAMB := PAMB * INHG_PSI;  { Convert to psi }
55        WITH PSBND DO BEGIN LOWBND := -PAMB/INWAT_PSI; BNDCHK := GT; END;
56
57        ROW := ROW+2;
58        WHILE AGAIN AND THEN
59              PROMPTR( ROW, 1, 'Air Temperature (°F) ? ', TAMB, GTM460)
60        DO BEGIN
61           TAMB := TAMB + 460;      { Convert to R }
62
63           ROW := ROW+2;
64           WHILE AGAIN AND THEN
65                 PROMPTR( ROW, 1, 'Static Pressure (" water) ? ', PS, PSBND)
66           DO BEGIN
67              PS := PS * INWAT_PSI;
68              PABS := PS + PAMB;
69
70              ROW := ROW+2;
71              IF PROMPTR( ROW, 1, 'Dynamic Pressure (" water) ? ', PV, GEO)
72              THEN BEGIN
73                 PV := PV * INWAT_PSI;
74
75                 { Note: PRSRQQ( r1, r2) = r1^r2 }
76                 FLOWRATE := (( PRSRQQ( (PV/PABS), 0.48531) * 1.54839 * PABS)/
77                                  SQRT( TAMB)) { lbs/sec }
78                             / (RHOO * PAMB/PO * TO/TAMB) { ft3/lb }
79                             * 60.0 { sec/min} ;
80
81                 POSCURS( (ROW+2), 1);
82                 WRITE( 'Flow Rate: ', FLOWRATE:0:2, ' cfm');
83
84                 WRITEPCU( 24, 1, '[A]gain /Quit ?');
```

```
 85                   REPEAT CH := GETCHU; UNTIL (CH = 'A') OR (CH = 'Q') OR (CH = CR);
 86                   AGAIN := (CH = 'A') OR (CH = CR);
 87                   END
 88                ELSE AGAIN := TRUE;
 89
 90                CLRLINE( (ROW+2), 1);
 91                CLRLINE( ROW, 1);
 92                CLRLINE( 24, 1);
 93                ROW := ROW-2;
 94                END;
 95             CLRLINE( ROW, 1);
 96             ROW := ROW-2;
 97             END;
 98          CLRLINE( ROW, 1);
 99          ROW := ROW-2;
100          END;
101       END;
102
103 BEGIN
104 END.

1 INTERFACE(0);
  2
  3 UNIT CALMENU( CAL_MENU);
  4
  5 PROCEDURE CAL_MENU;
  6
  7 BEGIN
  8 END;

1 {$include:'IO\SCREEN.INT'}
  2 {$include:'IO\KEYBRD.INT'}
  3 {$include:'IO\PROMPT.INT'}
  4 {$include:'PRAMIFAC.INT'}
  5 {$include:'AIRFLOW.INT'}
  6 {$include:'PHOTOCAL.INT'}
  7 {$include:'MVMON.INT'}
  8 {$include:'DUMMYCAL.INT'}
  9 {$include:'CALMENU.INT'}
 10
 11 IMPLEMENTATION OF CALMENU;
 12
 13 USES SCREEN,
 14      KEYBRD,
 15      PROMPT,
 16      AIRFLOW,
 17      PRAMIFAC,
 18      MVMON,
 19      PHOTOCAL,
 20      DUMMYCAL;
 21
 22 CONST
 23    FGE0 = FVALBND( 0.0, GE, 0.0);
 24    GT0 = VALBND( 0, GT, 0);
 25    GE1 = VALBND( 1, GE, 0);
 26    FGEOLE100 = FVALBND( 0.0, GELE, 100.0);
 27    GTOLEMAXSEC = VALBND( 0, GTLE, MAXSEC);
 28    GE2LEMAXFLTR = VALBND( 2, GELE, MAXFLTR);
 29
 30 VAR
 31    PR: PR_REC;
```

```
32
33 PROCEDURE DSP_CALMENU( CONST PR: PR_REC);
34    VAR
35       I, ROW: INTEGER;
36    BEGIN
37    CLR2_25;
38
39    WITH PR
40    DO BEGIN
41       ROW := 3;
42
43       WRITEPU( ROW, 1, 'heat Flux: ');
44       WRITE( HEATFLUX:0:2);
45
46       ROW := ROW + 2;
47       WRITEPU( ROW, 1, 'speciMen type: ');
48       IF SPCTYP <> ' '
49       THEN WRITE( SPCTYP)
50       ELSE WRITE( 'normal');
51       WRITEPU( ROW, 40, 'dummy specimeNs: ');
52       WRITE( DMYCNT:0);
53
54       ROW := ROW + 2;
55       WRITEPU( ROW, 1, 'filter Glass values:');
56       FOR I := 1 TO FILTERS DO WRITE( ' ',FILTER[I]:0:2);
57
58       ROW := ROW + 2;
59       WRITEPU( ROW, 1, 'Times:  hold ');
60       WRITE( HOLDTIME:0);
61       WRITE( '   average ');
62       WRITE( AVRGTIME:0);
63       WRITE( '   burn ');
64       WRITE( BURNTIME:0);
65
66       ROW := ROW + 2;
67       WRITEPU( ROW, 1, 'Vertical airflow: ');
68       WRITE( VFLOW:0:1, ' 1/sec');
69
70       END;
71    END;
72
73 PROCEDURE CAL_MENU;
74    CONST
75       HEADING = 'Calibration';
76
77    VAR
78       I, J: INTEGER;
79       DONE, UPDATE: BOOLEAN;
80       RTMP: REAL;
81       CH: CHAR;
82       GLSTR: GLSTRTYP;
83       PSTR: LSTRING(80);
84       TMPBND: VALBND;
85
86    BEGIN
87    GET_PARAM( PR);
88
89    DONE := FALSE;
90    UPDATE := TRUE;
91    REPEAT
92       WRITEPC( 1, 30, HEADING);
93       IF UPDATE THEN DSP_CALMENU( PR) ELSE UPDATE := TRUE;
94       WRITEPC( 24, 1, 'COMMAND: ');
```

```
 95        WRITEU( 'Airflow cal /Dummy cal /mv mOnitor /Photo cal /Quit ? ');
 96        CH := GETCHU;
 97        CLRLINE( 25, 1);
 98        CASE CH OF
 99
100        'A':  AIRCAL;
101
102        'D':  UPDATE := DUMMY_CAL( PR);
103
104        'F':  BEGIN
105               UPDATER( 24, 1, 'Heat flux (kW/cm²) ? ', PR.HEATFLUX, FGE0);
106               WITH PR
107               DO BEGIN
108                  IF HEATFLUX = 1.5 THEN RUNPRFX := 'A'
109                  ELSE IF HEATFLUX = 2.5 THEN RUNPRFX := 'B'
110                  ELSE IF HEATFLUX = 3.5 THEN RUNPRFX := 'C'
111                  ELSE IF HEATFLUX = 5.0 THEN RUNPRFX := 'D'
112                  ELSE IF HEATFLUX = 7.5 THEN RUNPRFX := 'E'
113                  ELSE BEGIN
114                     WRITEPC( 24, 1, 'Heat flux prefix (F..Z) ? ');
115                     REPEAT
116                        PR.RUNPRFX := GETCHU;
117                        UNTIL RUNPRFX IN ['F'..'Z'];
118                     END;
119                  END;
120               END;
121
122        'G':  BEGIN
123               UPDATEI( 24, 1, 'Number of filter values ? ',
124                        PR.FILTERS, GE2LEMAXFLTR);
125               PSTR := 'Filter #1 percent transmission ? ';
126               FOR I := 1 TO PR.FILTERS
127               DO BEGIN
128                  PSTR[9] := CHR( 48+I);
129                  UPDATER( 24, 1, PSTR, PR.FILTER[I], FGE0LE100);
130                  END;
131               END;
132
133        'M':  BEGIN
134               WRITEPC( 24, 1, 'Specimen type (A-Z,0-9 or Enter) ? ');
135               REPEAT
136                  CH := GETCHU;
137                  IF CH < ' ' THEN CH := ' ';
138                  UNTIL CH IN [' ','0'..'9','A'..'Z'];
139               PR.SPCTYP := CH;
140               END;
141
142        'N':  UPDATEI( 24, 1, 'Dummy specimens to average ? ', PR.DMYCNT, GE1);
143
144        'O':  UPDATE := MV_MONITOR;
145
146        'P':  UPDATE := PHOTO_CAL( PR);
147
148        'Q':  DONE := TRUE;
149
150        'T':  BEGIN
151               REPEAT
152                  I := PR.HOLDTIME;
153                  J := PR.AVRGTIME;
154                  UPDATEI( 24, 1, 'Hold Time (sec) ? ', I, GT0);
155                  UPDATEI( 24, 1, 'Average Time (sec) ? ', J, GT0);
156                  IF I < J
157                  THEN WRITEPC( 25, 1,
```

```
158                      'Average Time must be less than or equal to Hold Time');
159                  UNTIL I >= J;
160              CLRLINE( 25, 1);
161              PR.HOLDTIME := I;
162              PR.AVRGTIME := J;
163              UPDATEI( 24, 1, 'Burn Time (sec) ? ', PR.BURNTIME, GTOLEMAXSEC);
164              END;
165
166       'V':   UPDATER( 24, 1, 'Vertical air flow (1/sec) ? ', PR.VFLOW, FGE0);
167
168       OTHERWISE
169           BEGIN
170           WRITEPC( 25, 1, 'Unknown Command');
171           UPDATE := FALSE;
172           END;
173
174         END;
175
176       IF UPDATE THEN PUT_PARAM( PR);
177       UNTIL DONE;
178
179   CLR2_25;
180   END;
181
182 BEGIN
183 END.

1 INTERFACE(0);
 2
 3 UNIT CYBRGCAL( UNITNAME, CALREC, CAL_CHAN, BIN_OUT, RAW_CHAN, GET_CYCAL,
 4                ADC_MONITOR);
 5
 6 TYPE
 7    UNITNAME = (V,MV);
 8    CALREC = RECORD
 9             DEVICE, CHANNEL: INTEGER;
10             YR, MO, DA, HR, MN, SC: INTEGER;
11             UNITS: UNITNAME;
12             LOPNT, HIPNT: REAL;
13             OFFSET, SLOPE: REAL;
14             END;
15
16 PROCEDURE CAL_CHAN;
17 PROCEDURE BIN_OUT;
18 PROCEDURE RAW_CHAN;
19 FUNCTION GET_CYCAL( CONST FNDDEV, FNDCHN: INTEGER): CALREC;
20 PROCEDURE ADC_MONITOR;
21
22 BEGIN
23 END;
```

```
1  {$include:'CYBRGCAL.INT'}
2  {$include:'IO\SCREEN.INT'}
3  {$include:'IO\KEYBRD.INT'}
4  {$include:'IO\PROMPT.INT'}
5  {$include:'PRAMIFAC.INT'}
6  {$include:'DATACQ.INT'}
7
8  IMPLEMENTATION OF CYBRGCAL;
9
10 USES SCREEN,
11      KEYBRD,
12      PROMPT,
13      DATACQ,
14      PRAMIFAC;
15
16 CONST
17     FNONE = FVALBND( 0.0, NOCHK, 0.0);
18     GE0LE15 = VALBND( 0, GELE, 15);
19     GE1LE64 = VALBND( 1, GELE, 64);
20     GE0LE4095 = VALBND( 0, GELE, 4095);
21     GE1LE32767 = VALBND( 1, GELE, 32767);
22     FILSIZ = 32;
23
24 TYPE
25     FMTARY = ARRAY [1..5] OF INTEGER;
26     DATARY = ARRAY [1..64] OF INTEGER;
27     STR80 = STRING( 80);
28
29 VAR
30     CALFIL: FILE OF CALREC;
31
32 PROCEDURE ENDXQQ; EXTERN;
33
34 FUNCTION TICS: WORD; EXTERN;
35
36 {$include:'FILEERRS.PAS'}
37
38 FUNCTION AINFM( VARS FORMAT: FMTARY;
39                 VARS COUNT, RATE: INTEGER4;
40                 VARS TARGET: DATARY;
41                 VARS OPTIONS: STR80): INTEGER; EXTERN;
42
43 FUNCTION BITOUS( VARS BIT, VAL: INTEGER;
44                  VARS OPTIONS: STR80): INTEGER; EXTERN;
45
46 PROCEDURE GETDAT( VARS YR, MO, DA: INTEGER); EXTERN;
47
48 PROCEDURE GETTIM( VARS HR, MN, SC, HN: INTEGER); EXTERN;
49
50
51 FUNCTION FINDREC( CONST FNDDEV, FNDCHN: INTEGER;
52                   VAR CR: CALREC): INTEGER;
53 {                                                                          }
54 { Hash into the file and search for the device and channel record }
55 {                                                                          }
56     VAR
57        I, J: INTEGER;
58        FOUND: BOOLEAN;
59
60     BEGIN
61     FOUND := FALSE;
62     I := ( FNDDEV*16+FNDCHN MOD FILSIZ) + 1;
63     J := I;
```

```
64      REPEAT
65         SEEK( CALFIL, I);
66         GET( CALFIL);
67         CR := CALFIL^;
68         IF (FNDDEV = CR.DEVICE) AND (FNDCHN = CR.CHANNEL)
69         THEN FOUND := TRUE
70         ELSE IF (CR.DEVICE = -1) AND (CR.CHANNEL = -1)
71         THEN FOUND := TRUE
72         ELSE BEGIN
73            I := I MOD FILSIZ + 1;
74
75            IF I=J
76            THEN BEGIN
77
78 {           Hash exhausted }
79               I := FILSIZ+1;
80               REPEAT
81                  SEEK( CALFIL, I);
82                  IF EOF( CALFIL)
83                  THEN BEGIN
84 {                 -  File exhausted }
85
86                     FOUND := TRUE;
87                     CR.DEVICE := -1;
88                     CR.CHANNEL := -1;
89                     END
90                  ELSE IF (CR.DEVICE = FNDDEV) AND (CR.CHANNEL = FNDCHN)
91                  THEN FOUND := TRUE
92                  ELSE I := I+1;
93                  UNTIL FOUND;
94               END;
95
96            END;
97         UNTIL FOUND;
98
99      FINDREC := I;
100     END;
101
102
103 FUNCTION GET_CYCAL;
104    VAR
105       CR: CALREC;
106       I: INTEGER;
107
108    BEGIN
109    ASSIGN( CALFIL, 'cal.osu');
110    CALFIL.TRAP := TRUE;
111    CALFIL.MODE := DIRECT;
112    RESET( CALFIL);
113
114    IF CALFIL.ERRS = FLNOTFND
115    THEN BEGIN
116       CALFIL.ERRS := 0;
117       REWRITE( CALFIL);
118       CR.DEVICE := -1;
119       CR.CHANNEL := -1;
120       FOR I := 1 TO FILSIZ
121       DO BEGIN
122          CALFIL^ := CR;
123          PUT( CALFIL);
124          END;
125       END
126    ELSE IF CALFIL.ERRS <> 0 THEN FILE_ERRS( CALFIL.ERRS);
```

```
127
128     I := FINDREC( FNDDEV, FNDCHN, CR);
129     CLOSE( CALFIL);
130     GET_CYCAL := CR;
131     END;
132
133
134 PROCEDURE PUT_CYCAL( VAR CR: CALREC);
135     VAR
136         OLDCR: CALREC;
137       I: INTEGER;
138
139     BEGIN
140     ASSIGN( CALFIL, 'cal.osu');
141     CALFIL.TRAP := TRUE;
142     CALFIL.MODE := DIRECT;
143     RESET( CALFIL);
144
145     I := FINDREC( CR.DEVICE, CR.CHANNEL, OLDCR);
146     SEEK( CALFIL, I);
147     CALFIL^ := CR;
148     PUT( CALFIL);
149     CLOSE( CALFIL);
150     END;
151
152 PROCEDURE CAL_CHAN;
153     CONST
154         HEADING = 'Channel Calibration';
155
156     VAR
157         DEVICE, CHANNEL, STATUS, COL, CTRCNT, OLDTIM, CURTIM, I, AVECNT: INTEGER;
158         ROW: INTEGER;
159         COUNT, RATE, TOTAL: INTEGER4;
160         V1, V2, ADC1, ADC2, SLP, OFS, VNOW, ADCNOW: REAL;
161         AGAIN: BOOLEAN;
162         CH: CHAR;
163         FM: FMTARY;
164         RDATA: DATARY;
165         OPSTR: STRING(80);
166         CR: CALREC;
167         PR: PR_REC;
168
169     FUNCTION ADCCOUNTS: REAL;
170         VAR I: INTEGER;
171         BEGIN
172         STATUS := AINFM( FM, COUNT, RATE, RDATA, OPSTR );
173         TOTAL := RDATA[1];
174         FOR I := 2 TO AVECNT DO TOTAL := TOTAL + RDATA[I];
175         ADCCOUNTS := FLOAT( TOTAL) / FLOAT( AVECNT);
176         END;
177
178     BEGIN
179     WRITEPC( 1, 30, HEADING);
180     CLR2_25;
181     GET_PARAM( PR);
182
183     WRITEP( 3, 1, 'ADC samples: ');
184     WRITE( PR.AVECNT:0);
185
186     ROW := 6;
187     AGAIN := TRUE;
188     WHILE AGAIN AND THEN
189             PROMPTI( ROW, 1, 'Device (slot) ? ', DEVICE, GEOLE15)
```

```
190     DO BEGIN
191
192        ROW := ROW+2;
193        WHILE AGAIN AND THEN
194              PROMPTI( ROW, 1, 'Channel ? ', CHANNEL, GEOLE15)
195        DO BEGIN
196
197           FM[1] := 0;
198           FM[2] := DEVICE;
199           FM[3] := CHANNEL;
200           FM[4] := 0 ;
201           FM[5] := 4;
202           RATE := SMPLRATE;
203           COUNT := PR.AVECNT;
204           AVECNT := TRUNC( FLOAT4( COUNT));
205           COPYSTR( '&', OPSTR);
206
207           ROW := ROW+2;
208           WHILE AGAIN AND THEN
209              PROMPTR( ROW, 1, 'Voltage 1 ? ', V1, FNONE)
210           DO BEGIN
211
212              ADC1 := ADCCOUNTS;
213              POSCURS( ROW, 22);
214              WRITE( ADC1:6:1, ' ADC counts');
215
216              ROW := ROW+2;
217              WHILE AGAIN AND THEN
218                 PROMPTR( ROW, 1, 'Voltage 2 ? ', V2, FNONE)
219              DO BEGIN
220
221                 ADC2 := ADCCOUNTS;
222                 POSCURS( ROW, 22);
223                 WRITE( ADC2:6:1, ' ADC counts');
224
225                 SLP := (V2 - V1) / (ADC2 - ADC1);
226                 OFS := V1 - SLP*ADC1;
227
228                 CH := ' ';
229                 WRITEPCU( 24, 1, 'Again /Quit /Save');
230
231                 OLDTIM := ORD( TICS);
232                 ROW := ROW+2;
233                 REPEAT
234                    IF OLDTIM < 50
235                    THEN BEGIN
236                       REPEAT
237                          CURTIM := ORD( TICS);
238                          UNTIL CURTIM >= 50;
239                       END
240                    ELSE BEGIN
241                       REPEAT
242                          CURTIM := ORD( TICS);
243                          UNTIL CURTIM < 50;
244                       END;
245                    OLDTIM := CURTIM;
246
247                    ADCNOW := ADCCOUNTS;
248                    VNOW := OFS + SLP*ADCNOW;
249                    CLRLINE( ROW, 1);
250                    WRITE( 'ADC counts: ', ADCNOW:6:1, '   Voltage: ', VNOW:8:6);
251                    IF CHINPUT THEN CH := GETCHU;
252                    UNTIL (CH = 'Q') OR (CH = 'A') OR (CH = 'S');
```

```
253
254                    AGAIN := CH = 'A';
255
256                    IF CH = 'S'
257                    THEN BEGIN
258                       CR.DEVICE := DEVICE;
259                       CR.CHANNEL := CHANNEL;
260                       GETDAT( CR.YR, CR.MO, CR.DA);
261                       CR.YR := CR.YR MOD 100;
262                       GETTIM( CR.HR, CR.MN, CR.SC, I);
263                       WITH CR
264                       DO BEGIN
265                          LOPNT := ADC1;
266                          HIPNT := ADC2;
267                          OFFSET := OFS;
268                          SLOPE := SLP;
269                          END;
270                       PUT_CYCAL( CR);
271                       END;
272
273                    CLRLINE( 24, 1);
274                    CLRLINE( ROW, 1);
275                    ROW := ROW-2;
276                    END;
277                 CLRLINE( ROW, 1);
278                 ROW := ROW-2;
279                 END;
280              CLRLINE( ROW, 1);
281              ROW := ROW-2;
282              END;
283           CLRLINE( ROW, 1);
284           ROW := ROW-2;
285           END;
286        CLR2_25;
287        END;
288
289
290   PROCEDURE RAW_CHAN;
291
292      CONST
293         HEADING = 'Raw Channel Display';
294         SCALE = '----+----|----+----|----+----|----+----^' *
295                 '----+----|----+----|----+----|---+----';
296         ESC = CHR( 27);
297         WHITE = ESC * '[37m';
298         GREEN = ESC * '[32m';
299         ROWCN = 5;
300         ROWDV = ROWCN+2;
301         ROWCH = ROWDV+2;
302         ROWSS = ROWCH+2;
303         ROWSL = ROWSS+1;
304         ROWPR = ROWSS+2;
305         ROWCT = ROWPR+4;
306         ROWAN = ROWCT+2;
307         ROWAGN = 24;
308
309      VAR
310         DEVICE, CHANNEL, STATUS, COL, CTRCNT, OLDTIM, CURTIM, I, AVECNT: INTEGER;
311         SHRTRATE, ADCAVE: INTEGER;
312         COUNT, RATE, TOTAL: INTEGER4;
313         AGAIN: BOOLEAN;
314         CH: CHAR;
315         FM: FMTARY;
```

```
316        RDATA: DATARY;
317        OPSTR: STRING(80);
318
319   BEGIN
320   WRITEPC( 1, 30, HEADING);
321   CLR2_25;
322
323   AGAIN := TRUE;
324   WHILE AGAIN AND THEN
325           PROMPTI( ROWDV, 1, 'Device (slot) ? ', DEVICE, GE0LE15)
326   DO BEGIN
327
328       WHILE AGAIN AND THEN
329               PROMPTI( ROWCH, 1, 'Channel ? ', CHANNEL, GE0LE15)
330       DO BEGIN
331
332          FM[1] := 0;
333          FM[2] := DEVICE;
334          FM[3] := CHANNEL;
335          FM[4] := 0 ;
336          FM[5] := 4;
337
338          RATE := SMPLRATE;
339
340          COPYSTR( '&', OPSTR);
341          WHILE AGAIN AND THEN
342             PROMPTI( ROWSS, 1, 'Samples to average ? ', AVECNT, GE1LE64)
343          DO BEGIN
344             COUNT := AVECNT;
345
346             WHILE AGAIN AND THEN
347                PROMPTI( ROWPR, 1, 'Center count ? ', CTRCNT, GE0LE4095)
348             DO BEGIN
349                CH := ' ';
350                WRITEP( ROWCT, 1, 'ADC average:');
351                WRITEPCU( 24, 1, 'Center /Quit');
352                CLRLINE( ROWAN, 1);
353                CLRLINE( ROWAN+1, 1);
354                WRITEPC( ROWAN+1, 1, SCALE);
355                FOR I := -3 TO 3
356                DO BEGIN
357                   POSCURS( ROWAN+2, (I*10+37));
358                   WRITE( (CTRCNT+I*10):4);
359                   END;
360                OLDTIM := ORD( TICS);
361                COL := 0;
362                REPEAT
363                   IF OLDTIM < 50
364                   THEN BEGIN
365                      REPEAT
366                         CURTIM := ORD( TICS);
367                         UNTIL CURTIM >= 50;
368                      END
369                   ELSE BEGIN
370                      REPEAT
371                         CURTIM := ORD( TICS);
372                         UNTIL CURTIM < 50;
373                      END;
374                   OLDTIM := CURTIM;
375
376                   STATUS := AINFM( FM, COUNT, RATE, RDATA, OPSTR );
377                   IF COL > 0 THEN WRITEP( ROWAN, COL, '.');
378                   TOTAL := RDATA[1];
```

```
379                     FOR I := 2 TO AVECNT DO TOTAL := TOTAL + RDATA[I];
380                     ADCAVE := ROUND( FLOAT( TOTAL) / FLOAT( AVECNT));
381                     COL := ADCAVE - CTRCNT+40;
382                     IF COL < 1 THEN COL := 1
383                         ELSE IF COL > 79 THEN COL := 79;
384                     POSCURS( ROWAN, COL);
385                     WRITE( WHITE, '!', GREEN);
386                     POSCURS( ROWCT, 14);
387                     WRITE( ADCAVE:4);
388                     IF STATUS <> 0 THEN WRITE( '  Error: ', STATUS);
389                     IF CHINPUT THEN CH := GETCHU;
390                    UNTIL (CH = 'Q') OR (CH = 'C');
391                 AGAIN := CH <> 'Q';
392               END;
393            END;
394         END;
395      END;
396   CLR2_25;
397   END;
398
399 PROCEDURE BIN_OUT;
400    CONST
401       HEADING = 'Binary Output Check';
402       ROWCH = 10;
403       ROWAGN = 24;
404
405    VAR
406       CHANNEL, STATUS, I: INTEGER;
407       AGAIN: BOOLEAN;
408       CH: CHAR;
409       OPSTR: STRING(80);
410
411    BEGIN
412    WRITEPC( 1, 30, HEADING);
413    CLR2_25;
414
415    COPYSTR( '&', OPSTR);
416    AGAIN := TRUE;
417    WHILE AGAIN AND THEN
418          PROMPTI( ROWCH, 1, 'Channel ? ', CHANNEL, GEOLE15)
419    DO BEGIN
420       WRITEPCU( 24, 1, 'Channel /H=1 /L=0 /Quit /Toggle');
421
422       CH := GETCHU;
423       I := 0;
424       WHILE (CH <> 'C') AND (CH <> 'Q')
425       DO BEGIN
426
427          IF CH = 'T'
428          THEN IF I = 0 THEN CH := '1' ELSE CH := '0';
429
430          CASE CH OF
431
432          'L','0':
433                  BEGIN
434                  I := 0;
435                  WRITEPC( ROWCH, 20, '0');
436                  STATUS := BITOUS( CHANNEL, I, OPSTR);
437                  END;
438
439          'H','1':
440                  BEGIN
441                  I := 1;
```

```
442                         WRITEPC( ROWCH, 20, '1');
443                         STATUS := BITOUS( CHANNEL, I, OPSTR);
444                         END;
445
446               OTHERWISE STATUS := 0;
447                  END;
448
449               IF STATUS <> 0 THEN WRITE( '  Error: ', STATUS:0);
450               CH := GETCHU;
451               END;
452         AGAIN := CH <> 'Q';
453         END;
454      CLR2_25;
455      END;
456
457  PROCEDURE ADC_MONITOR;
458
459      CONST
460         ESC = CHR( 27);
461         N = 10;
462         STATS_COLOR = ESC*'[37m';
463         NORMAL_COLOR = ESC*'[32m';
464
465      VAR
466         I, M: INTEGER;
467         IA, LIA, UIA: ADCNAM;
468         X: REAL;
469         CH: CHAR;
470         SLOPE, OFFSET, ADCCNT: MVVCT;
471         SUMX, SUMX2: MVVCT;
472
473      BEGIN
474   { Initialize before run
475   }
476      EVAL( DATACQ_SETUP( SLOPE, OFFSET));
477      LIA := LOWER( IA);
478      UIA := UPPER( IA);
479
480      CLR2_25;
481      SYNC_NEXT( -1);
482
483      REPEAT
484         WRITE( ' ');
485         FOR IA := LIA TO UIA
486         DO BEGIN
487            CASE IA OF
488            UNCOMP:      WRITE( '  uncomp    ');
489            TAB:         WRITE( '     tab    ');
490            PHOTOCELL:   WRITE( ' photocell  ');
491            CNTR_TC:     WRITE( ' center tc  ');
492            ACT_COMP:    WRITE( '  act comp  ');
493               END;
494            END;
495         WRITELN;
496
497         FOR IA := LIA TO UIA
498         DO BEGIN
499            SUMX[IA] := 0;
500            SUMX2[IA] := 0;
501            END;
502
503         FOR I := 1 TO N
504         DO BEGIN
```

```
505             ADC_SCAN( 1.0, ADCCNT);
506
507             FOR IA := LIA TO UIA
508             DO BEGIN
509                X := ADCCNT[IA];
510                WRITE( X:9:1, '   ');
511                SUMX[IA] := SUMX[IA]+X;
512                SUMX2[IA] := SUMX2[IA]+X*X;
513                END;
514             WRITELN;
515             END;
516
517          WRITE( ST,  ,_COLOR);
518          FOR IA := LIA TO UIA DO WRITE( (SUMX[IA]/N):11:3);
519
520          WRITELN;
521          FOR IA := LIA TO UIA
522          DO WRITE( ( SQRT( ABS( N*SUMX2[IA] - SQR( SUMX[IA])) / (N*(N-1)) ) ):11:3 );
523          WRITELN( NORMAL_COLOR);
524          WRITELN;
525
526          UNTIL CHKESCAPE;
527
528       INITSCRN;
529       END;
530
531 BEGIN
532 END.

1 INTERFACE(1);
  2
  3 UNIT DATACQ( DATACQ_SETUP, PHOTO_SETUP, RECORD_DATA,
  4              SYNC_NEXT, ADC_SCAN, SMPLRATE);
  5
  6 USES PRAMIFAC;
  7
  8 CONST
  9    SMPLRATE = 400;
 10
 11 FUNCTION DATACQ_SETUP( VAR SLOPE, OFFSET: MVVCT): BOOLEAN;
 12 FUNCTION PHOTO_SETUP: BOOLEAN;
 13 FUNCTION RECORD_DATA( VARS OSUDAT: OSUTYP): BOOLEAN;
 14 PROCEDURE SYNC_NEXT( DELAY: REAL);
 15 PROCEDURE ADC_SCAN( RTIME: REAL;  VAR ADCCNT: MVVCT);
 16
 17 BEGIN
 18 END;

1 {$include:'IO\SCREEN.INT'}
  2 {$include:'IO\KEYBRD.INT'}
  3 {$include:'IO\PROMPT.INT'}
  4 {$include:'PRAMIFAC.INT'}
  5 {$include:'CYBRGCAL.INT'}
  6 {$include:'DATACQ.INT'}
  7
  8 IMPLEMENTATION OF DATACQ;
  9
 10 USES SCREEN,
 11      KEYBRD,
 12      PROMPT,
 13      CYBRGCAL,
 14      PRAMIFAC;
 15
```

```
16      CONST
17         LASTFRMT = DATACHNS+DATACHNS+DATACHNS+DATACHNS+1;
18
19      TYPE
20         STR80 = STRING( 80);
21         LSTR80 = LSTRING( 80);
22
23      VAR
24         I, STATUS, SECCNT: INTEGER;
25         OLDTIM, COUNT, RATE: INTEGER4;
26         RVAL: REAL;
27         OPTNULL: STR80;
28         PCFRMT: ARRAY [1..5] OF INTEGER;
29         DACQFRMT: ARRAY[1..LASTFRMT] OF INTEGER;
30         PR: PR_REC;
31         IA: ADCNAM;
32         THE_HEAT: BOOLEAN;
33
34      FUNCTION AINFM( VARS FORMAT: INTEGER;
35                      VARS COUNT, RATE: INTEGER4;
36                      VARS TARGET: INTEGER;
37                      VARS OPTIONS: STR80): INTEGER; EXTERN;
38
39      FUNCTION BITOUS( CONSTS BIT, VAL: INTEGER;
40                       CONSTS OPTIONS: STR80): INTEGER; EXTERN;
41
42      FUNCTION BITINS( CONSTS BIT: INTEGER;
43                       VARS   VAL: INTEGER;
44                       CONSTS OPTIONS: STR80): INTEGER; EXTERN;
45
46      PROCEDURE ENDXQQ; EXTERN;
47
48      PROCEDURE GETTIM( VARS HR, MN, SC, CS: INTEGER); EXTERN;
49
50      PROCEDURE TERMINATE( CONST MESS: LSTR80; CONST STATUS: INTEGER);
51         BEGIN
52         WRITEPC( 25, 1, MESS);
53         IF STATUS <> 0 THEN WRITELN( STATUS:0);
54         ENDXQQ;
55         END;
56
57      FUNCTION CHKESCAPE1: BOOLEAN;
58         CONST ESC = CHR( 27);
59         VAR
60            J, STATUS: INTEGER;
61            CH: CHAR;
62         BEGIN
63         CH := ' ';
64         WHILE (CH <> ESC) AND THEN CHINPUT
65         DO CH := GETCHU;
66         IF CH = ESC
67         THEN BEGIN
68            POSCURS( 22, 1);
69            WRITE( 'Program: ');
70            IF THE_HEAT THEN WRITE( 'IN ') ELSE WRITE( 'OUT');
71
72            WRITE( '   Cyborg: ');
73            STATUS := BITINS( 8, J, OPTNULL);
74            IF STATUS <> 0 THEN TERMINATE( 'insert chk: ', STATUS);
75            IF J = 1 THEN WRITE( 'IN ') ELSE WRITE( 'OUT');
76            WRITELN;
77            END;
78         CHKESCAPE1 := CH = ESC;
79         END;
```

```
80
81  PROCEDURE SYNC_NEXT;
82  {                                                                          }
83  {   This procedure synchronizes events with the system clock.              }
84  {                                                                          }
85  {   Arguments:                                                             }
86  {       DELAY is in seconds.                                               }
87  {                                                                          }
88  {   Initialization:                                                        }
89  {       To set a reference time call with a negative number.               }
90  {       No delay will occur.                                               }
91  {                                                                          }
92  {   Function:                                                              }
93  {       Wait until DELAY seconds have elapsed since the last reference     }
94  {       time. The reference time is updated to the current time mark.      }
95  {       If the time has passed, control returns immediatly.                }
96  {                                                                          }
97  {   Restrictions:                                                          }
98  {       Do not delay for longer than 20000 seconds.                        }
99  {       The system timer actually runs at 18.207 hz.  Maximum error        }
100 {       is -2 and +3 hundreths of a seconds.                               }
101 {                                                                          }
102     VAR
103        HR, MN, SC, FR: INTEGER;
104        CURTIM, TRGTIM: INTEGER4;
105        SYNCED: BOOLEAN;
106
107     BEGIN
108     IF DELAY < 0
109     THEN BEGIN
110        GETTIM( HR, MN, SC, FR);
111        OLDTIM := BYLONG( 0, FR) + 100*( BYLONG( 0, SC) + 60*( BYLONG( 0, MN)
112                 + 60*BYLONG( 0, HR)) );
113        END.
114     ELSE BEGIN
115        SYNCED := FALSE;
116        TRGTIM := OLDTIM + ROUND4( DELAY*100);
117        REPEAT
118           GETTIM( HR, MN, SC, FR);
119           CURTIM := BYLONG( 0, FR) + 100*( BYLONG( 0, SC) + 60*( BYLONG( 0, MN)
120                    + 60*BYLONG( 0, HR)) );
121           IF CURTIM >= TRGTIM
122           THEN SYNCED := TRUE
123           ELSE IF (CURTIM < 2000000) AND (TRGTIM > 6640000)
124              THEN BEGIN
125                 SYNCED := (CURTIM+8640000) >= TRGTIM;
126                 IF SYNCED THEN TRGTIM := TRGTIM - 8640000;
127                 END;
128           UNTIL SYNCED;
129        OLDTIM := TRGTIM;
130        END;
131     END;
132
133 PROCEDURE ABS_DELAY( DELAY: REAL);
134    VAR
135        DELCNT, I, TMP, SC, FR, OSC, OFR: INTEGER;
136    BEGIN
137    DELCNT := ROUND( DELAY*18.207);
138    IF DELAY < 1 THEN DELCNT := DELCNT+1;
139    GETTIM( TMP, TMP, OSC, OFR);
140    FOR I := 1 TO DELCNT
141    DO BEGIN
```

```
142      REPEAT
143         GETTIM( TMP, TMP, SC, FR);
144         UNTIL (SC <> OSC) OR (FR <> OFR);
145      OSC := SC;
146      OFR := FR;
147      END;
148   END;
149
150
151 FUNCTION DATACQ_SETUP;
152 {                                                                        }
153 {  This procedure must be called before PHOTOCELL or RECORD_DATA  }
154 {                                                                        }
155    VAR
156       CHANS_OK: BOOLEAN;
157       CAL: CALREC;
158
159    BEGIN
160    GET_PARAM( PR);
161    CHANS_OK := TRUE;
162
163    PCFRMT[1] := -1;  { set to zero if photocell calibrated }
164    WITH PR
165    DO BEGIN
166       RATE := SMPLRATE;
167       COUNT := AVECNT;
168
169       I := 1;
170       FOR IA := LOWER( IA) TO UPPER( IA)
171       DO BEGIN
172          CAL := GET_CYCAL( ADCDEV[ IA], ADCCHN[ IA]);
173          IF CAL.DEVICE = -1
174          THEN CHANS_OK := FALSE
175          ELSE BEGIN
176             OFFSET[IA] := CAL.OFFSET;
177             SLOPE[IA] := CAL.SLOPE;
178             DACQFRMT[I  ] := 0;
179             DACQFRMT[I+1] := ADCDEV[ IA];
180             DACQFRMT[I+2] := ADCCHN[ IA];
181             DACQFRMT[I+3] := 0;
182             IF IA = PHOTOCELL
183             THEN BEGIN
184                PCFRMT[1] := 0;
185                PCFRMT[2] := ADCDEV[ IA];
186                PCFRMT[3] := ADCCHN[ IA];
187                PCFRMT[4] := 0;
188                END;
189             I := I+4;
190             END;
191          END;
192       DACQFRMT[I] := 4;
193       PCFRMT[5] := 4;
194
195       END;
196
197    COPYSTR( '& ', OPTNULL);
198    DATACQ_SETUP := CHANS_OK;
199    END;
200
201
202 FUNCTION PHOTO_SETUP;
203    VAR TMP: MVVCT;
```

```
204      BEGIN
205      IF DATACQ_SETUP( TMP, TMP)
206      THEN PHOTO_SETUP := TRUE
207      ELSE PHOTO_SETUP := PCFRMT[1] = 0;
208      END;
209
210   PROCEDURE INSERT_SPEC;   { Move specimen into chamber }
211      VAR
212         STATUS: INTEGER;
213
214      BEGIN
215      WRITEPC( 24, 1, 'Open');
216      STATUS := BITOUS( PR.BOTCHN[OPEN_DOOR], 1, OPTNULL);
217      IF STATUS <> 0 THEN TERMINATE( 'insert_spec:bot1:status: ', STATUS);
218
219      ABS_DELAY( PR.OPNINS);
220
221      THE_HEAT := TRUE;
222      WRITE( ' > Insert');
223      STATUS := BITOUS( PR.BOTCHN[INSERT], 1, OPTNULL);
224      IF STATUS <> 0 THEN TERMINATE( 'insert_spec:bot2:status: ', STATUS);
225
226      ABS_DELAY( PR.INSCLS);
227
228      WRITE( ' > Close');
229      STATUS := BITOUS( PR.BOTCHN[OPEN_DOOR], 0, OPTNULL);
230      IF STATUS <> 0 THEN TERMINATE( 'insert_spec:bot3:status: ', STATUS);
231      END;
232
233   PROCEDURE REMOVE_SPEC;   { Remove specimen from chamber }
234      VAR
235         STATUS: INTEGER;
236
237      BEGIN
238      WRITEPC( 24, 1, 'Open');
239      STATUS := BITOUS( PR.BOTCHN[OPEN_DOOR], 1, OPTNULL);
240      IF STATUS <> 0 THEN TERMINATE( 'remove_spec:bot1:status: ', STATUS);
241
242      ABS_DELAY( PR.OPNRMV);
243
244      WRITE( ' > Remove');
245      STATUS := BITOUS( PR.BOTCHN[INSERT], 0, OPTNULL);
246      IF STATUS <> 0 THEN TERMINATE( 'remove_spec:bot2:status: ', STATUS);
247
248      ABS_DELAY( PR.RMVCLS);
249
250      WRITE( ' > Close');
251      STATUS := BITOUS( PR.BOTCHN[OPEN_DOOR], 0, OPTNULL);
252      IF STATUS <> 0 THEN TERMINATE( 'remove_spec:bot3:status: ', STATUS);
253      THE_HEAT := FALSE;
254      END;
255
256   PROCEDURE ADC_SCAN;
257      VAR
258         STATUS, J: INTEGER;
259         CHN: ADCNAM;
260         TOTAL: INTEGER4;
261         RTMP : REAL;
262         RDATA: ARRAY [1..MAXAVG,ADCNAM] OF INTEGER;
263
264      BEGIN
265
```

```
266 { Get data at beginning of next time interval
267 }
268     STATUS := AINFM( DACQFRMT[1], COUNT, RATE, RDATA[1,LOWER(CHN)], OPTNULL );
269     IF STATUS <> 0
270     THEN BEGIN
271        WRITEPC( 25, 1, 'Labsoft error: ');
272        WRITE( STATUS:0);
273        END;
274
275 { Process current point by channel
276 }
277     RTMP := FLOAT4( COUNT);
278     FOR CHN := LOWER( CHN) TO UPPER( CHN)
279     DO BEGIN
280        TOTAL := RDATA[ 1, CHN];
281        FOR J := 2 TO PR.AVECNT DO TOTAL := TOTAL + RDATA[ J, CHN];
282        ADCCNT[ CHN] := FLOAT4( TOTAL) / RTMP;
283        END;
284
285     SYNC_NEXT( RTIME);
286     END;
287
288 FUNCTION RECORD_DATA;
289 { This procedure records one data run }
290
291     LABEL 86;   { operator abort exit }
292
293     VAR
294        I, J: INTEGER;
295        DATA_OK: BOOLEAN;
296        CHN: ADCNAM;
297        RTMP: REAL;
298        ADCCNT, ADCPNT: MVVCT;
299
300     BEGIN
301     DATA_OK := FALSE;
302     THE_HEAT := FALSE;
303
304     WITH PR
305     DO BEGIN
306
307 { Init
308 }
309        SYNC_NEXT( -1);
310
311 { Hold before average *******************************************
312 }
313        WRITEPC( 24, 1, 'Hold');
314        SECCNT := HOLDTIME;
315        J := HOLDTIME - AVRGTIME;
317        FOR I := 1 TO J
318        DO BEGIN
319           POSCURS( 24, 9);
320           WRITE( SECCNT:3);
321           SECCNT := SECCNT-1;
322           IF CHKESCAPE1 THEN GOTO 86;
323           SYNC_NEXT( 1.0);
324           END;
325
326 { Setup for time 0 average ****************************************
327 }
328        FOR CHN := LOWER( CHN) TO UPPER( CHN) DO ADCCNT[ CHN] := 0;
```

```
{ Start time 0 average
}
      WRITEPC( 24, 1, 'Average');
      FOR I := 1 TO AVRGTIME
      DO BEGIN IF CHKESCAPE1 THEN GOTO 86;
          POSCURS( 24, 9);
          WRITE( SECCNT:3);
          SECCNT := SECCNT-1;

{ Get current seconds data at beginning of next second
}
          ADC_SCAN( 1.0, ADCPNT);

{ Process current second by channel
}
          FOR CHN := LOWER( CHN) TO UPPER( CHN)
          DO ADCCNT[ CHN] := ADCCNT[ CHN] + ADCPNT[CHN];

END;

{ Process time 0 data
}
      RTMP := FLOAT( AVRGTIME );
      FOR CHN := LOWER( CHN) TO UPPER( CHN)
      DO OSUDAT[ 0, CHN] := ROUND( ADCCNT[ CHN] / RTMP);

{ Insert sample ******************************************
}
      IF CHKESCAPE1 THEN GOTO 86;
      INSERT_SPEC;
      SYNC_NEXT( -1);

{ Lets make some crispy critters ******************************
}
      SECCNT := BURNTIME;

{ Aquire burn data
}
      WRITEPC( 24, 1, 'Burn');
      FOR I := 1 TO BURNTIME
      DO BEGIN { Get current seconds data at beginning of next second
}
          IF CHKESCAPE1 THEN GOTO 86;
          POSCURS( 24, 9);
          WRITE( SECCNT:3);
          SECCNT := SECCNT-1;
          ADC_SCAN( 1.0, ADCCNT);

{ Process current second by channel
}
          FOR CHN := LOWER( CHN) TO UPPER( CHN)
          DO OSUDAT[ I, CHN] := ROUND( ADCCNT[CHN]);

END;

{ Remove specimen.  This meatloaf seems to be burned! **********
}
```

```
391         DATA_OK := TRUE;
392         REMOVE_SPEC;
393         END;
394
395 86:
396     IF THE_HEAT
397     THEN BEGIN
398         WRITEPC( 24, 1, 'Press Enter when ready to remove sample');
399         WHILE GETCH <> CHR( 13) DO;
400         SYNC_NEXT( -1);
401         REMOVE_SPEC;
402         END;
403     RECORD_DATA := DATA_OK;
404     CLRLINE( 22, 1);
405     END;
406
407 BEGIN
408 THE_HEAT := FALSE;
409 END.

1 INTERFACE(1);
2
3 UNIT DATAIFAC( SUBRUNSIZ, DAT_IFAC, CHK_SUBRUNSIZ,
4                STORE_RUN, RUN_EXISTS, DELETE_RUN, LOAD_HDR, LOAD_RUN,
5                DP_COMPAT, RUN_COMPAT);
6
7 USES PRAMIFAC, PHOTOCAL;
8
9 CONST
10    SUBRUNSIZ = 25;
11
12 TYPE
13    DAT_IFAC = RECORD
14        CASE BOOLEAN OF
15            FALSE:(
16                { Work request, Material, Specimens, Specimen type }
17                WR_NUMBER: WRSTR;
18                MATERIAL: MATSTR;
19                SPCCNT: INTEGER;
20                SPCTYP: CHAR;
21                RUN_DUMMY: FILNAMTYP;
22
23                { ADC samples to average }
24                AVECNT: INTEGER;
25
26                { mV conversions and photocell calibration info }
27                SLP, OFS: MVVCT;
28                PC: PC_REC;
29
30                { Run event times }
31                HOLDTIME, AVRGTIME, BURNTIME: INTEGER;
32
33                { Other run variables }
34                HEATFLUX, QK_COMP, QK_UNCOMP, VFLOW, SRFCAREA, TINLET: REAL;
35                UNCOMP_CNT: INTEGER;
36                YR, MO, DA: INTEGER;
37                );
38
39            TRUE: (
40                SUBRUN: ARRAY [0..SUBRUNSIZ-1] OF ADCTYP;
41                );
42            END;
43
```

```
44 PROCEDURE CHK_SUBRUNSIZ;
45
46 FUNCTION RUN_EXISTS( FILNAM: FILNAMTYP): BOOLEAN;
47
48 PROCEDURE DELETE_RUN( FILNAM: FILNAMTYP);
49
50 PROCEDURE STORE_RUN( CONST  PR: PR_REC;
51                      CONSTS DATA: OSUTYP;
52                      VAR    SLOPE, OFFSET: MVVCT;
53                             FILNAM: FILNAMTYP);
54
55 PROCEDURE LOAD_HDR( FILNAM: FILNAMTYP;  VAR HDR: DAT_IFAC);
56
57 PROCEDURE LOAD_RUN( FILNAM: FILNAMTYP;  SPC: INTEGER;
58                     VARS DATA: MVMAT);
59
60 PROCEDURE DP_COMPAT( CONST A, B: DAT_IFAC;
61                      VAR   COMPAT, IDENT, LENGTH: BOOLEAN);
63 PROCEDURE RUN_COMPAT( CONST A: PR_REC;
64                       CONST DMYNAM: FILNAMTYP;
65                       VAR   DMYFND, COMPAT, IDENT, LENGTH: BOOLEAN);
66
67 BEGIN
68 END;

1 {$include:'IO\KEYBRD.INT'}
 2 {$include:'IO\SCREEN.INT'}
 3 {$include:'PRAMIFAC.INT'}
 4 {$include:'PHOTOCAL.INT'}
 5 {$include:'DATAIFAC.INT'}
 6 {$include:'IBMINTRP.INT'}
 7
 8 IMPLEMENTATION OF DATAIFAC;
 9
10 USES SCREEN,
11      IBMINTRP,
12      KEYBRD,
13      PRAMIFAC,
14      PHOTOCAL;
15
16 PROCEDURE GETDAT( VARS YR, MO, DA: INTEGER); EXTERN;
17
18 PROCEDURE ENDXQQ; EXTERN;
19
20 {$include:'FILEERRS.PAS'}
21
22 PROCEDURE ERRCHK( ERR: WORD;  FILNAM: FILNAMTYP;  CONST WHERE: LSTRING);
23    BEGIN
24    IF ERR <> 0
25    THEN BEGIN
26        CLRLINE( 23, 1);
27        WRITE( 'file: ', FILNAM, '  where: ', WHERE);
28        FILE_ERRS( ERR);
29        END;
30    END;
31
32 PROCEDURE CHK_SUBRUNSIZ;
33    VAR
34       I: INTEGER;
35       A: DAT_IFAC;
36       B: ADCTYP;
37       W: WORD;
38    BEGIN
```

```
39      IF SIZEOF( A) > (SIZEOF( B) * SUBRUNSIZ)
40      THEN BEGIN
41         W := SIZEOF( B);
42         I := ORD( ( SIZEOF( A) + W-1)) DIV ORD( W);
43         WRITEPC( 24, 1, 'SUBRUNSIZ in DATAIFAC is to small, must be >= ');
44         WRITELN( I:0);
45         ENDXQQ;
46         END;
47      END;
48
49
50  PROCEDURE DELETE_RUN;
51     VAR
52        REGS: REGLIST;
53
54     BEGIN
55     CONCAT( FILNAM, CHR( 0));
56     REGS.DS := (ADS FILNAM[1]).S;
57     REGS.DX := (ADS FILNAM[1]).R;
58     REGS.AX := BYWORD( #41,#00);
59     INTRP( #21, REGS, REGS);
60     END;
61
62
63  FUNCTION RUN_EXISTS;
64     VAR
65        RFILE: FILE OF DAT_IFAC;
66
67     BEGIN
68     ASSIGN( RFILE, FILNAM);
69     RFILE.TRAP := TRUE;
70     RFILE.ERRS := 0;
71     RFILE.MODE := SEQUENTIAL;
72     RESET( RFILE);
73     RUN_EXISTS := RFILE.ERRS = FLOK;
74     CLOSE( RFILE);
75     END;
76
77
78  PROCEDURE STORE_RUN;
79     VAR
80        I, J: INTEGER;
81        RFILE: FILE OF DAT_IFAC;
82        R: DAT_IFAC;
83
84     BEGIN
85     IF RUN_EXISTS( FILNAM) <> (PR.SPCCNT > 1)
86     THEN BEGIN
87        WRITEPC( 25, 1, 'Program error detected in store_run.');
88        WRITE  ( ' ', FILNAM, '  ', RUN_EXISTS( FILNAM), ' ', PR.SPCCNT);
89        ENDXQQ;
90        END;
91
92  { Go for it!
93  }
94     ASSIGN( RFILE, FILNAM);
95     RFILE.TRAP := TRUE;
96     RFILE.ERRS := 0;
97     IF PR.SPCCNT = 1 THEN RFILE.MODE := SEQUENTIAL ELSE RFILE.MODE := DIRECT;
98     REWRITE( RFILE);
99
100    IF PR.SPCCNT > 1
101    THEN BEGIN
```

```
102         SEEK( RFILE, 1);
103         ERRCHK( RFILE.ERRS, FILNAM, 'store_run.seek1');
104         GET( RFILE);
105         ERRCHK( RFILE.ERRS, FILNAM, 'store_run.get1');
106         R := RFILE^;
107         END;
108
109     WITH PR
110     DO BEGIN
111        R.SPCCNT := SPCCNT;
112        IF SPCCNT = 1
113        THEN BEGIN
114           R.WR_NUMBER := WR_NUMBER;
115           R.MATERIAL := MATERIAL;
116           R.SPCTYP := SPCTYP;
117           R.RUN_DUMMY := RUN_DUMMY;
118           R.SLP := SLOPE;
119           R.OFS := OFFSET;
120           GET_PC( R.PC);
121           R.HOLDTIME := HOLDTIME;
122           R.AVRGTIME := AVRGTIME;
123           R.BURN_ME := BURNTIME;
124           R.HEATFLUX := HEATFLUX;
125           R.QK_COMP := QK_COMP;
126           R.QK_UNCOMP := QK_UNCOMP;
127           R.VFLOW := VFLOW;
128           R.SRFCAREA := SRFCAREA;
129           R.TINLET := TINLET;
130           R.UNCOMP_CNT := UNCOMP_CNT;
131           GETDAT( R.YR, R.MO, R.DA);
132           R.YR := R.YR MOD 100;
133           END;
134        END;
135
136     IF R.SPCCNT > 1 THEN SEEK( RFILE, 1);
137     RFILE^ := R;
138     PUT( RFILE);
139     ERRCHK( RFILE.ERRS, FILNAM, 'store_run.put.hdr');
140
141     IF PR.SPCCNT > 1
142     THEN WITH PR DO SEEK( RFILE,
143        ( ((BURNTIME+1 + SUBRUNSIZ-1) DIV SUBRUNSIZ) * (SPCCNT-1) + 2) );
144     ERRCHK( RFILE.ERRS, FILNAM, 'store_run.seek2');
145
146     J := -1;
147     FOR I := 0 TO PR.BURNTIME
148     DO BEGIN
149        J := J+1;
150        IF J >= SUBRUNSIZ
151        THEN BEGIN
152           RFILE^ := R;
153           PUT( RFILE);
154           ERRCHK( RFILE.ERRS, FILNAM, 'store_run.put.data');
155           J := 0;
156           END;
157        R.SUBRUN[J] := DATA[I];
158        END;
159     RFILE^ := R;
160     PUT( RFILE);
161     ERRCHK( RFILE.ERRS, FILNAM, 'store_run.put.last');
162
163     CLOSE( RFILE);
164     ERRCHK( RFILE.ERRS, FILNAM, 'store_run.close');
165     END;
```

```
166
167
168 PROCEDURE LOAD_HDR;
169    VAR
170       RFILE: FILE OF DAT_IFAC;
171
172    BEGIN
173    ASSIGN( RFILE, FILNAM);
174    RFILE.TRAP := TRUE;
175    RFILE.ERRS := 0;
176    RFILE.MODE := DIRECT;
177    RESET( RFILE);
178    ERRCHK( RFILE.ERRS, FILNAM, 'load_hdr.reset');
179    SEEK( RFILE, 1);
180    ERRCHK( RFILE.ERRS, FILNAM, 'load_hdr.seek');
181    GET( RFILE);
182    ERRCHK( RFILE.ERRS, FILNAM, 'load_hdr.get');
183    HDR := RFILE^;
184    CLOSE( RFILE);
185    END;
186
187
188 PROCEDURE LOAD_RUN;
189    VAR
190       I, J, BURNTIME: INTEGER;
191       IA: ADCNAM;
192       RFILE: FILE OF DAT_IFAC;
193       R: DAT_IFAC;
194       ADC: ADCTYP;
195       MV, SLP, OFS: MVVCT;
196
197    BEGIN
198    ASSIGN( RFILE, FILNAM);
199    RFILE.TRAP := TRUE;
200    RFILE.ERRS := 0;
201    RFILE.MODE := DIRECT;
202    RESET( RFILE);
203
204    SEEK( RFILE, 1);
205    ERRCHK( RFILE.ERRS, FILNAM, 'load_run.seek.1');
206    GET( RFILE);
207    ERRCHK( RFILE.ERRS, FILNAM, 'load_run.get.1');
208    R := RFILE^;
209    BURNTIME := R.BURNTIME;
210    SLP := R.SLP;
211    OFS := R.OFS;
212    SEEK( RFILE,
213       ( ((BURNTIME+1 + SUBRUNSIZ-1) DIV SUBRUNSIZ) * (SPC-1) + 2) );
214    ERRCHK( RFILE.ERRS, FILNAM, 'load_run.seek.i');
215    J := SUBRUNSIZ;
216    FOR I := 0 TO BURNTIME
217    DO BEGIN
218       J := J+1;
219       IF J >= SUBRUNSIZ
220       THEN BEGIN
221          GET( RFILE);
222          ERRCHK( RFILE.ERRS, FILNAM, 'load_run.get.data');
223          R := RFILE^;
224          J := 0;
225          END;
226       ADC := R.SUBRUN[J];
227       FOR IA := LOWER( IA) TO UPPER( IA)
228          DO MV[IA] := ADC[IA]*SLP[IA] + OFS[IA];
```

```
229        DATA[I] := MV;
230        END;
231
232     CLOSE( RFILE);
233     END;
234
235 PROCEDURE DP_COMPAT;
236     BEGIN
237 {
238     Is the configuration of a dummy file compatable with a run file?
239     NOTE: Compatability is not reflexive:
240           (A compat B) does not mean (B compat A)
241 }
242     IF (A.HEATFLUX   = B.HEATFLUX  ) AND THEN
243        (A.SPCTYP     = B.SPCTYP    ) AND THEN
244        (A.QK_UNCOMP  = B.QK_UNCOMP ) AND THEN
245        (A.QK_COMP    = B.QK_COMP   ) AND THEN
246        (A.UNCOMP_CNT = B.UNCOMP_CNT) AND THEN
247        (A.HOLDTIME   = B.HOLDTIME  ) AND THEN
248        (A.AVRGTIME   = B.AVRGTIME  )
249     THEN BEGIN
250        IDENT  := A.BURNTIME = B.BURNTIME;
251        COMPAT := TRUE;
252        LENGTH := A.BURNTIME <= B.BURNTIME;
253        END
254     ELSE BEGIN
255        IDENT  := FALSE;
256        COMPAT := FALSE;
257        LENGTH := A.BURNTIME <= B.BURNTIME;
258        END;
259     END;
260
261 PROCEDURE RUN_COMPAT;
262     VAR
263        B: DAT_IFAC;
264     BEGIN
265 {
266     Is the configuration of a dummy file compatable with a run file?
267     NOTE: Compatability is not reflexive:
268           (A compat B) does not mean (B compat A)
269 }
270     DMYFND := RUN_EXISTS( DMYNAM);
271     IF DMYFND
272     THEN BEGIN
273        LOAD_HDR( DMYNAM, B);
274        IF (A.HEATFLUX   = B.HEATFLUX  ) AND THEN
275           (A.SPCTYP     = B.SPCTYP    ) AND THEN
276           (A.QK_UNCOMP  = B.QK_UNCOMP ) AND THEN
277           (A.QK_COMP    = B.QK_COMP   ) AND THEN
278           (A.UNCOMP_CNT = B.UNCOMP_CNT) AND THEN
279           (A.HOLDTIME   = B.HOLDTIME  ) AND THEN
280           (A.AVRGTIME   = B.AVRGTIME  )
281        THEN BEGIN
282           IDENT  := A.BURNTIME = B.BURNTIME;
283           COMPAT := TRUE;
284           LENGTH := A.BURNTIME <= B.BURNTIME;
285           END
286        ELSE BEGIN
287           IDENT  := FALSE;
288           COMPAT := FALSE;
289           LENGTH := A.BURNTIME <= B.BURNTIME;
290           END;
291        END;
292     END;
```

```
293
294 BEGIN
295 END.

1 INTERFACE(0);
  2
  3 UNIT DATAPROC( DATPRC, REPORT);
  4
  5 USES PRAMIFAC;
  6
  7 PROCEDURE REPORT( PR: PR_REC;  FILNAM: FILNAMTYP);
  8 PROCEDURE DATPRC( VAR PR_IN: PR_REC);
  9
 10 BEGIN
 11 END;

1 {$include:'\OSUDV\IO\SCREEN.INT'}
  2 {$include:'\OSUDV\IO\KEYBRD.INT'}
  3 {$include:'\OSUDV\IO\PROMPT.INT'}
  4 {$include:'\OSUDV\PRAMIFAC.INT'}
  5 {$include:'\OSUDV\PHOTOCAL.INT'}
  6 {$include:'\OSUDV\DATAIFAC.INT'}
  7 {$include:'\OSUDV\HARDWARE.INT'}
  8 {$include:'\OSUDV\SETUP.INT'}
  9 {$include:'\OSUDV\DATACQ.INT'}
 10 {$include:'\OSUDV\LS\LESTSQAR.INT'}
 11 {$include:'DATAPROC.INT'}
 12
 13 IMPLEMENTATION OF DATAPROC;
 14
 15 USES SCREEN,
 16      KEYBRD,
 17      PROMPT,
 18      DATAIFAC,
 19      HARDWARE,
 20      PRAMIFAC,
 21      SETUP,
 22      DATACQ,
 23      LESTSQAR;
 24
 25 CONST
 26     LEMAXSEC = VALBND( 0, LE, MAXSEC);
 27     FGTOLEMAXRUNNO = FVALBND( 0.0, GTLE, FMAXRUNNO);
 28     ABSZERO = 273.16;
 29
 30 TYPE
 31     RSLTVCT = ARRAY [1..MAXTIMX+2] OF REAL;
 32     RSLTMAT = ARRAY [1..MAXSPC] OF RSLTVCT;
 33     STR5 = STRING( 5);
 34
 35 { These var entries are inited by init_heat and smoke_init }
 36 VAR
 37     BURNTIME, SPCCNT, UNCOMP_CNT, PC_DEGR: INTEGER;
 38     SMPLO, DMMYO, QK: REAL;
 39     VFLOW, TINLET, SRFCAREA, SMOK0, SMOK1, SMOK2, SMOK3: REAL;
 40     HEAT_COMP, SMOK_CNTR: BOOLEAN;
 41     PC_COEF: VECTOR;
 42
 43 FUNCTION LDSRQQ( CONSTS P: REAL4): REAL4; EXTERN;
 44
 45 FUNCTION MMSS( T: INTEGER): STR5;
 46     VAR
 47         I, S: INTEGER;
 48         TSTR: STR5;
```

```
49   BEGIN
50   S := T DIV 60;
51   TSTR := ' 0:00';
52   FOR I := 2 DOWNTO 1
53   DO BEGIN
54      IF S > 0 THEN TSTR[I] := CHR( 48 + S MOD 10);
55      S := S DIV 10;
56      END;
57   S := T MOD 60;
58   FOR I := 5 DOWNTO 4
59   DO BEGIN
60      TSTR[I] := CHR( 48 + S MOD 10);
61      S := S DIV 10;
62      END;
63   MMSS := TSTR;
64   END;
65
66
67 PROCEDURE INIT_RELS( CONST RUNCND: DAT_IFAC;
68                     CONST PR: PR_REC);
69    VAR
70       I: INTEGER;
71       XV, YV: VECTOR;
72       ERR: BOOLEAN;
73
74    BEGIN
75    BURNTIME := RUNCND.BURNTIME;
76    SPCCNT := RUNCND.SPCCNT;
77
78    HEAT_COMP := PR.HEAT_COMP;
79    IF HEAT_COMP
80    THEN QK := RUNCND.QK_COMP
81    ELSE QK := RUNCND.QK_UNCOMP;
82
83    SMOK_CNTR := PR.SMOK_CNTR;
84    UNCOMP_CNT := RUNCND.UNCOMP_CNT;
85    VFLOW := RUNCND.VFLOW;
86    SRFCAREA := RUNCND.SRFCAREA;
87    TINLET := RUNCND.TINLET;
88
89    SMOK1 := VFLOW*1000.0 / (SRFCAREA*13.335);
90    SMOK2 := 24.5098;
91    IF NOT SMOK_CNTR THEN SMOK2 := SMOK2 / FLOAT( UNCOMP_CNT);
92    SMOK3 := TINLET + ABSZERO;
93
94    PC_DEGR := 3;
95    FOR I := 1 TO RUNCND.PC.FILTERS
96    DO BEGIN
97       XV[I] := RUNCND.PC.FLTRVOLT[I];
98       YV[I] := RUNCND.PC.FILTER[I];
99       END;
100   LSTSQR( RUNCND.PC.FILTERS, PC_DEGR, XV, YV, PC_COEF, ERR);
101   IF ERR THEN WRITEPC( 1, 1, 'LSTSQR error');
102   END;
103
104 FUNCTION PPOLY( X: REAL): REAL;
105    VAR
106       I: INTEGER;
107       Y: REAL;
108    BEGIN
109    Y := 0;
110    FOR I := PC_DEGR+1 DOWNTO 1
111    DO Y := Y*X + PC_COEF[I];
```

```
112     PPOLY := Y;
113     END;
114
115 FUNCTION DQDT( CONSTS DMMY, SMPL: MVVCT): REAL;
116     BEGIN
117     IF HEAT_COMP
118     THEN DQDT := QK*( (SMPL[UNCOMP]-SMPL[TAB] - SMPL0) -
119                       (DMMY[UNCOMP]-DMMY[TAB] - DMMY0) )
120     ELSE DQDT := QK*( (SMPL[UNCOMP] - SMPL0) - (DMMY[UNCOMP] - DMMY0) );
121     END;
122
123 FUNCTION DDSDT( CONSTS SMPL: MVVCT): REAL;
124     VAR
125        SMOKLOG: REAL;
126     BEGIN
127     SMOKLOG := PPOLY( SMPL[ PHOTOCELL]);
128     IF SMOKLOG = 0 THEN SMOKLOG := 1E6;
129     SMOKLOG := SMOK0 / SMOKLOG;
130     IF SMOKLOG <= 0 THEN SMOKLOG := 1;
131     SMOKLOG := LDSRQQ( SMOKLOG);
132     IF SMOK_CNTR
133     THEN DDSDT := SMOK1*SMOKLOG*( (SMOK2*SMPL[TAB] + ABSZERO) / SMOK3)
134     ELSE DDSDT := SMOK1*SMOKLOG*( (SMOK2*SMPL[UNCOMP] + SMOK3) / SMOK3);
135     END;
136
137 PROCEDURE HEAT_RELS( CONSTS DMMY, SMPL: MVMAT;
138                      CONST  TIME: TIMVCT;
139                      VAR    Q: RSLTVCT);
140     VAR
141        T, TIMX, MAXDQDTTIM: INTEGER;
142        QT, QTOT, MAXDQDT: REAL;
143
144     BEGIN
145     DMMY0 := DMMY[0,UNCOMP];
146     SMPL0 := SMPL[0,UNCOMP];
147     IF HEAT_COMP
148     THEN BEGIN
149        DMMY0 := DMMY0 - DMMY[0,TAB];
150        SMPL0 := SMPL0 - SMPL[0,TAB];
151        END;
152
153     T := 1;
154     TIMX := 1;
155     MAXDQDT := DQDT( DMMY[T], SMPL[T]);
156     MAXDQDTTIM := T;
157     QTOT := MAXDQDT * 0.5;
158     T := T+1;
159     WHILE T <= BURNTIME
160     DO BEGIN
161        QT := DQDT( DMMY[T], SMPL[T]);
162        IF QT > MAXDQDT
163        THEN BEGIN
164           MAXDQDT := QT;
165           MAXDQDTTIM := T;
166           END;
167
168        IF T = TIME[TIMX]
169        THEN BEGIN
170           Q[TIMX] := (QTOT + QT*0.5) / 60.0;
171           TIMX := TIMX+1;
172           END;
173
174        IF T = BURNTIME
```

```
175        THEN QTOT := QTOT + QT*0.5
176        ELSE QTOT := QTOT + QT;
177
178        T := T+1;
179        END;
180     Q[TIMX] := MAXDQDT;
181     Q[TIMX+1] := FLOAT( MAXDQDTTIM);
182     END;
183
184
185  PROCEDURE SMOK_RELS( CONSTS SMPL: MVMAT;
186                       CONST  TIME: TIMVCT;
187                       VAR    DS: RSLTVCT);
188     VAR
189        T, TIMX, MAXDDSDTTIM: INTEGER;
190        DST, DSTOT, MAXDDSDT: REAL;
191
192     BEGIN
193     SMOK0 := PPOLY( SMPL[0,PHOTOCELL]);
194
195     T := 1;
196     TIMX := 1;
197     MAXDDSDT := DDSDT( SMPL[T]);
198     MAXDDSDTTIM := T;
199     DSTOT := MAXDDSDT * 0.5;
200     T := T+1;
201     WHILE T <= BURNTIME
202     DO BEGIN
203        DST := DDSDT( SMPL[T]);
204        IF DST > MAXDDSDT
205        THEN BEGIN
206           MAXDDSDT := DST;
207           MAXDDSDTTIM := T;
208           END;
209
210        IF T = TIME[TIMX]
211        THEN BEGIN
212           DS[TIMX] := DSTOT + DST*0.5;
213           TIMX := TIMX+1;
214           END;
215
216        IF T = BURNTIME
217        THEN DSTOT := DSTOT + DST*0.5
218        ELSE DSTOT := DSTOT + DST;
219
220        T := T+1;
221        END;
222     DS[TIMX] := MAXDDSDT;
223     DS[TIMX+1] := FLOAT( MAXDDSDTTIM);
224     END;
225
226
227  PROCEDURE PRINT_REPORT( CONST  FILNAM, USE_DUMMY: FILNAMTYP;
228                          CONST  PR: PR_REC;
229                          CONST  HDR: DAT_IFAC;
230                                 COMPAT: BOOLEAN;
231                          VAR    Q, DS: RSLTMAT);
232
233     CONST
234        ESC = CHR( 27);
235        SPS = ESC*'S0';
236        SBS = ESC*'S1';
237        NOS = ESC*'T';
```

```
238       SQRD = '²' {sps*'2'*nos};
239       DEGR = '°' {sps*'o'*nos};
240       DSUBS = 'D'*SBS*'s'*NOS;
241       UNDON = ESC*'-1';
242       UNDOFF = ESC*'-0';
243       HEAT_W = 7;   { width of heat field column }
244       SMOK_W = 7;   { width of smoke field column }
245
246    VAR
247       I, SPC, SPCA, T, TIMX, TUSD: INTEGER;
248       TMP: REAL;
249       TSTR: LSTRING( 30);
250       PRN: TEXT;
251
252    BEGIN
253    ASSIGN( PRN, 'PRN:');
254    REWRITE( PRN);
255    WITH HDR
256    DO BEGIN
257
258    WRITE   ( PRN, CHR( 12), '            ');
259    WRITELN( PRN, 'BMT   -   Ohio State University Apparatus Data Analyzer',
260                              '    -   5E6896A00');
261    WRITELN( PRN);
262
263                  {123456789a123456789b123456789c123456789d123456789e}
264
265    WRITE   ( PRN, 'Radiant Heat Flux    ', HEATFLUX:7:2, ' W/cm', SQRD, '
);
266    WRITELN( PRN, 'Work Request No: ', WR_NUMBER);
267
268    IF HEAT_COMP
269    THEN BEGIN
270       TMP := QK_COMP;
271       TSTR := 'Compensated';
272       END
273    ELSE BEGIN
274       TMP := QK_UNCOMP;
275       TSTR := 'Uncompensated';
276       END;
277    WRITE   ( PRN, 'Calibration Constant ', TMP:7:2,     ' kW/mV/m', SQRD,
278                       '           ');
279    WRITELN( PRN, 'Material:        ', MATERIAL);
280
281    WRITE   ( PRN, 'Temperature at Inlet ', TINLET:5:0, '   ', DEGR, 'C
);
282    WRITE   ( PRN, 'Run No:         ', FILNAM);
283    WRITELN( PRN, '  (', MO:0, '-', DA:0, '-', YR:0, ')');
284
285    WRITE   ( PRN, 'Volumetric Air Flow  ', VFLOW:6:1, '  1/sec              ');
286    WRITE   ( PRN, 'Blank No:       ', USE_DUMMY);
287    IF COMPAT THEN WRITELN( PRN) ELSE WRITELN( PRN, ' *INCOMPATIBLE*');
288
289    WRITE   ( PRN, 'Exposed Surface Area ', SRFCAREA:7:2, ' cm', SQRD, '
);
290
291    WRITELN( PRN, 'Comp or Uncomp:  ', TSTR);
292    IF SMOK_CNTR
293    THEN WRITE   ( PRN, '                                                       ',
294                    '                   (smoke - 1 tc)');
295    WRITELN( PRN);
296    WRITELN( PRN);
297
```

```
298 { Find number of columns to printed in heat report }
299   TUSD := 0;
300   FOR TIMX := 1 TO MAXTIMX
301   DO BEGIN
302      T := PR.HEAT_RPT[TIMX];
303      IF (T > 0) AND (T <= BURNTIME) THEN TUSD := TIMX;
304      END;
305
306 { Center heading as well as possible }
307   WRITE  ( PRN, '         ');
308   TSTR := 'Total Heat Release (Q)';
309   I := TUSD*HEAT_W - ORD( TSTR.LEN);
310   IF (I > 0) AND ODD( I) THEN WRITE  ( PRN, ' ');
311   I := I DIV 2;
312   FOR T := 0 TO I DO WRITE  ( PRN, ' ');
313   WRITE  ( PRN, TSTR);
314   FOR T := 2 TO I DO WRITE  ( PRN, ' ');
315   WRITELN( PRN, '    Heat Release Rate');
316
317   WRITE  ( PRN, '         ');
318   TSTR := 'kW-min/m'*SQRD;
319   I := TUSD*HEAT_W - 9;
320   IF (I > 0) AND ODD( I) THEN WRITE  ( PRN, ' ');
321   I := I DIV 2;
322   FOR T := 0 TO I DO WRITE  ( PRN, ' ');
323   WRITE  ( PRN, TSTR);
324   FOR T := 2 TO I DO WRITE  ( PRN, ' ');
325   WRITELN( PRN, '         (dQ/dt)');
326
327   WRITELN( PRN);
328   WRITE  ( PRN, UNDON, 'Spec#', UNDOFF, ' ', UNDON);
329   FOR TIMX := 1 TO TUSD DO
330      WRITE  ( PRN, UNDON, MMSS( PR.HEAT_RPT[TIMX]), UNDOFF, '  ');
331   WRITE  ( PRN, ' ', UNDON, 'Peak kW/m', SQRD, UNDOFF, '  ');
332   WRITELN( PRN, UNDON, 'Peak Time', UNDOFF);
333
334   FOR SPCA := 1 TO SPCCNT+1
335   DO BEGIN
336
337      IF SPCA = SPCCNT+1
338      THEN BEGIN
339         WRITELN( PRN);
340         WRITE  ( PRN, ' avg ');
341         SPC := 1;
342         FOR TIMX := 1 TO TUSD+2
343         DO Q[1,TIMX] := Q[1,TIMX] / FLOAT( SPCCNT);
344         END
345      ELSE BEGIN
346         SPC := SPCA;
347         WRITE  ( PRN, SPC:3, ' ');
348         END;
349
350      FOR TIMX := 1 TO TUSD DO WRITE  ( PRN, Q[SPC,TIMX]:HEAT_W:2);
351      WRITELN( PRN, Q[SPC,TUSD+1]:11:2, '    ', MMSS( TRUNC( Q[SPC,TUSD+2])));
352
353      IF SPC <> 1
354      THEN BEGIN
355         FOR TIMX := 1 TO TUSD+2
356         DO Q[1,TIMX] := Q[1,TIMX] + Q[SPC,TIMX];
357         END;
358      END;
359   WRITELN( PRN);
360
```

```
361    WRITELN( PRN);
362
363 { Find number of columns to printed in smoke report }
364    TUSD := 0;
365    FOR TIMX := 1 TO MAXTIMX
366    DO BEGIN
367       T := PR.SMOK_RPT[TIMX];
368       IF (T > 0) AND (T <= BURNTIME) THEN TUSD := TIMX;
369       END;
370
371 { Center heading as well as possible }
372    WRITE  ( PRN, '      ');
373    TSTR := 'Total Smoke Release (Ds)';
374    I := TUSD*SMOK_W - ORD( TSTR.LEN);
375    IF (I > 0) AND ODD( I) THEN WRITE  ( PRN, ' ');
376    I := I DIV 2;
377    FOR T := 0 TO I DO WRITE  ( PRN, ' ');
378    WRITE  ( PRN, TSTR);
379    FOR T := 2 TO I DO WRITE  ( PRN, ' ');
380    WRITELN( PRN, '    Smoke Release Rate');
381
382    WRITE  ( PRN, '      ');
383    I := TUSD*SMOK_W;
384    FOR T := 1 TO I DO WRITE  ( PRN, ' ');
385    WRITELN( PRN, '         (dDs/dt)');
386
387    WRITELN( PRN);
388    WRITE  ( PRN, UNDON, 'Spec#', UNDOFF, ' ', UNDON);
389    FOR TIMX := 1 TO TUSD DO
390       WRITE  ( PRN, UNDON, MMSS( PR.SMOK_RPT[TIMX]), UNDOFF, ' ');
391    WRITE  ( PRN, ' ', UNDON, 'Peak 1/sec', UNDOFF, ' ');
392    WRITELN( PRN, UNDON, 'Peak Time', UNDOFF);
393
394    FOR SPCA := 1 TO SPCCNT+1
395    DO BEGIN
396
397       IF SPCA = SPCCNT+1
398       THEN BEGIN
399          WRITELN( PRN);
400          WRITE  ( PRN, ' avg ');
401          SPC := 1;
402          FOR TIMX := 1 TO TUSD+2
403          DO DS[1,TIMX] := DS[1,TIMX] / FLOAT( SPCCNT);
404          END
405       ELSE BEGIN
406          SPC := SPCA;
407          WRITE  ( PRN, SPC:3, ' ');
408          END;
409
410       FOR TIMX := 1 TO TUSD DO WRITE  ( PRN, DS[SPC,TIMX]:SMOK_W:2);
411       WRITELN( PRN, DS[SPC,TUSD+1]:11:2, '      ', MMSS( TRUNC( DS[SPC,TUSD+2])));
412
413       IF SPC <> 1
414       THEN BEGIN
415          FOR TIMX := 1 TO TUSD+2
416          DO DS[1,TIMX] := DS[1,TIMX] + DS[SPC,TIMX];
417          END;
418       END;
419    WRITELN( PRN);
420
421    END;
422    WRITELN( PRN, CHR( 12));
423    CLOSE( PRN);
424    END;
```

```
425
426 FUNCTION GETMQQ( X: WORD): ADSMEM; EXTERN;
427
428 PROCEDURE DISMQQ( BLOCK: ADSMEM); EXTERN;
429
430 PROCEDURE CHK_RUN(    RUNNAM, DP_DUMMY: FILNAMTYP;
431                   VAR RUNFND, DMYFND, COMPAT, LENGTH: BOOLEAN);
432    VAR
433       USE_DUMMY: FILNAMTYP;
434       A, B: DAT_IFAC;
435       IDENT: BOOLEAN;
436
437    BEGIN
438    RUNFND := RUN_EXISTS( RUNNAM);
439    IF RUNFND
440    THEN BEGIN
441       LOAD_HDR( RUNNAM, A);
442
443       IF DP_DUMMY = NULL
444       THEN USE_DUMMY := A.RUN_DUMMY
445       ELSE USE_DUMMY := DP_DUMMY;
446
447       IF USE_DUMMY = 'ZERO DUMMY'
448       THEN BEGIN
449          DMYFND := TRUE;
450          LENGTH := TRUE;
451          COMPAT := TRUE;
452          END
453       ELSE BEGIN
454          DMYFND := RUN_EXISTS( USE_DUMMY);
455          IF DMYFND
456          THEN BEGIN
457             DMYFND := TRUE;
458             LOAD_HDR( USE_DUMMY, B);
459             DP_COMPAT( A, B, COMPAT, IDENT, LENGTH);
460             END;
461          END;
462       END;
463    END;
464
465 PROCEDURE REPORT;
466    VAR
467       SPC: INTEGER;
468       Q, DS: RSLTMAT;
469       RUNCND, DMYCND: DAT_IFAC;
470       PSMPL, PDMMY: ADS OF MVMAT;
471       USE_DUMMY: FILNAMTYP;
472       RUNFND, DMYFND, COMPAT, LENGTH: BOOLEAN;
473
474    PROCEDURE ZEROMAT( VARS DATA: MVMAT);
475       VAR
476          I: INTEGER;
477          IA: ADCNAM;
478          TMP: MVVCT;
479       BEGIN
480       FOR IA := LOWER( IA) TO UPPER( IA) DO TMP[IA] := 0;
481       FOR I := 0 TO RUNCND.BURNTIME DO DATA[I] := TMP;
482       END;
483
484    BEGIN
485    CHK_RUN( FILNAM, PR.DP_DUMMY, RUNFND, DMYFND, COMPAT, LENGTH);
486    IF RUNFND AND DMYFND AND LENGTH
487    THEN BEGIN
```

```
488        WRITEPC( 24, 1, 'Processing: ');
489        WRITE( FILNAM);
490        PDMMY := GETMQQ( SIZEOF( PDMMY^));
491        PSMPL := GETMQQ( SIZEOF( PSMPL^));
492        LOAD_HDR( FILNAM, RUNCND);
494        INIT_RELS( RUNCND, PR);
495
496        IF PR.DP_DUMMY = NULL
497        THEN USE_DUMMY := RUNCND.RUN_DUMMY
498        ELSE USE_DUMMY := PR.DP_DUMMY;
499
500        IF USE_DUMMY = 'ZERO DUMMY'
501        THEN BEGIN
502           ZEROMAT( PDMMY^);
503           COMPAT := TRUE;
504           END
505        ELSE BEGIN
506           LOAD_HDR( USE_DUMMY, DMYCND);
507           LOAD_RUN( USE_DUMMY, 1, PDMMY^);
508           END;
509
510        FOR SPC := 1 TO RUNCND.SPCCNT
511        DO BEGIN
512           LOAD_RUN( FILNAM, SPC, PSMPL^);
513           HEAT_RELS( PDMMY^, PSMPL^, PR.HEAT_RPT, Q[SPC]);
514           SMOK_RELS( PSMPL^, PR.SMOK_RPT, DS[SPC]);
515           END;
516
517        DISMQQ( PSMPL);
518        DISMQQ( PDMMY);
519        PRINT_REPORT( FILNAM, USE_DUMMY, PR, RUNCND, COMPAT, Q, DS);
520
521        CLRLINE( 24, 1);
522        END;
523     END;
524
525  PROCEDURE RUN_RANGE( CONST PR: PR_REC);
526     VAR
527        LINCNT: INTEGER;
528        RUN, RUNBEG, RUNEND: INTEGER4;
529        RTMP: REAL;
530        CH, RUNCH: CHAR;
531        FILNAM: FILNAMTYP;
532        VC: FVALBND;
533        ERR, FIRST, RUNFND, DMYFND, COMPAT, LENGTH: BOOLEAN;
534
535     BEGIN
536     CLR2_25;
537     WRITEP( 24, 1, 'Run prefix (A..Z) ? ');
538     REPEAT
539        CH := GETCHU;
540        UNTIL (CH = CHR(13)) OR ELSE ((CH >= 'A') AND (CH <= 'Z'));
541     IF CH <> CHR(13)
542     THEN BEGIN
543        RUNCH := CH;
544        IF PROMPTR( 24, 1, 'Beginning run number ? ', RTMP,
545                    FGTOLEMAXRUNNO)
546        THEN BEGIN
547           RUNBEG := TRUNC4( RTMP);
548           VC := FVALBND( 0.0, GELE, FMAXRUNNO);
549           VC.LOWBND := FLOAT4( RUNBEG);
550           IF PROMPTR( 24, 1, 'Ending run number ? ', RTMP, VC)
551           THEN BEGIN
```

```
552         RUNEND := TRUNC4( RTMP);
553         IF RUNEND-RUNBEG > 99
554         THEN BEGIN
555            RUNEND := RUNBEG+99;
556            WRITEPC( 25, 1, 'Run range truncated to ');
557            WRITE( RUNEND:0);
558            END;
559         FIRST := TRUE;
560         RUN := RUNBEG;
561         LINCNT := 99;
562         WHILE RUN <= RUNEND
563         DO BEGIN
564            FILNAM := RUNFILNAM( RUNCH, RUN);
565            CHK_RUN( FILNAM, PR.DP_DUMMY, RUNFND, DMYFND, COMPAT, LENGTH);
566            ERR := NOT( RUNFND AND DMYFND AND COMPAT AND LENGTH);
567            IF ERR
568            THEN BEGIN
569               IF LINCNT >= 20
570               THEN BEGIN
571                  IF FIRST
572                  THEN FIRST := FALSE
573                  ELSE BEGIN
574                     WRITEPCU( 25, 1, 'More...');
575                     REPEAT CH := GETCHU; UNTIL CH = 'M';
576                     END;
577                  CLR2_25;
578                  POSCURS( 3, 1);
579                  LINCNT := 0;
580                  END;
581               WRITE( FILNAM, ': ');
582               IF NOT RUNFND
583               THEN WRITELN( 'Run not found - omitted')
584               ELSE IF NOT DMYFND
585               THEN WRITELN( 'Dummy not found - omitted')
586               ELSE IF NOT LENGTH
587               THEN WRITELN( 'Dummy is to short for run - omitted')
588               ELSE IF NOT COMPAT
589               THEN WRITELN( 'Dummy incompatible -- will process');
590               LINCNT := LINCNT + 1;
591               END;
592            RUN := RUN + 1;
593            END;
594         IF NOT FIRST
595         THEN BEGIN
596            WRITEPC( 24, 1, 'Do you wish to continue ');
597            WRITEU( '(Y/N) ? ');
598            REPEAT CH := GETCHU UNTIL (CH = 'Y') OR (CH = 'N');
599            FIRST := CH = 'Y';
600            END;
601         IF FIRST
602         THEN BEGIN
603            CLR2_25;
604            WRITEP( 23, 1, 'Type ESC to stop');
605            RUN := RUNBEG;
606            WHILE RUN <= RUNEND
607            DO BEGIN
608               FILNAM := RUNFILNAM( RUNCH, RUN);
609               REPORT( PR, FILNAM);
610               IF CHKESCAPE THEN RUN := RUNEND;
611               RUN := RUN + 1;
612               END;
613            END;
614         END;
```

```
615           END;
616         END;
617     END;
618
619
620 PROCEDURE DSP_DATPRC( CONST PR: PR_REC);
621     VAR
622         I, ROW, TIMX: INTEGER;
623         NSTR: ADCSTRTYP;
624
625     BEGIN
626     CLR2_25;
627
628     WITH PR
629     DO BEGIN
630         ROW := 3;
631         WRITEPU( ROW, 1, 'Dummy: ');
632         IF DP_DUMMY.LEN > 0
633         THEN BEGIN
634             WRITE( DP_DUMMY);
635             IF (DP_DUMMY <> 'ZERO DUMMY')
636             THEN IF NOT RUN_EXISTS( DP_DUMMY) THEN WRITE( ERRFG*' *NOT FOUND*'*NORMFG):
637             END
638         ELSE WRITE( 'per run');
639
640         ROW := ROW + 2;
641         CLRLINE( ROW, 1);
642         IF NOT HEAT_COMP THEN WRITE( 'un');
643         WRITEU( 'Compensated');
644
645         ROW := ROW + 2;
646         WRITEPU( ROW, 1, 'sMoke calculation uses ');
647         IF SMOK_CNTR
648         THEN WRITE( 'center TC')
649         ELSE WRITE( 'uncompensated TCs');
650
651         ROW := ROW + 2;
652         WRITEP( ROW, 1, 'Result times by report');
653         ROW := ROW + 1;
654         WRITEPU( ROW, 1, '  Heat: ');
655         FOR TIMX := 1 TO MAXTIMX
656         DO BEGIN
657             IF HEAT_RPT[TIMX] > 0 THEN WRITE( ' ', MMSS( HEAT_RPT[TIMX]));
658             END;
659         ROW := ROW + 1;
660         WRITEPU( ROW, 1, '  smOke:');
661         FOR TIMX := 1 TO MAXTIMX
662         DO BEGIN
663             IF SMOK_RPT[TIMX] > 0 THEN WRITE( ' ', MMSS( SMOK_RPT[TIMX]));
664             END;
665
666         END;
667     END;
668
669 PROCEDURE DATPRC;
670     CONST
671         HEADING = 'Data Processing';
672
673     VAR
674         I: INTEGER;
675         DONE, UPDATE: BOOLEAN;
676         RUNFND, DMYFND, COMPAT, LENGTH: BOOLEAN;
677         RTMP: REAL;
```

```
678         CH: CHAR;
679         TSTR: GLSTRTYP;
680         FILNAM: FILNAMTYP;
681         TMPBND: VALBND;
682         PR: PR_REC;
683
684      PROCEDURE UPDTIM( VAR TIM: TIMVCT);
685         VAR
686            TIMX, TIMMIN, TIME: INTEGER;
687            PSTR: LSTRING( 80);
688         BEGIN
689         WRITEPC( 23, 1, 'Up to ');
690         WRITE( MAXTIMX:0, ' strictly ascending times may be entered.  Terminate list wit
   h a -1.');
691         PSTR := 'Time #1 in seconds ? ';
692         TIMMIN := 1;   { Min time must be > 1 else messy code }
693         TIME := 1;
694         FOR TIMX := 1 TO MAXTIMX
695         DO BEGIN
696            PSTR[7] := CHR( 48 + TIMX);
697            REPEAT
698               UPDATEI( 24, 1, PSTR, TIM[TIMX], LEMAXSEC);
699               UNTIL (TIM[TIMX] = -1) OR ELSE (TIM[TIMX] > TIMMIN);
700            IF TIM[TIMX] < 0 THEN BREAK;
701            TIMMIN := TIM[TIMX];
702            TIME := TIMX+1;
703            END;
704         FOR TIMX := TIME TO MAXTIMX DO TIM[TIMX] := -1;
705         END;
706
707      BEGIN
708      PR := PR_IN;
709
710      DONE := FALSE;
711      UPDATE := TRUE;
712      REPEAT
713         WRITEPC( 1, 30, HEADING);
714         IF UPDATE THEN DSP_DATPRC( PR) ELSE UPDATE := TRUE;
715         WRITEPC( 24, 1, 'COMMAND: ');
716         WRITEU( 'Range /Single report /Quit ? ');
717         CH := GETCHU;
718         CLRLINE( 25, 1);
719         CASE CH OF
720
721         'C':  PR.HEAT_COMP := NOT PR.HEAT_COMP;
722
723         'D':  BEGIN
724               IF PROMPTL( 24, 1, 'Alternate dummy file name ? ', TSTR)
725               THEN BEGIN
726                  TRIM( TSTR);
727                  LWRUPR( TSTR);
728                  IF TSTR.LEN > 0 THEN PR.DP_DUMMY := TSTR;
729                  END
730               ELSE PR.DP_DUMMY := NULL;
731               END;
732
733         'H':  UPDTIM( PR.HEAT_RPT);
734
735         'M':  PR.SMOK_CNTR := NOT PR.SMOK_CNTR;
736
737         'O':  UPDTIM( PR.SMOK_RPT);
738
739         'Q':  DONE := TRUE;
```

```
740
741            'R':   RUN_RANGE( PR);
742
743            'S':   BEGIN
744                   IF PROMPTL( 24, 1, 'Run number to process ? ', TSTR)
745                   THEN BEGIN
746                       TRIM( TSTR);
747                       LWRUPR( TSTR);
748                       FILNAM := TSTR;
749                       CHK_RUN( FILNAM, PR.DP_DUMMY, RUNFND,'DMYFND, LENGTH, COMPAT);
750                       UPDATE := RUNFND AND DMYFND AND LENGTH;
751                       IF UPDATE
752                       THEN REPORT( PR, FILNAM)
753                       ELSE BEGIN
754                           IF NOT RUNFND
755                           THEN BEGIN
756                               WRITEPC( 25, 1, 'Run does not exist: ');
757                               WRITE( FILNAM);
758                               END
759                           ELSE IF NOT DMYFND THEN WRITEPC( 25, 1, 'Dummy does not exist')
760                           ELSE IF NOT LENGTH THEN WRITEPC( 25, 1, 'Dummy to short for run');
761                           END;
762                       END;
763                   END;
764
765            OTHERWISE
766                   BEGIN
767                   WRITEPC( 25, 1, 'Unknown Command');
768                   UPDATE := FALSE;
769                   END;
770
771            END;
772
773         UNTIL DONE;
774
775     CLR2_25;
776     PUT_PARAM( PR);
777     PR_IN := PR;
778     END;
779
780 BEGIN
781 END.
  1 INTERFACE(0);
  2
  3 UNIT DUMMYCAL( DUMMY_CAL);
  4
  5 USES PRAMIFAC;
  6
  7 FUNCTION DUMMY_CAL( PR: PR_REC): BOOLEAN;
  8
  9 BEGIN
 10 END;
```

APPENDIX TO SPECIFICATION

Part II of II

```
1  {$include:'IO\SCREEN.INT'}
2  {$include:'IO\KEYBRD.INT'}
3  {$include:'IO\PROMPT.INT'}
4  {$include:'PRAMIFAC.INT'}
5  {$include:'PHOTOCAL.INT'}
6  {$include:'DATAIFAC.INT'}
7  {$include:'DATACQ.INT'}
8  {$include:'DUMMYCAL.INT'}
9
10 IMPLEMENTATION OF DUMMYCAL;
11
12 USES SCREEN,
13      KEYBRD,
14      PROMPT,
15      DATAIFAC,
16      DATACQ,
17      PRAMIFAC;
18
19 CONST
20    CR = CHR( 13);
21    ESC = CHR( 27);
22    GEOLE99 = VALBND( 0, GELE, 99);
23
24
25 FUNCTION DUMMY_CAL;
26 {                                                        }
27 {  Make one or more dummy runs and store data            }
28 {                                                        }
29    LABEL
30       86;   { Abort via escape }
31
32    CONST
33       HEADING = 'Dummy Calibration';
34
35    VAR
36       I, SPEC: INTEGER;
37       IA: ADCNAM;
38       SAVED, EXISTS: BOOLEAN;
39       RTMP: REAL;
40       CH: CHAR;
41       FILNAM: FILNAMTYP;
42       TSTR4: LSTRING( 4);
43       DMYRUN: OSUTYP;
44       DMYTOT: ARRAY [0..MAXSEC,ADCNAM] OF INTEGER4;
45       SLP, OFS: MVVCT;
46
47    FUNCTION NAME_DMYFIL( SEQ: INTEGER): FILNAMTYP;
48    {                                                     }
49    { Form dummy file name: DMfnn[.NS]                    }
50    {    where: f is the heatflux character               }
51    {           nn is a sequence number                   }
52    {           .NS means non standard                    }
53    {                                                     }
54       VAR
55          I, N: INTEGER;
56          CH: CHAR;
57          TSTR, NAME: LSTRING( 14);
58
59       BEGIN
60       NAME := 'DM';
```

```
61      TSTR := ' ';
62      TSTR[1] := PR.RUNPRFX;
63      CONCAT( NAME, TSTR);
64
65      TSTR := '00';
66      N := SEQ;
67      FOR I := 2 DOWNTO 1
68      DO BEGIN
69         TSTR[I] := CHR( ORD('0') + N MOD 10);
70         N := N DIV 10;
71         END;
72      CONCAT( NAME, TSTR);
73      IF (PR.SPCTYP <> ' ') OR (PR.BURNTIME < 300)
74      THEN CONCAT( NAME, '.NS');
75      NAME_DMYFIL := NAME;
76      END;
77
78    BEGIN
79  { Initialize before run
80  }
81      IF NOT DATACQ_SETUP( SLP, OFS)
82      THEN BEGIN
83         WRITEPC( 25, 1, 'Not all channels calibrated');
84         DUMMY_CAL := FALSE;
85         GOTO 86;
86         END;
87
88      WRITEPC( 1, 30, HEADING);
89
90      FOR I := 0 TO PR.BURNTIME
91      DO FOR IA := LOWER( IA) TO UPPER( IA)
92         DO DMYTOT[I,IA] := 0;
93
94  { Sum each specimen
95  }
96      SPEC := 1;
97      WHILE SPEC <= PR.DMYCNT
98      DO BEGIN
99         WRITEPC( 24, 1, 'Insert Dummy Specimen ');
100        WRITE( SPEC:0, ' and hit ENTER to start run');
101        REPEAT
102           CH := GETCH;
103           DUMMY_CAL := TRUE;
104           IF CH = ESC THEN GOTO 86;
105           UNTIL CH = CR;
106        CLRLINE( 24, 1);
107
108        IF RECORD_DATA( DMYRUN)
109        THEN BEGIN
110           CLRLINE( 24, 1);
111           FOR I := 0 TO PR.BURNTIME
112           DO FOR IA := LOWER( IA) TO UPPER( IA)
113              DO DMYTOT[I,IA] := DMYTOT[I,IA] + DMYRUN[I,IA];
114           SPEC := SPEC+1;
115           END;
116        END;
117
118 { Compute average of runs minus the zero time
119 }
120     RTMP := FLOAT( PR.DMYCNT);
121     FOR I := 0 TO PR.BURNTIME
122     DO FOR IA := LOWER( IA) TO UPPER( IA)
123        DO DMYRUN[I,IA] := ROUND( FLOAT4( DMYTOT[I,IA] - DMYTOT[0,IA])/ RTMP);
```

```
124
125 { Store the dummy run
126 }
127    PR.WR_NUMBER := 'Dummy Calibration';
128    PR.MATERIAL := 'none';
129    PR.SPCCNT := 1;
130
131    SAVED := FALSE;
132    WHILE (NOT SAVED) AND THEN
133          PROMPTI( 24, 1, 'Dummy file sequence number (ENTER to discard) ? ',
134                I, GEOLE99)
135    DO BEGIN
136       FILNAM := NAME_DMYFIL( I);
137       EXISTS := RUN_EXISTS( FILNAM);
138       IF EXISTS
139       THEN BEGIN
140          WRITEPC( 25, 1, 'Dummy file exists: ');
141          WRITE( FILNAM, '.  Overwrite ');
142          WRITEU( '(Y/N) ?');
143          REPEAT CH := GETCHU UNTIL (CH = 'Y') OR (CH = 'N' );
144          CLRLINE( 25, 1);
145          IF CH = 'Y'
146          THEN BEGIN
147             DELETE_RUN( FILNAM);
148             EXISTS := FALSE;
149             END;
150          END;
151
152       IF NOT EXISTS
153       THEN BEGIN
154          STORE_RUN( PR, DMYRUN, SLP, OFS, FILNAM);
155          SAVED := TRUE;
156          END;
157       END;
158
159    DUMMY_CAL := TRUE;
160 86: { were outa here }
161    END;
162
163
164 BEGIN
165 END.

1 INTERFACE(0);
 2
 3 UNIT HARDWARE( UPD_HRDWAR);
 4
 5 PROCEDURE UPD_HRDWAR;
 6
 7 BEGIN
 8 END;

1 {$include:'IO\SCREEN.INT'}
 2 {$include:'IO\KEYBRD.INT'}
 3 {$include:'IO\PROMPT.INT'}
 4 {$include:'PRAMIFAC.INT'}
 5 {$include:'CYBRGCAL.INT'}
 6 {$include:'HARDWARE.INT'}
 7
 8 IMPLEMENTATION OF HARDWARE;
 9
10 USES SCREEN,
11      KEYBRD,
12      PROMPT,
```

```
13        PRAMIFAC,
14        CYBRGCAL;
15
16 CONST
17     FDLYBND = FVALBND( 0.0, GELT, 20.0);
18     GEOLE7  = VALBND( 0, GELE, 7);
19     GEOLE15 = VALBND( 0, GELE, 15);
20     GTOLE64 = VALBND( 0, GELE, 64);
21
22 VAR
23     PR: PR_REC;
24
25 PROCEDURE DSP_HRDWAR( CONST PR: PR_REC);
26     VAR
27        I, ROW, ROW2: INTEGER;
28        IA: ADCNAM;
29        IB: BOTNAM;
30        NSTR: ADCSTRTYP;
31        CR: CALREC;
32
33     BEGIN
34     CLR2_25;
35
36     WITH PR
37     DO BEGIN
38        ROW := 3;
39        WRITEPU( ROW, 1, 'Door seq times:  open ');
40        WRITE( OPNINS:0:1, ' insert ', INSCLS:0:1, ' close...open ', OPNRMV:0:1,
41               ' remove ', RMVCLS:0:1, ' close');
42
43        ROW := ROW + 2;
44        WRITEPU( ROW, 1, 'adc Samples to average: ');
45        WRITE( AVECNT:0);
46
47        ROW := ROW + 2;
48        ROW2 := ROW;
49        WRITEP( ROW, 1, ' Analog sig  Slot Chan    Cal');
50        FOR IA := LOWER( IA) TO UPPER( IA)
51        DO BEGIN
52           ROW := ROW + 1;
53           NSTR := NAME_ADC( IA);
54           WRITEPU( ROW, 1, NSTR);
55           POSCURS( ROW, 16);
56           WRITE( ADCDEV[IA]:1, ADCCHN[IA]:6);
57           POSCURS( ROW, 25);
58           CR := GET_CYCAL( ADCDEV[IA], ADCCHN[IA]);
59           WITH CR
60           DO IF DEVICE = -1
61              THEN WRITE( 'none')
62              ELSE WRITE( YR:0, '/', MO:0, '/', DA:0);
63           END;
64
65        WRITEP( ROW2, 40, ' Digital sig  Chan');
66        FOR IB := LOWER( IB) TO UPPER( IB)
67        DO BEGIN
68           ROW2 := ROW2 + 1;
69           NSTR := NAME_BOT( IB);
70           WRITEPU( ROW2, 40, NSTR);
71           POSCURS( ROW2, 55);
72           WRITE( BOTCHN[IB]:3);
73           END;
74
75        END;
76     END;
```

```
 77
 78   PROCEDURE UPD_HRDWAR;
 79      CONST
 80         HEADING = 'Hardware Configuration';
 81
 82      VAR
 83         I: INTEGER;
 84         IA1, IA2: ADCNAM;
 85         IB1, IB2: BOTNAM;
 86         DONE, UPDATE, ERR: BOOLEAN;
 87         RTMP: REAL;
 88         CH: CHAR;
 89         PSTR: LSTRING(80);
 90         TMPBND: VALBND;
 91         PR: PR_REC;
 92
 93      PROCEDURE UPDADC( CONST IA: ADCNAM);
 94         VAR
 95            NSTR: ADCSTRTYP;
 96            TSTR: LSTRING( 30);
 97         BEGIN
 98         NSTR := NAME_ADC( IA);
 99         TSTR := NSTR;
100         CONCAT( TSTR, ' slot ? ');
101         UPDATEI( 24, 1, TSTR, PR.ADCDEV[ IA], GEOLE7);
102         TSTR := NSTR;
103         CONCAT( TSTR, ' channel ? ');
104         UPDATEI( 24, 1, TSTR, PR.ADCCHN[ IA], GEOLE15);
105         END;
106
107      PROCEDURE UPDBOT( CONST IB: BOTNAM);
108         VAR
109            TSTR: LSTRING( 30);
110            NSTR: ADCSTRTYP;
111         BEGIN
112         NSTR := NAME_BOT( IB);
113         TSTR := NSTR;
114         CONCAT( TSTR, ' channel ? ');
115         UPDATEI( 24, 1, TSTR, PR.BOTCHN[ IB], GEOLE15);
116         END;
117
118      BEGIN
119      GET_PARAM( PR);
120
121      DONE := FALSE;
122      UPDATE := TRUE;
123      REPEAT
124         WRITEPC( 1, 30, HEADING);
125         IF UPDATE THEN DSP_HRDWAR( PR) ELSE UPDATE := TRUE;
126         WRITEPC( 24, 1, 'COMMAND: ');
127         WRITEU( 'Bin out /Cal chan /Monitor adc /Quit /Raw chan ? ');
128         CH := GETCHU;
129         CLRLINE( 25, 1);
130         CASE CH OF
131
132         'A':  UPDADC( ACT_COMP);
133
134         'B':  BIN_OUT;
135
136         'C':  CAL_CHAN;
137
138         'D':  BEGIN
139               UPDATER( 24, 1, 'Open - Insert delay (sec) ? ', PR.OPNINS, FDLYBND);
```

```
140              UPDATER( 24, 1, 'Insert - Close delay (sec) ? ', PR.INSCLS, FDLYBND);
141              UPDATER( 24, 1, 'Open - Remove delay (sec) ? ', PR.OPNRMV, FDLYBND);
142              UPDATER( 24, 1, 'Remove - Close delay (sec) ? ', PR.RMVCLS, FDLYBND);
143              END;
144
145     'I':  UPDBOT( INSERT);
146
147     'M':  ADC_MONITOR;
148
149     'N':  UPDADC( CNTR_TC);
150
151     'O':  UPDBOT( OPEN_DOOR);
152
153     'P':  UPDADC( PHOTOCELL);
154
155     'R':  RAW_CHAN;
156
157     'S':  UPDATEI( 24, 1, 'ADC Samples to average ? ', PR.AVECNT, GTOLE64);
158
159     'T':  UPDADC( TAB);
160
161     'U':  UPDADC( UNCOMP);
162
163     'Q':  BEGIN
164           DONE := TRUE;
165
166 {         Now check for error conditions before allowing exit
167 }
168           POSCURS( 25, 1);
169           ERR := FALSE;
170           FOR IA1 := LOWER( IA1) TO PRED (UPPER( IA1))
171           DO FOR IA2 := SUCC( IA1) TO UPPER( IA2)
172              DO WITH PR
173                 DO IF ( ADCDEV[IA1] = ADCDEV[IA2]) AND
174                       ( ADCCHN[IA1] = ADCCHN[IA2])
175                    THEN ERR := TRUE;
176           IF ERR
177           THEN BEGIN
178              WRITE( 'Duplicate analog channels. ');
179              DONE := FALSE;
180              END;
181
182           ERR := FALSE;
183           FOR IB1 := LOWER( IB1) TO PRED (UPPER( IB1))
184           DO FOR IB2 := SUCC( IB1) TO UPPER( IB2)
185              DO WITH PR
186                 DO IF BOTCHN[IB1] = BOTCHN[IB2]
187                    THEN ERR := TRUE;
188           IF ERR
189           THEN BEGIN
190              WRITE( 'Duplicate digital channels. ');
191              DONE := FALSE;
192              END;
193
194           IF NOT DONE
195           THEN BEGIN
196              WRITE( 'Must be exclusive.');
197              UPDATE := FALSE;
198              END;
199           END;
201     OTHERWISE
202           BEGIN
203           WRITEPC( 25, 1, 'Unknown Command');
204           UPDATE := FALSE;
```

```
205            END;
206
207         END;
208
209      IF UPDATE THEN PUT_PARAM( PR);
210
211      UNTIL DONE;
212
213   CLR2_25;
214   END;
215
216 BEGIN
217 END.
  1 INTERFACE(3);
  2
  3 UNIT KEYBRD( GETCH, GETCHU, CHINPUT, GLSTRTYP, GETLSTR, CLRTYPAHD, CHKESCAPE,
  4              LWRUPR, TRIM);
  5
  6 TYPE
  7    GLSTRTYP = LSTRING(79);
  8
  9 FUNCTION GETCH: CHAR;
 10 FUNCTION GETCHU: CHAR; { upper case getch }
 11 FUNCTION CHINPUT: BOOLEAN;
 12 FUNCTION GETLSTR( CONST INITIAL: GLSTRTYP): GLSTRTYP;
 13 PROCEDURE CLRTYPAHD;
 14 FUNCTION CHKESCAPE: BOOLEAN;
 15 PROCEDURE LWRUPR( VAR STR: LSTRING);
 16 PROCEDURE TRIM( VAR STR: LSTRING);
 17
 18 BEGIN
 19 END;
  1 {$include:'KEYBRD.INT'}
  2
  3 IMPLEMENTATION OF KEYBRD;
  4
  5 CONST
  6    MAXLEN = 79;  { maximum input string }
  7    ESC = CHR( 27);
  8    CURSSAVE = ESC*'[s';
  9    CURSRSTR = ESC*'[u';
 10
 11 TYPE
 12    CHSET = SET OF CHAR;
 13
 14 VAR
 15    DATE: INTEGER;
 16    FILEC: FILE OF CHAR;
 17    ACTSET, SIGSET: CHSET;
 18
 19 PROCEDURE ENDXQQ; EXTERN;
 20
 21 FUNCTION DOSXQQ( W1, W2: WORD): BYTE; EXTERN;
 22
 23 PROCEDURE GETDAT( VARS YR, MO, DA: INTEGER); EXTERN;
 24
 25
 26 FUNCTION CHINPUT;
 27    BEGIN
 28    GETDAT( DATE, DATE, DATE);
 29    CHINPUT := DOSXQQ( 16#B, 0) > 0;
 30    END;
 31
```

```
32 PROCEDURE GETC;
33 {
34    This procedure waits for input.  When input is found the file pointer
35    is advanced.  If there is no input, it waits.  The system date is requested
36    between tests for input.  This is done to keep the system clock from loosing
37    a day on the weekend
38 }
39    BEGIN
40    WHILE NOT CHINPUT DO;
41    GET( FILEC);
42    END;
43
44
45 FUNCTION GETCH;
46    BEGIN
47    REPEAT GETC UNTIL FILEC^ <> CHR(0);
48    IF FILEC^ = CHR( 3) THEN ENDXQQ;
49    GETCH := FILEC^;
50    END;
51
52
53 FUNCTION GETCHU;
54    VAR CH: CHAR;
55    BEGIN
56    CH := GETCH;
57    IF (CH >= 'a') AND (CH <= 'z') THEN CH := CHR( ORD( CH) - 32);
58    GETCHU := CH;
59    END;
60
61
62 FUNCTION GETCD: INTEGER;
63    VAR IC: INTEGER;
64    BEGIN
65    GETC;
66    IC := ORD( FILEC^);
67    IF IC = 3 THEN ENDXQQ;
68    IF IC = 0
69    THEN BEGIN
70       GETC;
71       GETCD := 128 + ORD( FILEC^);
72       END
73    ELSE GETCD := IC;
74    END;
75
76 FUNCTION GETLSTR;
77    CONST
78
79       KRBO = 8;   KESC = 27;                         { [  8]  [esc]                   }
80                   KBEG = 199;                        { [ 13]  [199] [200] [201]       }
81                   KLFT = 203;    KRHT = 205;         { [ 13]  [203] [   ] [205]       }
82                   KEND = 207;                        {        [207] [208] [209]       }
83                   KTGL = 210;    KDEL = 211;         {        [ 210    ] [211]        }
84
85       BACKSPC = CHR(27)*'[D';
86       FORWSPC = CHR(27)*'[C';
87
88    TYPE
89       INSRPL = (RPL,INS);
90
91    VAR
92       IC, P, L, I: INTEGER;
93       MODE: INSRPL;
94       CH: CHAR;
```

```
 95      BUF: LSTRING( MAXLEN);
 96      STR1: STRING(1);
 97
 98   BEGIN
 99   BUF := INITIAL;      { initialize buffer }
100   L := ORD(BUF.LEN);   {             length }
101   P := L+1;            {           position }
102   MODE := RPL;         {               mode }
103   IF L > 0 THEN WRITE( BUF);
104   IC := GETCD;
105   CH := CHR( IC);
106
107   WHILE NOT( CH IN ACTSET)
108   DO BEGIN
109      IF CH IN SIGSET   { print character and update screen }
110      THEN BEGIN
111         IF P > L
112         THEN BEGIN
113            IF P <= MAXLEN
114            THEN BEGIN
115               STR1[1] := CH;
116               CONCAT( BUF, STR1);
117               WRITE( CH);
118               L := L+1;
119               P := P+1;
120               END;
121            END
122         ELSE IF MODE = RPL   { replace mode insertion }
123         THEN BEGIN
124            BUF[P] := CH;
125            WRITE( CH);
126            P := P+1;
127            END
128         ELSE BEGIN           { insert mode insertion }
129            IF L < MAXLEN
130            THEN BEGIN
131               STR1[1] := CH;
132               INSERT( STR1, BUF, P);
133               P := P+1;
134               L := L+1;
135               WRITE( CH);
136               FOR I:=P TO L DO WRITE( BUF[I]);
137               WRITE( CHR(27), '[', (L-P+1):0, 'D');
138               END;
139            END;
140         END
141      ELSE BEGIN  { editing keys }
142         CASE IC OF
143
144         KLFT: BEGIN           { move cursor left }
145               IF P > 1
146               THEN BEGIN
147                  P := P-1;
148                  WRITE( BACKSPC);
149                  END;
150               END;
151
152         KBEG: BEGIN           { move cursor to beginning of line }
153               IF P > 1
154               THEN BEGIN
155                  WRITE( CHR(27), '[', (P-1):0, 'D');
156                  P := 1;
157                  END;
```

```
158             END;
159
160       KESC: BEGIN           { clear input and move to beginning of line }
161             IF P > 1 THEN WRITE( CHR(27), '[', (P-1):0, 'D');
162             FOR I := 1 TO L DO WRITE( ' ');
163             IF L > 0 THEN WRITE( CHR(27), '[', L:0, 'D');
164             L := 0;
165             P := 1;
166             BUF := NULL;
167             END;
168
169       KRHT: BEGIN           { move cursor right }
170             IF P <= L
171             THEN BEGIN
172                P := P+1;
173                WRITE( FORWSPC);
174                END;
175             END;
176
177       KEND: BEGIN           { move cursor to end of line }
178             IF P <= L
179             THEN BEGIN
180                WRITE( CHR(27), '[', (L-P+1):0, 'C');
181                P := L+1;
182                END;
183             END;
184
185                          { toggle insert/replace mode }
186       KTGL: IF MODE = INS THEN MODE := RPL ELSE MODE := INS;
187
188       KDEL: BEGIN           { del character at cusor }
189             IF P <= L
190             THEN BEGIN
191                DELETE( BUF, P, 1);
192                L := L-1;
193                FOR I:=P TO L DO WRITE( BUF[I]);
194                WRITE( ' ');
195                WRITE( CHR(27), '[', (L-P+2):0, 'D');
196                END;
197             END;
199       KRBO: BEGIN           { rubout character left of cusor }
200             IF P > 1
201             THEN BEGIN
202                DELETE( BUF, P-1, 1);
203                L := L-1;
204                P := P-1;
205                WRITE( BACKSPC);
206                FOR I:=P TO L DO WRITE( BUF[I]);
207                WRITE( ' ');
208                WRITE( CHR(27), '[', (L-P+2):0, 'D');
209                END;
210             END;
211
212        OTHERWISE ;
213           END;
214        END;
215     IC := GETCD;
216     CH := CHR( IC);
217     END;
218  WRITE( CHR(27), '[', (P-1):0, 'D');
219  GETLSTR := BUF;
220  END;
221
```

```
222 PROCEDURE CLRTYPAHD;
223    VAR CH: CHAR;
224    BEGIN
225    WHILE CHINPUT DO CH := GETCH;
226    END;
227
228 FUNCTION CHKESCAPE;
229    VAR CH: CHAR;
230    BEGIN
231    CH := ' ';
232    WHILE (CH <> ESC) AND THEN CHINPUT
233    DO CH := GETCH;
234    CHKESCAPE := CH = ESC;
235    END;
236
237 PROCEDURE LWRUPR;
238    VAR
239       I, L: INTEGER;
240       CH: CHAR;
241    BEGIN
242    L := ORD( STR.LEN);
243    FOR I := 1 TO L
244    DO BEGIN
245       CH := STR[I];
246       IF (CH >= 'a') AND (CH <= 'z') THEN STR[I] := CHR( ORD( CH) - 32);
247       END;
248    END;
249
250 PROCEDURE TRIM;
251    VAR
252       I, J: INTEGER;
253    BEGIN
254    J := ORD( STR.LEN);
255    WHILE (J > 0) AND THEN (STR[J] = ' ')
256    DO BEGIN
257       STR.LEN := STR.LEN-1;
258       J := J - 1;
259       END;
260    I := 0;
261    WHILE (I < J) AND THEN (STR[I+1] = ' ')
262    DO I := I + 1;
263    DELETE( STR, 1, I);
264    END;
265
266 BEGIN
267 ASSIGN( FILEC, 'USER');
268 RESET( FILEC);
269 SIGSET := [' '..CHR(127)];
270 ACTSET := [CHR(13)];
271 END.
  1 INTERFACE(1);
  2
  3 UNIT LESTSQAR( MAXDIMLS, VECTOR, LSTSQR);
  4
  5 CONST
  6    MAXDIMLS = 10;
  7
  8 TYPE
  9    VECTOR = ARRAY[1..MAXDIMLS] OF REAL;
 10
 11 PROCEDURE LSTSQR( N, D: INTEGER;  VAR XV, YV, BV: VECTOR;  VAR ERR: BOOLEAN);
 12 {
 13    Input
```

```
14        n   -- Number of points to fit
15        d   -- Degree of polynomial
16        xv  -- Array of x values to be fit
17        yv  -- Array of y values corresponding to x
18
19    Output
20        bv  -- Coefficients of polynomial
21        err -- error flag
22  }
23
24  BEGIN
25  END;
 1  {$include:'LESTSQAR.INT'}
 2
 3  IMPLEMENTATION OF LESTSQAR;
 4
 5  TYPE
 6      PNTRV  = ARRAY[1..MAXDIMLS] OF INTEGER;
 7      MATRIX = ARRAY[1..MAXDIMLS] OF VECTOR;
 8
 9  PROCEDURE WRTVCT( V: VECTOR; N: INTEGER);
10      VAR I: INTEGER;
11      BEGIN
12      FOR I := 1 TO N DO WRITE( V[I]:13);
13      WRITELN;
14      END;
15
16  FUNCTION MIN( I, J: INTEGER): INTEGER;
17      BEGIN
18      IF I < J THEN MIN := I ELSE MIN := J;
19      END;
20
21  FUNCTION AMAX( X, Y: REAL): REAL;
22      BEGIN
23      IF X > Y THEN AMAX := X ELSE AMAX := Y;
24      END;
25
26  FUNCTION SIGN( X, SGN: REAL): REAL;
27      BEGIN
28      IF SGN < 0 THEN SIGN := -ABS( X) ELSE SIGN := ABS( X);
29      END;
30
31  PROCEDURE SROWSWAP( VAR X, Y: VECTOR);
32  {
33    Exchange rows
34  }
35      VAR
36          T: VECTOR;
37      BEGIN
38      T := X; X := Y; Y := T;
39      END;
40
41
42  FUNCTION SVCTNRM2(    N, M: INTEGER;
43                    VAR X: VECTOR): REAL;
44  {
45    Calculate the 2-norm of the vector X from N to M
46  }
47      VAR
48          I: INTEGER;
49          S: REAL;
50      BEGIN
51      S := SQR( X[N]);
```

```
52      FOR I := N+1 TO M DO S := S + SQR( X[I]);
53      SVCTNRM2 := SQRT( S);
54      END;
55
56 PROCEDURE SVCTSCL(     N, M: INTEGER;
57                        S: REAL;
58                        VAR X: VECTOR);
59 {
60   Scale the vector X from N to M by S
61 }
62      VAR
63        I: INTEGER;
64      BEGIN
65      FOR I := N TO M DO X[I] := S * X[I];
66      END;
67
68
69 PROCEDURE SVCTAXPY(    N, M: INTEGER;
70                        S: REAL;
71                        VAR X, Y: VECTOR);
72 {
73   Yn..m := S*Xn..m + Yn..m
74 }
75      VAR
76        I: INTEGER;
77      BEGIN
78      FOR I := N TO M DO Y[I] := S*X[I] + Y[I];
79      END;
80
81
82 FUNCTION SVCTDOT(     N, M: INTEGER;
83                       VAR X, Y: VECTOR): REAL;
84 {
85   Calculate the vector dot product from N to M of X and Y
86 }
87      VAR
88        I: INTEGER;
89        S: REAL;
90      BEGIN
91      S := X[N]*Y[N];
92      FOR I := N+1 TO M DO S := S + X[I]*Y[I];
93      SVCTDOT := S;
94      END;
95
96
97 PROCEDURE SVCTCPY(    N, M: INTEGER;
98                       VAR X, Y: VECTOR);
99 {
100   Copy the vector Xn..m to Yn..m
101 }
102     VAR
103       I: INTEGER;
104       S: REAL;
105     BEGIN
106     FOR I := N TO M DO Y[I] := X[I];
107     END;
108
109 PROCEDURE PSQRDC( VAR X:        MATRIX;
110                       N:        INTEGER;
111                       P:        INTEGER;
112                   VAR QRAUX:    VECTOR;
113                   VAR JPVT:     PNTRV;
114                       PVT:      BOOLEAN);
```

```
115
116 {
117 {   SQRDC uses householder transformations to compute the QR
118 {   decomposition of an N by P matrix X.  Column pivoting
119 {   based on the 2-norms of the reduced columns may be
120 {   performed at the users option
121 { }
122
123     VAR
124        J, JJ, JP, L, LP1, LUP, MAXJ, PL, PU: INTEGER;
125        MAXNRM, SNRM2, TT, NRMXL, T: REAL;
126        NEGJ, SWAPJ: BOOLEAN;
127        WORK: VECTOR;
128
129     BEGIN
130     PL := 1;
131     PU := 0;
132     IF PVT
133     THEN BEGIN
134
135 {     Pivoting has been requested.  Rearrange the columns
136       according to JPVT.
137 }
138        FOR J := 1 TO P
139        DO BEGIN
140           SWAPJ := JPVT[J] > 0;
141           NEGJ := JPVT[J] < 0;
142           JPVT[J] := J;
143           IF NEGJ THEN JPVT[J] := -J;
144           IF SWAPJ
145           THEN BEGIN
146              IF J <> PL THEN SROWSWAP( X[PL], X[J]);
147              JPVT[J] := JPVT[PL];
148              JPVT[PL] := J;
149              PL := PL + 1;
150              END;
151           END;
152        PU := P;
153        FOR JJ := 1 TO P
154        DO BEGIN
155           J := P - JJ + 1;
156           IF JPVT[J] < 0
157           THEN BEGIN
158              JPVT[J] := -JPVT[J];
159              IF J <> PU
160              THEN BEGIN
161                 SROWSWAP( X[PU], X[J]);
162                 JP := JPVT[PU];
163                 JPVT[PU] := JPVT[J];
164                 JPVT[J] := JP;
165                 END;
166              PU := PU - 1;
167              END;
168           END;
169        END;
170 {
171   Compute the norms of the free columns
172 }
173     IF PU >= PL
174     THEN FOR J := PL TO PU
175        DO BEGIN
176           QRAUX[J] := SVCTNRM2( 1, N, X[J]);
177           WORK[J] := QRAUX[J];
```

```
178            END;
179 {
180    Perform the Householder reduction of X
181 }
182    LUP := MIN( N, P);
183    FOR L := 1 TO LUP
184    DO BEGIN
185       IF (L >= PL) AND (L < PU)
186       THEN BEGIN
187 {
188          Locate the column of the largest norm and bring it
189          into the pivot position
190 }
191          MAXNRM := 0;
192          MAXJ := L;
193          FOR J := L TO PU
194          DO BEGIN
195             IF QRAUX[J] > MAXNRM
196             THEN BEGIN
197                MAXNRM := QRAUX[J];
198                MAXJ := J;
199                END;
200             END;
201
202          IF MAXJ <> L
203          THEN BEGIN
204             SRQWSWAP( X[L], X[MAXJ]);
205             QRAUX[MAXJ] := QRAUX[L];
206             WORK[MAXJ] := WORK[L];
207             JP := JPVT[MAXJ];
208             JPVT[MAXJ] := JPVT[L];
209             JPVT[L] := JP;
210             END;
211          END;
212
213       QRAUX[L] := 0;
214       IF L <> N
215       THEN BEGIN
216 {
217          Compute the householder transformation for column L
218 }
219          NRMXL := SVCTNRM2( L, N, X[L]);
220          IF NRMXL <> 0
221          THEN BEGIN
222             IF X[L,L] <> 0 THEN NRMXL := SIGN( NRMXL, X[L,L]);
223             SVCTSCL( L, N, 1.0/NRMXL, X[L]);
224             X[L,L] := 1.0 + X[L,L];
225 {
226             Apply the transformation to the remaining columns,
227             updating the norms
228 }
229             LP1 := L+1;
230             IF P >= LP1
231             THEN BEGIN
232                FOR J := LP1 TO P
233                DO BEGIN
234                   T := -SVCTDOT( L, N, X[L], X[J]) / X[L,L];
235                   SVCTAXPY( L, N, T, X[L], X[J]);
236                   IF (J >= PL) AND (J <= PU)
237                   THEN IF QRAUX[J] <> 0
238                   THEN BEGIN
239                      TT := 1.0 - SQR( ABS( X[J,L]) / QRAUX[J]);
240                      TT := AMAX( TT, 0.0);
```

```
241                     T := TT;
242                     TT := 1.0 + 0.05*TT*SQR( QRAUX[J] / WORK[J]);
243                     IF TT <> 1
244                     THEN QRAUX[J] := QRAUX[J]*SQRT( T)
245                     ELSE BEGIN
246                        QRAUX[J] := SVCTNRM2( L+1, N, X[J]);
247                        WORK[J] := QRAUX[J];
248                        END;
249                  END;
250               END;
251            END;
252 {
253          Save the transformation
254 }
255          QRAUX[L] := X[L,L];
256          X[L,L] := -NRMXL;
257          END;
258       END;
259    END;
260 END;
261
262 PROCEDURE PSQRSL( VAR X:       MATRIX;
263                       N:       INTEGER;
264                       K:       INTEGER;
265                   VAR QRAUX,
266                       Y:       VECTOR;
267                   VAR QY,
268                       QTY,
269                       B,
270                       RSD,
271                       XB:      VECTOR;
272                       JOB:     INTEGER;
273                   VAR INFO:    INTEGER);
274 {
275 {  PSQRSL applies the output of PSQRDC to compute coordinate
276 {  transformations, projections, and least squares solutions.
277 { }
278    LABEL
279       90; { Error escape }
280
281    VAR
282       I, J, JJ, JU, KP1: INTEGER;
283       T, TEMP: REAL;
284       CB, CQY, CQTY, CR, CXB: BOOLEAN;
285
286    BEGIN
287 {
288    Set INFO flag
289 }
290    INFO := 0;
291 {
292    Determine what is to be computed
293 }
294    CQY  := (JOB DIV 10000) <> 0;
295    CQTY := (JOB MOD 10000) <> 0;
296    CB   := ((JOB MOD 1000) DIV 100) <> 0;
297    CR   := ((JOB MOD 100) DIV 10) <> 0;
298    CXB  := (JOB MOD 10) <> 0;
299    JU := MIN( K, N-1);
300 {
301    Special action when N=1
302 }
303    IF JU = 0
```

```
304       THEN BEGIN
305          IF CQY THEN QY[1] := Y[1];
306          IF CQTY THEN QTY[1] := Y[1];
307          IF CXB THEN XB[1] := Y[1];
308          IF CB
309          THEN BEGIN
310             IF X[1,1] = 0
311             THEN INFO := 1
312             ELSE B[1] := Y[1]/X[1,1];
313             END;
314          IF CR THEN RSD[1] := 0;
315          END
316       ELSE BEGIN
317 {
318          Set up to compute QY or trans(Q)*Y
319 }
320          IF CQY THEN QY := Y;
321          IF CQTY THEN QTY := Y;
322          IF CQY
323          THEN BEGIN
324 {
325             Compute Q*Y
326 }
327             FOR JJ := 1 TO JU
328             DO BEGIN
329                J := JU - JJ + 1;
330                IF QRAUX[J] <> 0
331                THEN BEGIN
332                   TEMP := X[J,J];
333                   X[J,J] := QRAUX[J];
334                   T := -SVCTDOT( J, N, X[J], QY) / X[J,J];
335                   SVCTAXPY( J, N, T, X[J], QY);
336                   X[J,J] := TEMP;
337                   END;
338                END;
339             END;
340          IF CQTY
341          THEN BEGIN
342 {
343             Compute trans(Q)*Y
344 }
345             FOR J := 1 TO JU
346             DO BEGIN
347                IF QRAUX[J] <> 0
348                THEN BEGIN
349                   TEMP := X[J,J];
350                   X[J,J] := QRAUX[J];
351                   T := -SVCTDOT( J, N, X[J], QTY) / X[J,J];
352                   SVCTAXPY( J, N, T, X[J], QTY);
353                   X[J,J] := TEMP;
354                   END;
355                END;
356             END;
357 {
358          Set up to compute B, RSD, or XB
359 }
360          IF CB THEN SVCTCPY( 1, K, QTY, B);
361          KP1 := K + 1;
362          IF CXB                 THEN SVCTCPY( 1, K, QTY, XB);
363          IF CR AND (K < N)      THEN SVCTCPY( KP1, N, QTY, RSD);
364          IF CXB AND (KP1 <= N) THEN FOR I := KP1 TO N DO XB[I] := 0;
365          IF CR                  THEN FOR I := 1 TO K DO RSD[I] := 0;
366          IF CB
```

```
367            THEN BEGIN
368    {
369                Compute B
370    }
371                FOR JJ := 1 TO K
372                DO BEGIN
373                    J := K - JJ + 1;
374                    IF X[J,J] = 0
375                    THEN BEGIN
376                        INFO := J;
377                        GOTO 90; { Error escape }
378                        END;
379                    B[J] := B[J] / X[J,J];
380                    IF J <> 1
381                    THEN BEGIN
382                        T := -B[J];
383                        SVCTAXPY( 1, J-1, T, X[J], B);
384                        END;
385                    END;
386                END;
387  90:
388            IF CR OR CXB
389            THEN BEGIN
390    {
391                Compute RSD or XB as required
392    }
393                FOR JJ := 1 TO JU
394                DO BEGIN
395                    J := JU - JJ + 1;
396                    IF QRAUX[J] <> 0
397                    THEN BEGIN
398                        TEMP := X[J,J];
399                        X[J,J] := QRAUX[J];
400                        IF CR
401                        THEN BEGIN
402                            T := -SVCTDOT( J, N, X[J], RSD) / X[J,J];
403                            SVCTAXPY( J, N, T, X[J], RSD);
404                            END;
405                        IF CXB
406                        THEN BEGIN
407                            T := -SVCTDOT( J, N, X[J], XB) / X[J,J];
408                            SVCTAXPY( J, N, T, X[J], XB);
409                            END;
410                        X[J,J] := TEMP;
411                        END;
412                    END;
413                END;
414            END;
415        END;
416
417  PROCEDURE PSQRST( VAR X:      MATRIX;
418                        N:      INTEGER;
419                        P:      INTEGER;
420                        Y:      VECTOR;
421                        TOL:    REAL;
422                    VAR B:      VECTOR;
423                    VAR RSD:    VECTOR;
424                    VAR K:      INTEGER;
425                    VAR JPVT:   PNTRV;
426                    VAR QRAUX:  VECTOR;
427                    VAR INFO:   INTEGER);
428
429      VAR
```

```
430         J, KK, M: INTEGER;
431         T: REAL;
432         TMP: VECTOR;
433
434     BEGIN
435     {
436     Initialize JPVT so that all columns are free
437     }
438     FOR J := 1 TO P DO JPVT[J] := 0;
439     {
440     Reduce X
441     }
442     PSQRDC( X, N, P, QRAUX, JPVT, TRUE);
443     {
444     Determine which columns to use
445     }
446     K := 0;
447     M := MIN( N, P);
448     KK := 1;
449     WHILE KK <= M
450     DO BEGIN
451        IF ABS( X[KK,KK]) <= TOL*ABS( X[1,1])
452        THEN KK := M
453        ELSE K := KK;
454        KK := KK+1;
455        END;
456     {
457     Solve the truncated least sqares problem
458     }
459     IF K <> 0
460     THEN PSQRSL( X, N, K, QRAUX, Y, TMP, TMP, B, RSD, TMP, 110, INFO);
461     {
462     Set the unused components of B to zero and initialize JPVT
463     for unscrambling
464     }
465     FOR J := 1 TO P
466     DO BEGIN
467        JPVT[J] := -JPVT[J];
468        IF J > K THEN B[J] := 0;
469        END;
470     {
471     Unscramble the solution
472     }
473     FOR J := 1 TO P
474     DO BEGIN
475        IF JPVT[J] <= 0
476        THEN BEGIN
477           K := -JPVT[J];
478           JPVT[J] := K;
479           WHILE K <> J
480           DO BEGIN
481              T := B[J];
482              B[J] := B[K];
483              B[K] := T;
484              JPVT[K] := -JPVT[K];
485              K := JPVT[K];
486              END;
487           END;
488        END;
489     END;
490
491 PROCEDURE LSTSQR;
492     VAR
```

```
493        I, J, K, P: INTEGER;
494        X, XP: REAL;
495        AM: MATRIX;
496        YL, BL, RSD, QRAUX: VECTOR;
497        JPVT: PNTRV;
498
499     BEGIN
500        P := D+1;
501        FOR I := 1 TO N
502        DO BEGIN
503           X := XV[I];
504           XP := 1;
505           FOR J := 1 TO P
506           DO BEGIN
507              AM[J,I] := XP;
508              XP := XP*X;
509              END;
510           END;
511
512        YL := YV;
513        PSQRST( AM, N, P, YL, 0.0, BL, RSD, K, JPVT, QRAUX, I);
514        BV := BL;
515        ERR := I <> 0;
516        END;
517
518 BEGIN
519 END.
  1 INTERFACE(0);
  2
  3 UNIT MVMON( MV_MONITOR);
  4
  5 FUNCTION MV_MONITOR: BOOLEAN;
  6
  7 BEGIN
  8 END;
  1 {$include:'IO\SCREEN.INT'}
  2 {$include:'IO\KEYBRD.INT'}
  3 {$include:'IO\PROMPT.INT'}
  4 {$include:'PRAMIFAC.INT'}
  5 {$include:'DATACQ.INT'}
  6 {$include:'MVMON.INT'}
  7
  8 IMPLEMENTATION OF MVMON;
  9
 10 USES SCREEN,
 11      KEYBRD,
 12      PROMPT,
 13      DATACQ,
 14      PRAMIFAC;
 15
 16
 17 FUNCTION MV_MONITOR;
 18     LABEL
 19        86;   { Abort via escape }
 20
 21     CONST
 22        ESC = CHR( 27);
 23        CMAX = 6;
 24        HEADING = 'mV Monitor';
 25        N = 10;
 26        STATS_COLOR = ESC*'[37m';
 27        NORMAL_COLOR = ESC*'[32m';
 28
```

```
29      TYPE
30         COLRNG = 1..CMAX;
31
32      VAR
33         I: INTEGER;
34         X: REAL;
35         C: COLRNG;
36         CH: CHAR;
37         SLOPE, OFFSET, MVADC, ADCCNT: MVVCT;
38         IA: ADCNAM;
39         SUMX, SUMX2: ARRAY [1..CMAX] OF REAL;
40
41      BEGIN
42   { Initialize before run
43   }
44      IF NOT DATACQ_SETUP( SLOPE, OFFSET)
45      THEN BEGIN
46         WRITEPC( 25, 1, 'Not all channels calibrated');
47         MV_MONITOR := FALSE;
48         GOTO 86;
49         END;
50
51      CLR2_25;
52      SYNC_NEXT( -1);
53
54      REPEAT
55         WRITELN(
56   {12345678911234567892123456789312345678941234567895123456789612345678971234567}
57   {       xx.xx       xx.xx      xx.xx      xx.xx     xx.xx       xxx.xx  }
58   '    center tc    uncomp        tab     calc comp  act comp   photocell');
59         FOR C := 1 TO CMAX
60         DO BEGIN
61            SUMX[C] := 0;
62            SUMX2[C] := 0;
63            END;
64
65         FOR I := 1 TO N
66         DO BEGIN
67            ADC_SCAN( 1.0, ADCCNT);
68            FOR IA := LOWER( IA) TO UPPER( IA)
69            DO MVADC[IA] := OFFSET[IA] + SLOPE[IA]*ADCCNT[IA];
70
71            FOR C := 1 TO CMAX
72            DO BEGIN
73               CASE C OF
74                  1: X := MVADC[CNTR_TC];
75                  2: X := MVADC[UNCOMP];
76                  3: X := MVADC[TAB];
77                  4: X := MVADC[UNCOMP] - MVADC[TAB];
78                  5: X := MVADC[ACT_COMP];
79                  6: X := MVADC[PHOTOCELL];
80                  END;
81               WRITE( X:11:3);
82               SUMX[C] := SUMX[C]+X;
83               SUMX2[C] := SUMX2[C]+X*X;
84               END;
85            WRITELN;
86            END;
87
88         WRITE( STATS_COLOR);
89         FOR C := 1 TO CMAX DO WRITE( (SUMX[C]/N):11:3);
90
91         WRITELN;
```

```
92        FOR C := 1 TO CMAX
93        DO WRITE( ( SQRT( ABS( N*SUMX2[C] - SQR( SUMX[C])) / (N*(N-1)) ) ):11:3 );
94        WRITELN( NORMAL_COLOR);
95        WRITELN;
96
97        UNTIL CHKESCAPE;
98
99     INITSCRN;
100    MV_MONITOR := TRUE;
101 86:
102    END;
103
104 BEGIN
105 END.
  1 INTERFACE(0);
  2
  3 UNIT PHOTOCAL( PC_REC, PHOTO_CAL, GET_PC);
  4
  5 USES PRAMIFAC;
  6
  7 TYPE
  8    PC_REC = RECORD
  9              YR, MO, DA: INTEGER;
 10              FILTERS: INTEGER;
 11              FILTER, FLTRVOLT: ARRAY [1..MAXFLTR] OF REAL;
 12              END;
 13
 14 FUNCTION PHOTO_CAL( PR: PR_REC): BOOLEAN;
 15
 16 PROCEDURE GET_PC( VAR PC: PC_REC);
 17
 18 BEGIN
 19 END;
  1 {$include:'IO\SCREEN.INT'}
  2 {$include:'IO\KEYBRD.INT'}
  3 {$include:'IO\PROMPT.INT'}
  4 {$include:'PRAMIFAC.INT'}
  5 {$include:'DATACQ.INT'}
  6 {$include:'PHOTOCAL.INT'}
  7
  8 IMPLEMENTATION OF PHOTOCAL;
  9
 10 USES SCREEN,
 11      KEYBRD,
 12      PROMPT,
 13      DATACQ,
 14      PRAMIFAC;
 15
 16 TYPE
 17    STR2 = STRING( 2);
 18
 19 PROCEDURE GETDAT( VARS YR, MO, DA: INTEGER); EXTERN;
 20
 21 PROCEDURE ENDXQQ; EXTERN;
 22
 23 {$include:'FILEERRN.PAS'}
 24
 25 FUNCTION STRZZ( N: INTEGER): STR2;
 26    VAR
 27       I: INTEGER;
 28       TSTR: STR2;
 29    BEGIN
 30    TSTR := '00';
```

```
31      FOR I := 2 DOWNTO 1
32      DO BEGIN
33         TSTR[I] := CHR( ORD('0') + N MOD 10);
34         N := N DIV 10;
35         END;
36      STRZZ := TSTR;
37      END;
38
39
40 FUNCTION PHOTO_CAL;
41    LABEL
42       85,  { Abort exit -- calibration aborted by escape }
43       86;  { Abort exit -- photocell channel not calibrated }
44
45    CONST
46       HEADING = 'Photocell Calibration';
47       ESC = CHR( 27);
48
49    VAR
50       I, ROW: INTEGER;
51       CH: CHAR;
52       PC, PC_OLD: PC_REC;
53       PCF: FILE OF PC_REC;
54       FILNAM: FILNAMTYP;
55       MV, SLP, OFS: MVVCT;
56       TBOOL: BOOLEAN;
57
58    BEGIN
59 { Initialize before run
60 }
61    IF NOT PHOTO_SETUP
62    THEN BEGIN
63       WRITEPC( 25, 1, 'Photocell channel not calibrated');
64       PHOTO_CAL := FALSE;
65       GOTO 86;
66       END;
67    TBOOL := DATACQ_SETUP( SLP, OFS);
68
69    WRITEPC( 1, 30, HEADING);
70    CLR2_25;
71
72    ROW := 4;
73    GETDAT( PC.YR, PC.MO, PC.DA);
74    PC.YR := PC.YR MOD 100;
75    PC.FILTERS := PR.FILTERS;
76    WITH PR
77    DO BEGIN
78       FOR I := 1 TO FILTERS
79       DO BEGIN
80          WRITEPC( ROW, 1, 'Insert ');
81          WRITE( FILTER[I]:0:2, ' % filter and hit Enter to take reading');
82          REPEAT CH := GETCH UNTIL (CH = CHR( 13)) OR (CH = ESC);
83          IF CH = ESC THEN GOTO 85;
84          PC.FILTER[I] := PR.FILTER[I];
85          ADC_SCAN( -1, MV);
86          PC.FLTRVOLT[I] := MV[PHOTOCELL]*SLP[PHOTOCELL] + OFS[PHOTOCELL];
87          CLRLINE( ROW, 1);
88          WRITE( FILTER[I]:6:2, '% = ', PC.FLTRVOLT[I]:0:1, ' mV');
89          ROW := ROW+2;
90          END;
91       END;
92
93 { Get old photocell cal and save under date taken (PCyymmdd.OSU)
```

```
 94 }
 95     ASSIGN( PCF, 'photcell.osu');
 96     PCF.TRAP := TRUE;
 97     PCF.ERRS := 0;
 98     RESET( PCF);
 99     IF PCF.ERRS = FLOK
100     THEN BEGIN
101        GET( PCF);
102        PC_OLD := PCF^;
103        CLOSE( PCF);
104        FILNAM := 'PC';
105        CONCAT( FILNAM, (STRZZ( PC_OLD.YR)));
106        CONCAT( FILNAM, (STRZZ( PC_OLD.MO)));
107        CONCAT( FILNAM, (STRZZ( PC_OLD.DA)));
108        CONCAT( FILNAM, '.OSU');
109        ASSIGN( PCF, FILNAM);
110        REWRITE( PCF);
111        PCF^ := PC_OLD;
112        PUT( PCF);
113        CLOSE( PCF);
114        ASSIGN( PCF, 'photcell.osu');
115        END;
116
117 {  Write new data
118 }
119     PCF.ERRS := 0;
120     REWRITE( PCF);
121     PCF^ := PC;
122     PUT( PCF);
123     CLOSE( PCF):
124 85:
125     PHOTO_CAL := TRUE;
126 86:
127     END;
128
129 PROCEDURE GET_PC;
130     VAR
131        PCF: FILE OF PC_REC;
132     BEGIN
133     ASSIGN( PCF, 'photcell.osu');
134     PCF.TRAP := TRUE;
135     PCF.ERRS := 0;
136     RESET( PCF);
137     IF PCF.ERRS = FLOK
138     THEN BEGIN
139        GET( PCF);
140        PC := PCF^;
141        CLOSE( PCF);
142        END
143     ELSE BEGIN
144        WRITEPC( 24, 1, 'File error on PHOTOCELL.OSU');
145        ENDXQQ;
146        END;
147     END;
148
149 BEGIN
150 END.
  1 INTERFACE(2);
  2
  3 UNIT PRAMIFAC( MAXFLTR, DATACHNS, MAXAVG, MAXSEC, PR_REC,
  4               GET_PARAM, PUT_PARAM, NAME_ADC, NAME_BOT, RUNFILNAM,
  5               ADCNAM, UNCOMP, TAB, PHOTOCELL, CNTR_TC, ACT_COMP,
  6               BOTNAM, OPEN_DOOR, INSERT,
```

```
  7              FILNAMTYP, ADCSTRTYP, ADCTYP, OSUTYP, WRSTR, MATSTR,
  8              TIMVCT, MAXSPC, MAXTIMX, FMAXRUNNO,
  9              MVVCT, MVMAT);
 10
 11 CONST
 12    MAXFLTR = 6;
 13    DATACHNS = 5;  { This must be the number values in ADCNAM }
 14    MAXAVG = 64;   { Max ADC averages }
 15    MAXSEC = 900;  { Max burn time in seconds }
 16    MAXSPC = 20;   { Max number of specimens in a run }
 17    MAXTIMX = 8;   { Max number of time columns in report }
 18    FMAXRUNNO = 999999.0; { Max run number -- to big for int2 }
 19
 20 TYPE
 21    { Changes made to ADCNAM must be reflected in DATACHNS }
 22    ADCNAM = ( UNCOMP, TAB, PHOTOCELL, CNTR_TC, ACT_COMP);
 23    ADCTYP = ARRAY [ADCNAM] OF INTEGER;
 24    OSUTYP = ARRAY [0..MAXSEC] OF ADCTYP;
 25    MVVCT = ARRAY [ADCNAM] OF REAL;
 26    MVMAT = ARRAY [0..MAXSEC] OF MVVCT;
 27    BOTNAM = ( OPEN_DOOR, INSERT);
 28    TIMVCT = ARRAY [1..MAXTIMX+2] OF INTEGER;
 29    FILNAMTYP = LSTRING( 14);
 30    WRSTR = LSTRING( 20);
 31    MATSTR = LSTRING( 30);
 32    ADCSTRTYP = LSTRING( 15);
 33
 34    PR_REC = RECORD
 35              { ADC Device # and Channel # by name }
 36                ADCDEV, ADCCHN: ARRAY [ADCNAM] OF INTEGER;
 37
 38              { Binary Out Channel # by name }
 39                BOTCHN: ARRAY [BOTNAM] OF INTEGER;
 40
 41              { Door sequence times in ms }
 42                OPNINS, INSCLS, OPNRMV, RMVCLS: REAL;
 43
 44              { ADC samples to average }
 45                AVECNT: INTEGER;
 46
 47              { Optical density of filter glasses }
 48                FILTERS: INTEGER;
 49                FILTER: ARRAY [1..MAXFLTR] OF REAL;
 50
 51              { Run event times }
 52                HOLDTIME, AVRGTIME, BURNTIME: INTEGER;
 53
 54              { Specimen count and type }
 55                DMYCNT, SPCCNT: INTEGER;
 56                SPCTYP: CHAR;
 57
 58              { Other run variables }
 59                HEATFLUX, QK_COMP, QK_UNCOMP, VFLOW, SRFCAREA: REAL;
 60                TINLET: REAL;
 61                UNCOMP_CNT: INTEGER;
 62
 63              { Run number, prefix, and current dummy }
 64                RUNNO: INTEGER4;
 65                RUNPRFX: CHAR;
 66                RUN_DUMMY: FILNAMTYP;
 67
 68              { Run description }
 69                WR_NUMBER: WRSTR;
```

```
70            MATERIAL: MATSTR;
71
72            { Data processing fields }
73              AUTO_PROC: BOOLEAN;
74              DP_DUMMY: FILNAMTYP;
75              HEAT_COMP, SMOK_CNTR: BOOLEAN;
76              HEAT_RPT, SMOK_RPT: TIMVCT;
77              END;
78
79 PROCEDURE GET_PARAM( VAR PR_ARG: PR_REC);
80 PROCEDURE PUT_PARAM( CONST PR_ARG: PR_REC);
81 FUNCTION NAME_ADC( IA: ADCNAM): ADCSTRTYP;
82 FUNCTION NAME_BOT( IB: BOTNAM): ADCSTRTYP;
83 FUNCTION RUNFILNAM( RUNPRFX: CHAR;  RUNNO: INTEGER4): FILNAMTYP;
84
85 BEGIN
86 END;
 1 {$include:'PRAMIFAC.INT'}
 2 {$include:'IO\SCREEN.INT'}
 3 {$include:'IO\KEYBRD.INT'}
 4 {$include:'IO\PROMPT.INT'}
 5
 6 IMPLEMENTATION OF PRAMIFAC;
 7
 8 USES SCREEN,
 9      KEYBRD,
10      PROMPT;
11
12 CONST
13    PARAM_FILNAM = 'params.osu';
14
15 VAR
16    PR: PR_REC;
17    PARAMF: FILE OF PR_REC;
18
19 PROCEDURE ENDXQQ; EXTERN;
20
21 {$include:'FILEERRS.PAS'}
22
23 FUNCTION NAME_ADC;
24    BEGIN
25    CASE IA OF
26    UNCOMP:    NAME_ADC := 'Uncomp';
27    TAB:       NAME_ADC := 'Tab';
28    PHOTOCELL: NAME_ADC := 'Photocell';
29    CNTR_TC:   NAME_ADC := 'ceNter tc';
30    ACT_COMP:  NAME_ADC := 'Actual comp';
31       END;
32    END;
33
34
35 FUNCTION NAME_BOT;
36    BEGIN
37    CASE IB OF
38    OPEN_DOOR: NAME_BOT := 'Open';
39    INSERT:    NAME_BOT := 'Insert';
40       END;
41    END;
42
43
44 FUNCTION RUNFILNAM;
45 {                                                        }
46 {  Form run file name                                    }
```

```
 47 {                                                          }
 48    VAR
 49       I: INTEGER;
 50       N: INTEGER4;
 51       CH: CHAR;
 52       TSTR, NAME: FILNAMTYP;
 53
 54    BEGIN
 55    NAME := ' ';
 56    NAME[1] := RUNPRFX;
 57    N := RUNNO;
 58    TSTR := '00000';
 59    FOR I := 5 DOWNTO 1
 60    DO BEGIN
 61       TSTR[I] := CHR( ORD( ORD('0') + N MOD 10));
 62       N := N DIV 10;
 63       END;
 64    CONCAT( NAME, TSTR);
 65    RUNFILNAM := NAME;
 66    END;
 67
 68 PROCEDURE DEFAULT_PARAM;
 69    VAR
 70       I: INTEGER;
 71       IA: ADCNAM;
 72       IB: BOTNAM;
 73    BEGIN
 74    WITH PR
 75    DO BEGIN
 76
 77       FOR IA := LOWER( IA) TO UPPER( IA)
 78       DO BEGIN
 79          ADCDEV[IA] := 0;
 80          ADCCHN[IA] := ORD( IA)+1;
 81          END;
 82
 83       FOR IB := LOWER( IB) TO UPPER( IB)
 84       DO BOTCHN[IB] := ORD( IB);
 85
 86       OPNINS := 0.5;
 87       INSCLS := 3.0;
 88       OPNRMV := 0.5;
 89       RMVCLS := 5.0;
 90
 91       AVECNT := 32;
 92       DMYCNT := 3;
 93
 94       FILTERS := 5;
 95       FILTER[1] := 100.0;
 96       FILTER[2] := 90.0;
 97       FILTER[3] := 80.0;
 98       FILTER[4] := 70.0;
 99       FILTER[5] := 60.0;
100
101       HOLDTIME := 60;
102       AVRGTIME := 20;
103       BURNTIME := 5*60;
104
105       HEATFLUX := 3.5;
106       RUNPRFX := 'C';
107       QK_COMP := 15.0;
108       QK_UNCOMP := 15.0;
109       VFLOW := 40;
```

```
110         SRFCAREA := 232.26;
111         TINLET := 25;
112         UNCOMP_CNT := 5;
113
114         RUNNO := 1000;
115         SPCTYP := ' ';
116         RUN_DUMMY := 'DMC00';
117         WR_NUMBER := NULL;
118         MATERIAL := NULL;
119         SPCCNT := 0;
120         AUTO_PROC := TRUE;
121
122         DP_DUMMY := NULL;
123         HEAT_COMP := FALSE;
124         SMOK_CNTR := FALSE;
125         HEAT_RPT := TIMVCT( 30, 60, 120, 180, 300, 600, 900, -1, -1, -1);
126         SMOK_RPT := TIMVCT( 30, 60,  90, 120, 180, 240, 300, 900, -1, -1);
127         END;
128     END;
129
130 PROCEDURE GET_PARAM;
131     BEGIN
132     PR_ARG := PR;
133     END;
134
135 PROCEDURE PUT_PARAM;
136     BEGIN
137     PR := PR_ARG;
138     ASSIGN( PARAMF, PARAM_FILNAM);
139     PARAMF.TRAP := TRUE;
140     PARAMF.ERRS := 0;
141     PARAMF.MODE := SEQUENTIAL;
142     REWRITE( PARAMF);
143     IF (PARAMF.ERRS <> FLOK) AND (PARAMF.ERRS <> FLNOTFND)
144     THEN FILE_ERRS( PARAMF.ERRS)
145     ELSE BEGIN
146        PARAMF.ERRS := 0;
147        PARAMF^ := PR;
148        PUT( PARAMF);
149        CLOSE( PARAMF);
150        END;
151     END;
152
153 PROCEDURE READ_PARAM;
154     BEGIN
155     ASSIGN( PARAMF, PARAM_FILNAM);
156     PARAMF.TRAP := TRUE;
157     PARAMF.MODE := SEQUENTIAL;
158     PARAMF.ERRS := 0;
159     RESET( PARAMF);
160     IF PARAMF.ERRS <> FLOK
161     THEN BEGIN
162        IF PARAMF.ERRS <> FLNOTFND THEN FILE_ERRS( PARAMF.ERRS);
163        CLOSE( PARAMF);
164        PARAMF.ERRS := 0;
165        DEFAULT_PARAM;
166        END
167     ELSE BEGIN
168        GET( PARAMF);
169        PR := PARAMF^;
170        CLOSE( PARAMF);
171        END;
172     END;
```

```
173
174 BEGIN
175 READ_PARAM;
176 END.
  1 INTERFACE(1);
  2
  3 UNIT PROMPT( VALBND, FVALBND, NOCHK, GE, GT, LT, LE, GELE, GELT, GTLE, GTLT,
  4              GETREAL, GETINT, PROMPTI, PROMPTR, UPDATER, UPDATEI,
  5              PROMPTL, PROMPTLA);
  6
  7 USES KEYBRD;
  8
  9 TYPE
 10    BNDCHKTYP = (NOCHK, GE, GT, LT, LE, GELE, GELT, GTLE, GTLT);
 11    VALBND = RECORD
 12             LOWBND: INTEGER;
 13             BNDCHK: BNDCHKTYP;
 14             HIBND: INTEGER;
 15             END;
 16    FVALBND = RECORD
 17             LOWBND: REAL;
 18             BNDCHK: BNDCHKTYP;
 19             HIBND: REAL;
 20             END;
 21
 22 PROCEDURE GETREAL( VAR RVAL: REAL;  CONST VALCHK: FVALBND;  VAR ENTERED: BOOLEAN);
 23
 24 PROCEDURE GETINT( VAR IVAL: INTEGER;  CONST VALCHK: VALBND;  VAR ENTERED: BOOLEAN);
 25
 26 FUNCTION PROMPTI( CONST ROW, COL: INTEGER;  CONST STR: STRING;
 27                   VAR IVAL: INTEGER;  CONST VALCHK: VALBND): BOOLEAN;
 28
 29 FUNCTION PROMPTR( CONST ROW, COL: INTEGER;  CONST STR: STRING;
 30                   VAR RVAL: REAL;  CONST VALCHK: FVALBND): BOOLEAN;
 31
 32 PROCEDURE UPDATER( CONST ROW, COL: INTEGER;  CONST STR: STRING;
 33                   VAR RVAL: REAL;  CONST VALCHK: FVALBND);
 34
 35 PROCEDURE UPDATEI( CONST ROW, COL: INTEGER;  CONST STR: STRING;
 36                   VAR IVAL: INTEGER;  CONST VALCHK: VALBND);
 37
 38 FUNCTION PROMPTL( CONST ROW, COL: INTEGER;  CONST STR: STRING;
 39                   VAR LSTR: GLSTRTYP): BOOLEAN;
 40
 41 FUNCTION PROMPTLA( CONST ROW, COL: INTEGER;  CONST STR: STRING;
 42                    VAR LSTR: GLSTRTYP): BOOLEAN;
 43
 44 BEGIN
 45 END;
  1 {$include:'KEYBRD.INT'}
  2 {$include:'SCREEN.INT'}
  3 {$include:'PROMPT.INT'}
  4
  5 IMPLEMENTATION OF PROMPT;
  6
  7 USES SCREEN, KEYBRD;
  8
  9
 10 CONST
 11    CURSSAVE = CHR(27)*'[s';
 12    CURSRSTR = CHR(27)*'[u';
 13
 14
```

```
15 FUNCTION BOUNDCHK( CONST VAL: INTEGER;   CONST VALCHK: VALBND): BOOLEAN;
16    VAR
17       OK1, OK2: BOOLEAN;
18       RELSTR: LSTRING(3);
19
20    BEGIN
21    WITH VALCHK
22    DO BEGIN
23       CASE BNDCHK OF
24
25       GT, GTLE, GTLT: BEGIN
26                       OK1 := VAL > LOWBND;
27                       IF NOT OK1 THEN RELSTR := '> ';
28                       END;
29
30       GE, GELE, GELT: BEGIN
31                       OK1 := VAL >= LOWBND;
32                       IF NOT OK1 THEN RELSTR := '>= ';
33                       END;
34
35       OTHERWISE OK1 := TRUE;
36          END;
37
38       CASE BNDCHK OF
39
40       LT, GELT, GTLT: BEGIN
41                       OK2 := VAL < HIBND;
42                       IF NOT OK2 THEN RELSTR := '< ';
43                       END;
44
45       LE, GELE, GTLE: BEGIN
46                       OK2 := VAL <= HIBND;
47                       IF NOT OK2 THEN RELSTR := '<= ';
48                       END;
49
50       OTHERWISE OK2 := TRUE;
51          END;
52
53       IF OK1 AND OK2
54       THEN BOUNDCHK := TRUE
55       ELSE BEGIN
56          WRITE( CURSSAVE);
57          WRITEPC( 25, 1, 'Value must be ');
58          IF OK2 THEN WRITE( RELSTR, LOWBND:0) ELSE WRITE( RELSTR, HIBND:0);
59          WRITE( CURSRSTR);
60          BOUNDCHK := FALSE;
61          END;
62    END;
63
64    END;
65
66
67 FUNCTION FBOUNDCHK( CONST VAL: REAL;   CONST VALCHK: FVALBND): BOOLEAN;
68    VAR
69       OK1, OK2: BOOLEAN;
70       RELSTR: LSTRING(3);
71
72    BEGIN
73    WITH VALCHK
74    DO BEGIN
75       CASE BNDCHK OF
76
77       GT, GTLE, GTLT: BEGIN
```

```
 78                        OK1 := VAL > LOWBND;
 79                        IF NOT OK1 THEN RELSTR := '> ';
 80                        END;
 81
 82     GE, GELE, GELT: BEGIN
 83                        OK1 := VAL >= LOWBND;
 84                        IF NOT OK1 THEN RELSTR := '>= ';
 85                        END;
 86
 87     OTHERWISE OK1 := TRUE;
 88        END;
 89
 90     CASE BNDCHK OF
 91
 92     LT, GELT, GTLT: BEGIN
 93                        OK2 := VAL < HIBND;
 94                        IF NOT OK2 THEN RELSTR := '< ';
 95                        END;
 96
 97     LE, GELE, GTLE: BEGIN
 98                        OK2 := VAL <= HIBND;
 99                        IF NOT OK2 THEN RELSTR := '<= ';
100                        END;
101
102     OTHERWISE OK2 := TRUE;
103        END;
104
105     IF OK1 AND OK2
106     THEN FBOUNDCHK := TRUE
107     ELSE BEGIN
108        WRITE( CURSSAVE);
109        WRITEPC( 25, 1, 'Value must be ');
110        IF OK2 THEN WRITE( RELSTR, LOWBND:0:3) ELSE WRITE( RELSTR, HIBND:0:3);
111        WRITE( CURSRSTR);
112        FBOUNDCHK := FALSE;
113        END;
114     END;
115
116   END;
117
118
119 PROCEDURE GETREAL;
120    VAR
121       LSTR: GLSTRTYP;
122       OK, ERROR: BOOLEAN;
123
124    BEGIN
125    ERROR := FALSE;
126    LSTR := NULL;
127    REPEAT
128       LSTR := GETLSTR( LSTR);
129       IF LSTR.LEN > 0
130       THEN BEGIN
131          OK := DECODE( LSTR, RVAL);
132          IF OK
133          THEN BEGIN
134             OK := FBOUNDCHK( RVAL, VALCHK);
135             IF OK
136             THEN BEGIN
137                IF ERROR THEN CLRLINE( 25, 1);
138                ERROR := FALSE;
139                ENTERED := TRUE;
140                END
```

```
141             ELSE ERROR := TRUE;
142             END
143          ELSE BEGIN
144             WRITE( CURSSAVE);
145             WRITEPC( 25, 1, 'INPUT ERROR, RETRY.  Samples: -0.12 123 1.0e4');
146             WRITE( CURSRSTR);
147             ERROR := TRUE;
148             END
149          END
150       ELSE BEGIN
151          IF ERROR THEN CLRLINE( 25, 1);
152          ERROR := FALSE;
153          ENTERED := FALSE;
154          RVAL := 0;
155          END;
156       UNTIL NOT ERROR;
157    END;
158
159
160 PROCEDURE GETINT;
161    VAR
162       LSTR: GLSTRTYP;
163       OK, ERROR: BOOLEAN;
164
165    BEGIN
166    ERROR := FALSE;
167    LSTR := NULL;
168    REPEAT
169       LSTR := GETLSTR( LSTR);
170       IF LSTR.LEN > 0
171       THEN BEGIN
172          OK := DECODE( LSTR, IVAL);
173          IF OK
174          THEN BEGIN
175             OK := BOUNDCHK( IVAL, VALCHK);
176             IF OK
177             THEN BEGIN
178                IF ERROR THEN CLRLINE( 25, 1);
179                ERROR := FALSE;
180                ENTERED := TRUE;
181                END
182             ELSE ERROR := TRUE;
183             END
184          ELSE BEGIN
185             WRITE( CURSSAVE);
186             WRITEPC( 25, 1, 'INPUT ERROR, RETRY.  Samples: -12 123 +345');
187             WRITE( CURSRSTR);
188             ERROR := TRUE;
189             END
190          END
191       ELSE BEGIN
192          IF ERROR THEN CLRLINE( 25, 1);
193          ERROR := FALSE;
194          ENTERED := FALSE;
195          IVAL := 0;
196          END;
197       UNTIL NOT ERROR;
198    END;
199
200 FUNCTION PROMPTI;                  { prompt for integer value at (row,col) }
201    VAR
202       ENTERED: BOOLEAN;
203    BEGIN
```

```
204     CLRLINE( ROW, COL);
205     WRITE( STR);
206     GETINT( IVAL, VALCHK, ENTERED);
207     PROMPTI := ENTERED;
208     END;
209
210 FUNCTION PROMPTR;              { prompt for real value at (row,col) }
211     VAR
212         ENTERED: BOOLEAN;
213     BEGIN
214     CLRLINE( ROW, COL);
215     WRITE( STR);
216     GETREAL( RVAL, VALCHK, ENTERED);
217     PROMPTR := ENTERED;
218     END;
219
220 FUNCTION PROMPTL;              { prompt for string value at (row,col) }
221     BEGIN
222     CLRLINE( ROW, COL);
223     WRITE( STR);
224     LSTR := GETLSTR( NULL);
225     PROMPTL := LSTR.LEN <> 0;
226     END;
227
228 FUNCTION PROMPTLA;             { prompt to alter string value at (row,col) }
229     BEGIN
230     CLRLINE( ROW, COL);
231     WRITE( STR);
232     LSTR := GETLSTR( LSTR);
233     PROMPTLA := LSTR.LEN <> 0;
234     END;
235
236 PROCEDURE UPDATER;             { prompt for real value at (row,col) }
237     VAR
238         RTMP: REAL;
239         ENTERED: BOOLEAN;
240     BEGIN
241     CLRLINE( ROW, COL);
242     WRITE( STR);
243     GETREAL( RTMP, VALCHK, ENTERED);
244     IF ENTERED THEN RVAL := RTMP;
245     END;
246
247 PROCEDURE UPDATEI;             { prompt for integer value at (row,col) }
248     VAR
249         ITMP: INTEGER;
250         ENTERED: BOOLEAN;
251     BEGIN
252     CLRLINE( ROW, COL);
253     WRITE( STR);
254     GETINT( ITMP, VALCHK, ENTERED);
255     IF ENTERED THEN IVAL := ITMP;
256     END;
257
258 BEGIN
259 END.
  1 INTERFACE(4);
  2
  3 UNIT SCREEN( CLRSCRN, CLRLINE, CLR2_25, POSCURS, WRITEP, WRITEPC,
  4              WRITEU, WRITEPCU, WRITEPU, INITSCRN, NORMFG, MENUFG, ERRFG);
  5
  6 CONST
  7     ESC = CHR( 27);
```

```
  8     NORMFG = ESC*'[0;32m';
  9     MENUFG = ESC*'[36m';
 10     ERRFG = ESC*'[1;5;33m';
 11
 12 PROCEDURE CLRSCRN;
 13 PROCEDURE CLRLINE( CONST ROW, COL: INTEGER);
 14 PROCEDURE CLR2_25;
 15 PROCEDURE WRITEU( CONST STR: STRING);
 16 PROCEDURE POSCURS( CONST ROW, COL: INTEGER);
 17 PROCEDURE WRITEP( CONST ROW, COL: INTEGER;  CONST STR: STRING);
 18 PROCEDURE WRITEPC( CONST ROW, COL: INTEGER;  CONST STR: STRING);
 19 PROCEDURE WRITEPCU( CONST ROW, COL: INTEGER;  CONST STR: STRING);
 20 PROCEDURE WRITEPU( CONST ROW, COL: INTEGER;  CONST STR: STRING);
 21 PROCEDURE INITSCRN;
 22
 23 BEGIN
 24 END;
  1 {$include:'SCREEN.INT'}
  2
  3 IMPLEMENTATION OF SCREEN;
  4
  5 CONST
  6     VERSION = 'OSU  E6896A00';
  7     ESC = CHR( 27);
  8     CLEARLINE = ESC*'[K';
  9
 10 PROCEDURE CLRSCRN;                 { clear screen, position (1,1) }
 11     BEGIN
 12     WRITE( NORMFG, ESC, '[2J');
 13     END;
 14
 15 PROCEDURE INITSCRN;
 16     CONST
 17         GRN_ON_BLK = ESC*'[32;40m';
 18
 19     BEGIN
 20     WRITE( GRN_ON_BLK);
 21     CLRSCRN;
 22     WRITE( VERSION);
 23     END;
 24
 25
 26 PROCEDURE CLRLINE;                  { clear line from position (row,col) }
 27     BEGIN
 28     WRITE( ESC, '[', ROW:0, ';', COL:0, 'H', CLEARLINE);
 29     END;
 30
 31 PROCEDURE CLR2_25;
 32     CONST
 33         DWNCLR = CHR(27)*'[B'*CLEARLINE;
 34         CLR3_25 = DWNCLR*DWNCLR*DWNCLR*DWNCLR*DWNCLR*DWNCLR*DWNCLR*
 35                   DWNCLR*DWNCLR*DWNCLR*DWNCLR*DWNCLR*DWNCLR*DWNCLR*
 36                   DWNCLR*DWNCLR*DWNCLR*DWNCLR*DWNCLR*DWNCLR*DWNCLR*
 37                   DWNCLR*DWNCLR;
 38     BEGIN
 39     WRITEPC( 2, 1, CLR3_25);
 40     END;
 41
 42 PROCEDURE POSCURS;                  { position cursor at (row,col) }
 43     BEGIN
 44     WRITE( ESC, '[', ROW:0, ';', COL:0, 'H');
 45     END;
 46
```

```
47 PROCEDURE WRITEU;
48    VAR
49       LOWER: BOOLEAN;
50       I, LL: WORD;
51       C: CHAR;
52       LSTR: LSTRING( 80);
53    BEGIN
54    COPYLST( STR, LSTR);
55    LOWER := TRUE;
56    LL := LSTR.LEN;
57    FOR I:=1 TO LL
58    DO BEGIN
59       C := LSTR[I];
60       IF (C < 'A') OR (C > 'Z')
61       THEN BEGIN
62          IF NOT LOWER
63          THEN BEGIN
64             LOWER := TRUE;
65             WRITE( NORMFG);
66             END;
67          WRITE( C);
68          END
69       ELSE BEGIN
70          IF LOWER
71          THEN BEGIN
72             LOWER := FALSE;
73             WRITE( MENUFG);
74             END;
75          WRITE( C);
76          END;
77       END;
78    IF NOT LOWER THEN WRITE( MENUFG);
79    END;
80
81
82 PROCEDURE WRITEP;              { position cursor at (row,col) and write str }
83    BEGIN
84    POSCURS( ROW, COL);
85    WRITE( STR);
86    END;
87
88 PROCEDURE WRITEPC;             { clear line from (row,col) and write str }
89    BEGIN
90    CLRLINE( ROW, COL);
91    WRITE( STR);
92    END;
93
94 PROCEDURE WRITEPU;
95    BEGIN
96    POSCURS( ROW, COL);
97    WRITEU( STR);
98    END;
99
100 PROCEDURE WRITEPCU;           { clear line from (row,col) and write str }
101    BEGIN
102    CLRLINE( ROW, COL);
103    WRITEU( STR);
104    END;
105
106 BEGIN
107 END.
```

```
1  INTERFACE(0);
2
3  UNIT SETUP( UPD_SETUP);
4
5  PROCEDURE UPD_SETUP;
6
7  BEGIN
8  END;
1  {$include:'IO\SCREEN.INT'}
2  {$include:'IO\KEYBRD.INT'}
3  {$include:'IO\PROMPT.INT'}
4  {$include:'PRAMIFAC.INT'}
5  {$include:'PHOTOCAL.INT'}
6  {$include:'DATAIFAC.INT'}
7  {$include:'CALMENU.INT'}
8  {$include:'SETUP.INT'}
9
10 IMPLEMENTATION OF SETUP;
11
12 USES SCREEN,
13      KEYBRD,
14      PROMPT,
15      PRAMIFAC,
16      DATAIFAC,
17      CALMENU;
18
19 CONST
20     FGE0 = FVALBND( 0.0, GE, 0.0);
21     GT0 = VALBND( 0, GT, 0);
22     FGT0 = FVALBND( 0.0, GT, 0.0);
23     GE1 = VALBND( 1, GE, 0);
24     GTOLEMAXSEC = VALBND( 0, GTLE, MAXSEC);
25     FGE0LEMAXRUNNO = FVALBND( 0.0, GELE, FMAXRUNNO);
26     FGTABS0 = FVALBND( -273.16, GT, 0.0);
27
28 VAR
29     PR: PR_REC;
30
31 PROCEDURE DSP_SETUP( CONST PR: PR_REC);
32     VAR
33         I, ROW: INTEGER;
34     BEGIN
35     CLR2_25;
36
37     WITH PR
38     DO BEGIN
39         ROW := 3;
40
41         WRITEPU( ROW, 1, 'current Run: ');
42         WRITE( RUNFILNAM( PR.RUNPRFX, PR.RUNNO));
43
44         WRITEPU( ROW, 40, 'heat Flux: ');
45         WRITE( HEATFLUX:0:2);
46
47         ROW := ROW + 2;
48         WRITEPU( ROW, 1, 'run dummy fiLe: ');
49         WRITE( RUN_DUMMY);
50         IF (RUN_DUMMY <> 'ZERO DUMMY') AND THEN
51             NOT (RUN_EXISTS( RUN_DUMMY))
52         THEN WRITE( ERRFG, ' *NOT FOUND*', NORMFG);
53
54         WRITEPU( ROW, 40, 'Auto process: ');
55         IF AUTO_PROC THEN WRITE( 'YES') ELSE WRITE( 'NO');
```

```
56
57        ROW := ROW + 2;
58        WRITEPU( ROW, 1, 'speciMen type: ');
59        IF SPCTYP <> ' '
60        THEN WRITE( SPCTYP)
61        ELSE WRITE( 'normal');
62
63        ROW := ROW + 2;
64        WRITEPU( ROW, 1, 'Times:  hold ');
65        WRITE( HOLDTIME:0);
66        WRITE( '   average ');
67        WRITE( AVRGTIME:0);
68        WRITE( '   burn ');
69        WRITE( BURNTIME:0);
70
71        ROW := ROW + 2;
72        WRITEPU( ROW, 1, 'qK comp: ');
73        WRITE( QK_COMP:0:2, '   Qk uncomp: ', QK_UNCOMP:0:2);
74
75        ROW := ROW + 2;
76        WRITEPU( ROW, 1, 'Volumetric airflow: ');
77        WRITE( VFLOW:0:1, ' 1/sec');
78
79        ROW := ROW + 2;
80        WRITEPU( ROW, 1, 'Surface area: ');
81        WRITE( SRFCAREA:0:1);
82
83        ROW := ROW + 2;
84        WRITEPU( ROW, 1, 'Uncomp tc count: ');
85        WRITE( UNCOMP_CNT:0);
86
87        ROW := ROW + 2;
88        WRITEPU( ROW, 1, 'Inlet air temp: ');
89        WRITE( TINLET:0:0);
90        WRITE( ' °C');
92        END;
93    END;
94
95 PROCEDURE UPD_SETUP;
96    CONST
97       HEADING = 'Test Setup';
98
99    VAR
100       I, J: INTEGER;
101       DONE, UPDATE: BOOLEAN;
102       RTMP: REAL;
103       CH: CHAR;
104       GLSTR: GLSTRTYP;
105       PSTR: LSTRING(80);
106       TMPBND: VALBND;
107
108    BEGIN
109    GET_PARAM( PR);
110
111    DONE := FALSE;
112    UPDATE := TRUE;
113    REPEAT
114       WRITEPC( 1, 30, HEADING);
115       IF UPDATE THEN DSP_SETUP( PR) ELSE UPDATE := TRUE;
116       WRITEPC( 24, 1, 'COMMAND: ');
117       WRITEU( 'Calibrate /Quit ? ');
118       CH := GETCHU;
119       CLRLINE( 25, 1);
```

```
120        CASE CH OF
121
122        'A':  PR.AUTO_PROC := NOT PR.AUTO_PROC;
123
124        'C':  BEGIN
125                 PUT_PARAM( PR);
126                 CAL_MENU;
127                 GET_PARAM( PR);
128              END;
129
130        'F':  BEGIN
131                 UPDATER( 24, 1, 'Heat flux (kW/cm²) ? ', PR.HEATFLUX, FGEO);
132                 WITH PR
133                 DO BEGIN
134                    IF HEATFLUX = 1.5 THEN RUNPRFX := 'A'
135                    ELSE IF HEATFLUX = 2.5 THEN RUNPRFX := 'B'
136                    ELSE IF HEATFLUX = 3.5 THEN RUNPRFX := 'C'
137                    ELSE IF HEATFLUX = 5.0 THEN RUNPRFX := 'D'
138                    ELSE IF HEATFLUX = 7.5 THEN RUNPRFX := 'E'
139                    ELSE BEGIN
140                       WRITEPC( 24, 1, 'Heat flux prefix (F..Z) ? ');
141                       REPEAT
142                          PR.RUNPRFX := GETCHU;
143                          UNTIL RUNPRFX IN ['F'..'Z'];
144                       END;
145                    END;
146              END;
147
148        'I':  UPDATER( 24, 1, 'Inlet air temperature in °C ? ',
149                       PR.TINLET, FGTABSO);
150
151        'K':  BEGIN
152                 UPDATER( 24, 1, 'Compensated cal constant (KW/mV/m²) ? ',
153                          PR.QK_COMP, FGEO);
154                 UPDATER( 24, 1, 'Uncompensated cal constant (KW/mV/m²) ? ',
155                          PR.QK_UNCOMP, FGEO);
156              END;
157
158        'L':  BEGIN
159
160                 GLSTR := PR.RUN_DUMMY;
161                 IF PROMPTL( 24, 1, 'Dummy file used for data reduction ? ', GLSTR)
162                 THEN BEGIN
163                    TRIM( GLSTR);
164                    LWRUPR( GLSTR);
165                    IF GLSTR.LEN > 0 THEN PR.RUN_DUMMY := GLSTR;
166                    END;
167              END;
168
169        'M':  BEGIN
170                 WRITEPC( 24, 1, 'Specimen type (A-Z,0-9 or Enter) ? ');
171                 REPEAT
172                    CH := GETCHU;
173                    IF CH < ' ' THEN CH := ' ';
174                    UNTIL CH IN [' ','0'..'9','A'..'Z'];
175                 PR.SPCTYP := CH;
176              END;
177
178        'Q':  DONE := TRUE;
179
180        'R':  BEGIN
181                 RTMP := FLOAT4( PR.RUNNO);
182                 UPDATER( 24, 1, 'Run number ? ', RTMP, FGEOLEMAXRUNNO);
```

```
183                    PR.RUNNO := TRUNC4( RTMP);
184                    END;
185
186        'S':   UPDATER( 24, 1, 'Surface area of specimen (cm²) ? ',
187                        PR.SRFCAREA, FGTO);
188
189        'T':   BEGIN
190                REPEAT
191                    I := PR.HOLDTIME;
192                    J := PR.AVRGTIME;
193                    UPDATEI( 24, 1, 'Hold Time (sec) ? ', I, GTO);
194                    UPDATEI( 24, 1, 'Average Time (sec) ? ', J, GTO);
195                    IF I < J
196                    THEN WRITEPC( 25, 1,
197 'Average Time must be less than or equal to Hold Time');
198                    UNTIL I >= J;
199                CLRLINE( 25, 1);
200                PR.HOLDTIME := I;
201                PR.AVRGTIME := J;
202                UPDATEI( 24, 1, 'Burn Time (sec) ? ', PR.BURNTIME, GTOLEMAXSEC);
203                END;
204
205        'U':   UPDATEI( 24, 1, 'TC pairs in uncompensated circuit ? ',
206                        PR.UNCOMP_CNT, GE1);
207
208        'V':   UPDATER( 24, 1, 'Volumetric air flow (1/sec) ? ', PR.VFLOW, FGE0);
209
210        OTHERWISE
211            BEGIN
212            WRITEPC( 25, 1, 'Unknown Command');
213            UPDATE := FALSE;
214            END;
215
216        END;
218        UNTIL DONE;
219
220    PUT_PARAM( PR);
221    CLR2_25;
222    END;
223
224 BEGIN
225 END.
  1 INTERFACE(0);
  2
  3 UNIT TAKEDATA( RUN_SCRN);
  4
  5 PROCEDURE RUN_SCRN;
  6
  7 BEGIN
  8 END;
  1 {$include:'IO\SCREEN.INT'}
  2 {$include:'IO\KEYBRD.INT'}
  3 {$include:'IO\PROMPT.INT'}
  4 {$include:'PRAMIFAC.INT'}
  5 {$include:'PHOTOCAL.INT'}
  6 {$include:'DATAIFAC.INT'}
  7 {$include:'HARDWARE.INT'}
  8 {$include:'SETUP.INT'}
  9 {$include:'DATACQ.INT'}
 10 {$include:'DP\DATAPROC.INT'}
 11 {$include:'TAKEDATA.INT'}
 12
 13 IMPLEMENTATION OF TAKEDATA;
```

```
14
15 USES SCREEN,
16      KEYBRD,
17      PROMPT,
18      DATAIFAC,
19      PRAMIFAC,
20      HARDWARE,
21      SETUP,
22      DATAPROC,
23      DATACQ;
24
25 CONST
26     ESC = CHR( 27);
27     CR = CHR( 13);
28     GT0 = VALBND( 0, GT, 0);
29     GTOLEMAXSPC = VALBND( 0, GTLE, MAXSPC);
30
31 VAR
32     RUNROW: INTEGER;
33     FIRST: BOOLEAN;
34     PR: PR_REC;
35
36 PROCEDURE DSP_RUNNO;
37     BEGIN
38     WRITEP( RUNROW, 1, 'current run: ');
39     WRITE( RUNFILNAM( PR.RUNPRFX, PR.RUNNO));
40     END;
41
42 PROCEDURE DSP_DAMENU;
43     VAR
44         I, ROW: INTEGER;
45     BEGIN
46     IF FIRST THEN FIRST := FALSE ELSE CLR2_25;
47
48     WITH PR
49     DO BEGIN
50         ROW := 3;
51         RUNROW := ROW;
52         DSP_RUNNO;
53
54         WRITEP( ROW, 40, 'heat flux: ');
55         WRITE( HEATFLUX:0:2);
56
57         ROW := ROW + 2;
58         WRITEP( ROW, 1, 'run dummy file: ');
59         WRITE( RUN_DUMMY);
60         IF (RUN_DUMMY <> 'ZERO DUMMY') AND THEN
61             NOT (RUN_EXISTS( RUN_DUMMY))
62         THEN WRITE( ERRFG, '  NOT FOUND', NORMFG);
63
64         WRITEP( ROW, 40, 'Auto process: ');
65         IF AUTO_PROC THEN WRITE( 'YES') ELSE WRITE( 'NO');
66
67         ROW := ROW + 2;
68         WRITEPU( ROW, 1, 'specimen type: ');
69         IF SPCTYP <> ' ' THEN WRITE( SPCTYP) ELSE WRITE( 'normal');
70         END;
71     END;
72
73 FUNCTION TAKDAT: BOOLEAN;
74     LABEL
75         86; { Error exit }
76
```

```
 77    VAR
 78         SETLIM, SETCNT, SPC, ROW, J, K, W, BEGSPC: INTEGER;
 79         CH: CHAR;
 80         ABORTED, AGAIN, APPEND: BOOLEAN;
 81         TSTR: GLSTRTYP;
 82         FILNAM: FILNAMTYP;
 83         OSUDAT: OSUTYP;
 84         SLP, OFS: MVVCT;
 85         DMYFND, COMPAT, LENGTH, IDENT: BOOLEAN;
 86         GTOLEN: VALBND;
 87         APP_CND: DAT_IFAC;
 88
 89
 90
 91    BEGIN
 92    CLRLINE( 24, 1);
 93
 94    IF NOT DATACQ_SETUP( SLP, OFS)
 95    THEN BEGIN
 96       WRITEPC( 25, 1, ERRFG*'Not all channels calibrated'*NORMFG);
 97       TAKDAT := FALSE;
 98       GOTO 86;
 99       END;
100
101    APPEND := FALSE;
102    AGAIN := TRUE;
103    FILNAM := RUNFILNAM( PR.RUNPRFX, PR.RUNNO);
104    IF RUN_EXISTS( FILNAM)
105    THEN BEGIN
106       WRITEPC( 25, 1, 'Run number exists: ');
107       WRITE( FILNAM);
108       WRITEPC( 24, 1, 'Do you wish to: ');
109       WRITEU( 'Append /Delete /Neither ? ');
110       REPEAT CH := GETCHU; UNTIL (CH = 'A') OR (CH = 'D') OR (CH = 'N');
111
112       CLRLINE( 24, 1);
113       CLRLINE( 25, 1);
114
115       IF CH = 'D'
116       THEN DELETE_RUN( FILNAM)
117       ELSE BEGIN { A or N }
118          IF CH = 'A'
119          THEN BEGIN
120             RUN_COMPAT( PR, FILNAM, DMYFND, COMPAT, IDENT, LENGTH);
121             IF IDENT
122             THEN BEGIN
123                APPEND := TRUE;
124                LOAD_HDR( FILNAM, APP_CND);
125                END
126             ELSE WRITEP( 25, 1, 'Run conditions not identical');
127             END;
128
129          IF NOT APPEND
130          THEN BEGIN
131             TAKDAT := FALSE;
132             GOTO 86;
133             END;
134          END;
135       END;
136
137    IF PR.RUN_DUMMY <> 'ZERO DUMMY'
138    THEN BEGIN
139       RUN_COMPAT( PR, PR.RUN_DUMMY, DMYFND, COMPAT, IDENT, LENGTH);
```

```
140     IF NOT DMYFND
141     THEN WRITEPC( 23, 1, ERRFG*'Dummy file not found'*NORMFG)
142     ELSE IF NOT LENGTH
143     THEN WRITEPC( 23, 1, ERRFG*'Dummy file too short'*NORMFG)
144     ELSE IF NOT COMPAT
145     THEN WRITEPC( 23. 1. ERRFG*'Dummy file not compatible with run parameters'
           *NORMF G);
146     END;
147
148     ROW := 10;
149     WHILE AGAIN AND THEN APPEND OR ELSE PROMPTL( ROW, 1, 'WR # ? ', TSTR)
150     DO BEGIN
151        IF APPEND
152        THEN BEGIN
153           WRITEPC( ROW, 1, 'WR # ? ');
154           TSTR := APP_CND.WR_NUMBER;
155           WRITE( TSTR);
156           AGAIN := FALSE;
157           END;
158        PR.WR_NUMBER := TSTR;
159
160        ROW := ROW+2;
161        IF APPEND
162        THEN BEGIN
163           WRITEPC( ROW, 1, 'Number of Sets ? 1');
164           SETLIM := 1;
165           END
166        ELSE BEGIN
167           IF NOT (PROMPTI( ROW, 1, 'Number of Sets ? ', SETLIM, GT0))
168           THEN SETLIM := 0;
169           END;
170
171        SETCNT := 1;
172        WHILE SETCNT <= SETLIM
173        DO BEGIN
174
175           IF NOT APPEND
176           THEN BEGIN
177              FILNAM := RUNFILNAM( PR.RUNPRFX, PR.RUNNO);
178              IF RUN_EXISTS( FILNAM)
179              THEN BEGIN
180                 WRITEPC( 25, 1, 'Run number exists: ');
181                 WRITE( FILNAM);
182                 TAKDAT := FALSE;
183                 GOTO 86;
184                 END;
185              END;
186
187           ROW := ROW+2;
188           IF APPEND
189           THEN BEGIN
190              WRITEPC( ROW, 1, 'Material Description ? ');
191              TSTR := APP_CND.MATERIAL;
192              WRITE( TSTR);
193              END
194           ELSE IF NOT (PROMPTL( ROW, 1, 'Material Description ? ', TSTR))
195              THEN SETLIM := -1;
196
197           IF SETLIM > 0
198           THEN BEGIN
199              PR.MATERIAL := TSTR;
200
201              ROW := ROW+2;
```

```
202      IF APPEND
203      THEN BEGIN
204         GTOLEN := VALBND( 0, GTLE, 0);
205         GTOLEN.HIBND := MAXSPC - APP_CND.SPCCNT;
206         IF NOT PROMPTI( ROW, 1, 'Number of Additional Specimens ? ', SPC.
            GTOLEN)
207         THEN SPC := 0;
208         SPC := APP_CND.SPCCNT+SPC;
209         BEGSPC := APP_CND.SPCCNT+1;
210         PR.SPCCNT := BEGSPC;
211         END
212      ELSE BEGIN
213         IF NOT PROMPTI( ROW, 1, 'Number of Specimens ? ', SPC, GTOLEMAXSPC)
214         THEN SPC := 0;
215         BEGSPC := 1;
216         PR.SPCCNT := BEGSPC;
217         END;
218
219      ABORTED := FALSE;
220      WHILE (PR.SPCCNT <= SPC) AND NOT ABORTED
221      DO BEGIN
222         WRITEPC( 24, 1, 'Insert Specimen #');
223         WRITE( PR.SPCCNT:0, ' and hit Enter to start run');
224         REPEAT
225            CH := GETCH;
226            IF CH = ESC THEN ABORTED := TRUE;
227            UNTIL (CH = CR) OR ABORTED;
228         CLRLINE( 24, 1);
229
230         IF NOT ABORTED
231         THEN BEGIN
232            IF RECORD_DATA( OSUDAT)
233            THEN BEGIN
234               STORE_RUN( PR, OSUDAT, SLP, OFS, FILNAM);
235               PR.SPCCNT := PR.SPCCNT + 1;
236               END
237            ELSE BEGIN
238               WRITEPC( 24, 1, 'Do you have a spare specimen ');
239               WRITEU( '(Y/N) ? ');
240               REPEAT CH := GETCHU; UNTIL (CH = 'Y') OR (CH = 'N');
241               IF CH <> 'Y' THEN SPC := SPC-1;
242               END;
243            END;
244         END;
245
246      CLRLINE( 24, 1);
247      CLRLINE( ROW, 1);
248      ROW := ROW-2;
249      APPEND := FALSE;
250      IF PR.SPCCNT > BEGSPC   { data was stored }
251      THEN BEGIN
252         IF PR.AUTO_PROC THEN REPORT( PR, FILNAM);
253         PR.RUNNO := PR.RUNNO+1;
254         IF PR.RUNNO > 99999 THEN PR.RUNNO := 0:
255            DSP_RUNNO;
256            PUT_PARAM( PR);
257            END;
258         END;
259
260      CLRLINE( ROW, 1);
261      ROW := ROW-2;
262      SETCNT := SETCNT + 1;
263      END;
```

```
264
265         CLRLINE( ROW, 1);
266         ROW := ROW-2;
267         END;
268
269     TAKDAT := TRUE;
270
271 86:
272     END;
273
274 PROCEDURE RUN_SCRN;
275     CONST
276         HEADING = 'Data Acquisition';
277
278     VAR
279         DONE, UPDATE: BOOLEAN;
280         CH: CHAR;
281
282     BEGIN
283     GET_PARAM( PR);
284     FIRST := TRUE;
285
286     DONE := FALSE;
287     UPDATE := TRUE;
288     REPEAT
289         IF UPDATE THEN DSP_DAMENU ELSE UPDATE := TRUE;
290         WRITEPC( 1, 30, HEADING);
291         WRITEPC( 24, 1, 'COMMAND: ');
292         WRITEU( 'Data processing /Hardware /Quit /Setup /Take data ? ');
293         CH := GETCHU;
294         CLRLINE( 25, 1);
295         CASE CH OF
296
297         'D':  DATPRC( PR);
298
299         'H':  BEGIN
300               UPD_HRDWAR;
301               GET_PARAM( PR);
302               END;
303
304         'Q':  DONE := TRUE;
305
306         'S':  BEGIN
307               UPD_SETUP;
308               GET_PARAM( PR);
309               END;
310
311         'T':  UPDATE := TAKDAT;
312
313         OTHERWISE
314               BEGIN
315               WRITEPC( 25, 1, 'Unknown Command');
316               UPDATE := FALSE;
317               END;
318
319           END { case };
320
321         UNTIL DONE;
322     PUT_PARAM( PR);
323     CLR2_25;
324     END;
325
326 BEGIN
327 END.
```

What is claimed is:

1. A user-operated computer control system which calculates the amount of heat released by a burning material within a test apparatus, said apparatus including:

a calorimeter characterized in that it has certain hardware elements including a heating chamber through which a forced airflow passes, a chamber doorway operable to be opened and closed, a holding chamber positioned outside said doorway for holding a test sample of said material, said chamber doorway permitting access from said holding chamber into said heating chamber, an actuator operable to extend through said holding chamber in a manner so as to move said test sample through said doorway after said doorway has been opened and into said heating chamber airflow, said doorway being further operable to close around at least a portion of said extended actuator after said test sample is moved into said heating chamber, a plurality of electrical radiant heating elements positioned in said heating chamber for providing heat to said test sample, to heat and burn the same, said radiant heating elements being adjustably operable to vary the amount of heat they provide to said test sample, and including pilot burners normally positioned above and below said test sample when said test sample is in said heating chamber, and means for sensing the change in temperature of said chamber airflow caused by heating and burning said test sample, and said computer control system comprising:

a programmable computer operatively connected to said hardware elements of said calorimeter, said computer having input means operable by a user of said test apparatus to input user instructions into said computer, and output means for displaying information to said user, said computer being programmed to cause said computer's output means to display a menu of user-selectible options for conducting a test, such options to be input into said computer by user operation of said input means, and said options at least including:

user selection of the times at which said chamber doorway is to be opened and closed, and said actuator is to be operated to move said test sample into said chamber, user selection of the total time said test sample is to remain in said chamber, and user selection of the rate of heat supplied by said heating elements to said test sample, and user selection of at least one calibration constant for equating temperature changes of said chamber airflow into heat release of said test sample as it burns; and still further said computer being programmed to operate said hardware elements of said calorimeter to conduct said test in accordance with said user-selected options, and to automatically sense changes in temperature of said chamber airflow caused by heating and burning said test sample, and to use said sensed temperature changes to automatically calculate the amount of heat released by said test sample during said test.

2. The apparatus of claim 1, wherein said calorimeter is further characterized in that its heating chamber has a vent stack through which said airflow exits said chamber, and a light source and photocell receptor positioned opposite each other in a manner so that said photocell receptor receives light from said light source, and in a manner so that said exiting airflow passes between them, so that any smoke generated by burning said test sample in said chamber airflow reduces the amount of light transmitted from said light source to said photocell receptor, said photocell receptor generating an output signal that is proportional to the amount of light it receives, and said computer is further programmed to prompt said user to calibrate, prior to a particular test, said photocell receptor output to the amount of light said photocell receptor receives, said computer also being programmed to automatically sense changes in photocell receptor output, and to use said sensed output to calculate the smoke release rate of said test sample during said test.

* * * * *